(12) United States Patent
Shin et al.

(10) Patent No.: US 9,534,240 B2
(45) Date of Patent: Jan. 3, 2017

(54) RECOMBINANT MICROORGANISM PRODUCING QUINOLINIC ACID AND A METHOD FOR PRODUCING QUINOLINIC ACID USING THE SAME

(71) Applicant: CJ Cheiljedang Corporation, Seoul (KR)

(72) Inventors: Yong Uk Shin, Yongin-si (KR); So Young Kim, Gwacheon-si (KR); In Kyung Heo, Seoul (KR); Ju Eun Kim, Seoul (KR); Sung Kwang Son, Seoul (KR); Jae Hee Lee, Seoul (KR); Ji Hyun Lee, Seoul (KR); Chang Gyeom Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 151 days.

(21) Appl. No.: 14/370,721

(22) PCT Filed: Jan. 3, 2013

(86) PCT No.: PCT/KR2013/000030
§ 371 (c)(1),
(2) Date: Jul. 3, 2014

(87) PCT Pub. No.: WO2013/103246
PCT Pub. Date: Jul. 11, 2013

(65) Prior Publication Data
US 2015/0037850 A1 Feb. 5, 2015

(30) Foreign Application Priority Data
Jan. 6, 2012 (KR) .................. 10-2012-0001845

(51) Int. Cl.
| | |
|---|---|
| *C12P 7/40* | (2006.01) |
| *C12N 1/20* | (2006.01) |
| *C12P 17/12* | (2006.01) |
| *C12N 15/62* | (2006.01) |
| *C12N 9/06* | (2006.01) |
| *C12N 9/10* | (2006.01) |
| *C12N 15/70* | (2006.01) |
| *C12N 15/52* | (2006.01) |

(52) U.S. Cl.
CPC ............. *C12P 17/12* (2013.01); *C12N 9/0022* (2013.01); *C12N 9/1085* (2013.01); *C12N 15/52* (2013.01); *C12N 15/62* (2013.01); *C12N 15/70* (2013.01); *C12Y 104/03016* (2013.01); *C12Y 205/01072* (2013.01); *Y02P 20/52* (2015.11)

(58) Field of Classification Search
CPC ..................................... C12N 1/20; C12P 7/40
USPC ........................................................ 435/252.3
See application file for complete search history.

(56) References Cited

U.S. PATENT DOCUMENTS

| | | | |
|---|---|---|---|
| 6,271,031 B1 | 8/2001 | Falco et al. | |
| 8,758,764 B2 * | 6/2014 | Masignani ......... | A61K 39/0258 424/185.1 |

FOREIGN PATENT DOCUMENTS

| | | |
|---|---|---|
| DE | 3826041 C2 | 4/1993 |
| EP | 0279273 B1 | 12/1993 |
| KR | 10-2012-0082673 A | 7/2012 |

OTHER PUBLICATIONS

Arai et al., Protein Engineering, 14(8), 2001, 529-532, 2001.*
Bulow L. et al. "Multienzyme Systens Obtained by Gene Fusion", Trends in Biotechnology, Elsevier Publications, Cambridge, GB, vol. 9, No. 1, Jan. 1, 2991, pp. 226-231.
Extended European Search Report, issued Jun. 26, 2015 in connection with European Patent Application No. 13733832.3, national stage of PCT International Application No. PCT/KR2013/000030, filed Jan. 3, 2013.
Chandler & Gholson (1972). De novo biosynthesis of nicotinamide adenine dinucleotide in *Escherichia coli*: excretion of quinolinic acid by mutants lacking quinolinate phosphoribosyl transferase. *Journal of Bacteriology*, 111(1), 98-102.
Flachmann et al. (1988). Molecular biology of pyridine nucleotide biosynthesis in *Escherichia coli*. Cloning and characterization of quinolinate synthesis genes nadA and nadB. *European Journal of Biochemistry*, 175, 221-228.
Nasu, Wicks, & Gholson (1982). L-aspartate oxidase, a newly discovered enzyme of *Escherichia coli*, is the B protein of quinolinate synthetase. *The Journal of Biological Chemistry*, 257(2), 626-632.
International Search Report, mailed May 30, 2013 in connection with PCT International Application No. PCT/KR2013/000030, filed Jan. 3, 2013.

* cited by examiner

*Primary Examiner* — Maryam Monshipouri
(74) *Attorney, Agent, or Firm* — John P. White; Cooper & Dunham LLP

(57) ABSTRACT

The present invention relates to a quinolinic acid-producing recombinant microorganism expressing a fusion protein of L-aspartate oxidase and quinolinate synthase linked via a linker, and a method for producing quinolinic acid using the same.

10 Claims, 2 Drawing Sheets

L(GGGS)₃₋₄AAA
LA(EAAAK)₁₋₅AAA

RECOMBINANT MICROORGANISM PRODUCING QUINOLINIC ACID AND A METHOD FOR PRODUCING QUINOLINIC ACID USING THE SAME

CROSS-REFERENCE TO RELATED APPLICATIONS

This application is a §371 national stage of PCT International Application No. PCT/KR2013/000030, filed Jan. 3, 2013, claiming priority of Korean Patent Application No. 10-2012-0001845, filed Jan. 6, 2012, the contents of each of which are hereby incorporated by reference in their entirety.

REFERENCE TO SEQUENCE LISTING

This application incorporates-by-reference nucleotide and/or amino acid sequences which are present in the file named "141027_5034_86636_Substitute_Sequence_ Listing_JR.txt," which is 156 kilobytes in size, and which was created Sep. 26, 2014 in the IBM-PC machine format, having an operating system compatibility with MS-Windows, which is contained in the text file filed Oct. 27, 2014 as part of this application.

BACKGROUND OF THE INVENTION

1. Field of the Invention

The present invention relates to a recombinant microorganism producing quinolinic acid, and a method for producing quinolinic acid using the same.

2. Description of the Related Art

Quinolinic acid, which is also called 2,3-pyridine-dicarboxylic acid, has a wide variety of applications as a precursor of synthetic chemicals in the production of medicinal or agricultural chemicals, dyes or the like.

Quinolinic acid can be prepared by chemical or biological synthetic methods. because of using non-renewable materials derived from petroleum as the raw material, chemical synthetic methods are greatly influenced by environmental problems, oil prices or the unit cost of petroleum extraction.

For Example of a representative biological synthetic method, a method of producing quinolinic acid in an *E. coli* strain is disclosed that expression of genes encoding L-aspartate oxidase (NadB) and quinolinate synthase (NadA) is enhanced by cloning a plasmid having different copy numbers of the two genes into *E. coli*, of which quinolinate phosphoribosyltransferase activity is eliminated (Eur. J. Biochem. 175, 221-228 (1988), DE3826041). In this regard, the concentration of quinolinic acid produced is as low as 500 mg/L or less. The first reason of this low production of quinolinic acid is transcriptional suppression by NadR, which is a NAD-related transcriptional repressor of nadB encoding L-aspartate oxidase and nadA encoding quinolinate synthase. The second reason is feedback inhibition of L-aspartate oxidase, NadB protein by NAD. And the third reason is a weak biosynthetic pathway from carbon sources to L-aspartic acid in *E. coli*.

To solve the first reason, in Korean Patent laid-open No. 10-2012-0082673, a microorganism strain was used to increase the production of quinolinic acid to 5.5 g/L, wherein the promoter regions of L-aspartate oxidase (NadB) and quinolinate synthase (NadA), which are the quinolinate synthesis genes suppressed at the transcriptional level, were substituted with a constitutive promoter, and L-aspartic acid biosynthetic pathway is enhanced.

The biosynthetic pathway of quinolinic acid from L-aspartic acid by a biological synthetic method is as shown in the following reaction scheme:

1) L-aspartate Oxidase (NadB)

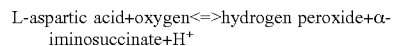

2) Quinolinate Synthase (NadA)

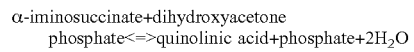

α-iminosuccinate as an intermediate of the quinolinic acid biosynthetic pathway is an unstable substance, and is converted to oxaloacetate by natural deamination reaction in cells (THE JOURNAL OF BIOLOGICAL CHEMISTRY, Vol. 257, No. 2, Issue of January 25. pp. 626-632, 1982). In general, when an unstable intermediate metabolite is used as a substrate, the low collision frequency between the substrate and enzyme produces a large amount of by-products. However, until now, there has been no attempt to solve the above problem regarding the production of quinolinic acid.

On the other hand, a fusion protein technology of linking heterogeneous enzymes or proteins via an amino acid linker to express as a single protein, has been used for various purposes, such as increasing the protein expression level by linking a protein showing a low level-expression with a protein showing a high level-expression, increasing the protein purification yield by preparing a fusion protein linked with a tag, or the like.

Design of the linker is known to be important in the preparation of fusion proteins. In general, a helical linker having an alpha-helix structure or a flexible linker having structural flexibility has been frequently used, and for example, various linkers can be designed and used by the combination of the two linkers according to the characteristics of the fusion protein to be achieved.

The present inventors have tried to solve the reduced reaction due to unstable metabolites by expression of a fusion protein of NadB and NadA linked via various types of amino acid linkers, and then they found that quinolinic acid can be produced in a high yield by expression of the fusion protein, compared to the yield of the conventional biological production method, thereby completing the present invention.

SUMMARY OF THE INVENTION

An object of the present invention is to provide a quinolinic acid-producing recombinant microorganism, which expresses a fusion protein of L-aspartate oxidase and quinolinate synthase linked via a linker.

Another object of the present invention is to provide a method for producing quinolinic acid, including the steps of culturing the recombinant microorganism and recovering quinolinic acid produced during the cultivation.

DETAILED DESCRIPTION OF THE PREFERRED EMBODIMENTS

Figure 1:
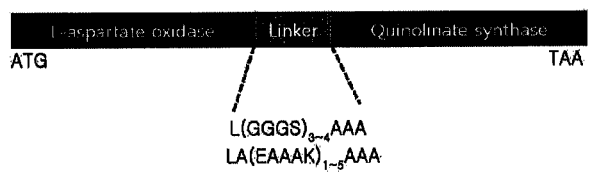
FIG. 1 shows a structure of a fusion protein of L-aspartate oxidase and quinolinate synthase according to one specific embodiment of the present invention.

In one aspect, the present invention provides a recombinant microorganism producing quinolinic acid, which expresses a fusion protein of L-aspartate oxidase and quinolinate synthase linked via a linker.

The L-aspartate oxidase (hereinafter, referred to as 'NadB') is an enzyme having an activity to oxidize L-aspartic acid to iminosuccinic acid, and may have an amino acid sequence represented by SEQ ID NO. 42 or an amino acid sequence having high homology therewith.

[Activity of L-aspartate Oxidase]

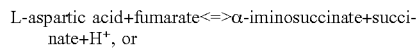

L-aspartic acid+fumarate<=>α-iminosuccinate+succinate+H⁺, or

L-aspartic acid+oxygen<=>hydrogen peroxide+α-iminosuccinate+H⁺

The sequence of nadB gene encoding this enzyme can be obtained from the genome sequence of *Escherichia coli* (GI: 89109380) as published in the literature (Mol Syst Biol. 2006; 2:2006.0007. Epub 2006 Feb. 21), or the database available from the National Center for Biotechnology Information (NCBI) or the DNA Data Bank for Japan (DDBJ).

The quinolinate synthase (hereinafter, referred to as 'NadA') is an enzyme having an activity to synthesize quinolinic acid from iminosuccinic acid, and may have an amino acid sequence represented by SEQ ID NO. 43 or an amino acid sequence having high homology therewith.

[Activity of Quinolinate Synthase]

α-iminosuccinate+dihydroxyacetone phosphate<=>quinolinic acid+phosphate+2H₂O

The sequence of nadA gene encoding this enzyme can be obtained from the genome sequence of *Escherichia coli* (GI: 89109380) as published in the literature (Mol Syst Biol. 2006; 2:2006.0007. Epub 2006 Feb. 21), or the database available from NCBI or DDBJ.

If the activities of NadB and NadA are enhanced, accumulation of α-iminosuccinate as the precursor of quinolinic acid and biosynthesis of quinolinic acid from α-iminosuccinate can be increased in cells, thereby increasing the production of quinolinic acid. However, although activities and expression levels of the two enzymes (NadB and NadA) are increased, the low collision frequency between the substrate and the enzyme produces a large amount of by-products because α-iminosuccinate is an unstable metabolite. Consequently, it is difficult to efficiently produce quinolinic acid, as expected. In order to solve this problem, in the present invention, NadB and NadA are linked to each other via a linker and expressed in a strain in the form of a fusion protein, thereby producing quinolinic acid in a high yield.

The NadB and NadA may have amino acid sequences represented by SEQ ID NOs. 42 and 43, respectively. However, depending on the species or strain of the microorganism, there may be differences in the amino acid sequences of proteins showing the activity, and thus they are not limited thereto. That is, as long as NadB and NadA are provided in the form of a fusion protein prepared by liking each other via a linker so as to contribute to an increase of quinolinic acid productivity, they may be mutants or artificial variants having modified amino acid sequences resulting from substitution, deletion, insertion or addition of one amino acid or several amino acids at one or more positions in the amino acid sequences of SEQ ID NOs. 42 and 43. Herein, the term 'several' may vary depending on type or positions of amino acid residues in the three-dimensional structure of the protein, and in details, it may be 2 to 20, specifically 2 to 10, and more specifically 2 to 5. Furthermore, the substitutions, deletions, insertions, additions, or inversions of amino acids may include naturally occurring mutants or artificial variants, based on individual differences and/or species differences of the microorganism expressing the polypeptide.

Polynucleotides encoding NadB and NadA enzymes may be polynucleotides encoding the proteins having 80% or more homology, specifically 90% or more homology, more specifically 95% or more homology, much more specifically 97% or more homology with the amino acid sequences of SEQ ID NOs. 42 and 43, as long as they have enzymatic activities of NadB and NadA as shown in the above Reaction Scheme. Most specifically, the polynucleotides may have polynucleotide sequences represented by SEQ ID NO. 27 and SEQ ID NO. 28, respectively.

As used herein, the term "homology" refers to identity between two amino acid sequences, and can be determined by a method widely known to those skilled in the art, for example, BLAST 2.0, which calculates parameters such as score, identity, and similarity.

The polynucleotide sequence encoding NadB or NadA enzyme may be polynucleotide sequence of SEQ ID NO. 27 or SEQ ID NO. 28 or hybridized with a probe which can be prepared from the polynucleotide sequence under 'stringent conditions', and may be a variants encodes a protein which functions normally.

As used herein, the term "stringent conditions" means conditions which permit specific hybridization between polynucleotides. A detailed description is disclosed in Molecular Cloning (A Laboratory Manual, J. Sambrook at al., Editors, 2nd Edition, Cold Spring Harbor Laboratory press, Cold Spring Harbor, N.Y., 1989) or Current Protocols in Molecular Biology (F. M. Ausubel at al., Editors, John Wiley & Sons, Inc., New York), and for example, hybridization in a hybridization buffer (3.5×SSC, 0.02% Ficoll, 0.02% polyvinylpyrrolidone, 0.02% bovine serum albumin, 2.5 mM NaH₂PO₄ (pH 7), 0.5% SDS, 2 mM EDTA) at 65° C. SSC is 0.15 M sodium chloride/0.15 M sodium citrate at pH 7. After hybridization, the membrane to which the DNA has been transferred is washed with 2×SSC at room temperature, and then washed with 0.1 to 0.5×SSC/0.1×SDS at 68° C.

The fusion protein of the present invention is a polypeptide, in which L-aspartate oxidase and quinolinate synthase having different activities are linked to each other via an amino acid linker, and has biosynthetic activity of quinolinic acid from L-aspartic acid as in the following Reaction Scheme.

[Activity of Fusion Protein]

L-aspartic acid+oxygen+dihydroxyacetone phosphate<=>quinolinic acid+phosphate+2H₂O+ hydrogen peroxide If the activity of the fusion protein is enhanced, a conversion rate of quinolinic acid from the α-iminosuccinate, intermediate metabolite, is improved, thereby producing quinolinic acid with much higher productivity than the productivity achieved by independent enhancement of activities of NadB and NadA.

The fusion protein may be a polypeptide prepared by linking the N-terminus of L-aspartate oxidase and the C-terminus of quinolinate synthase via a linker, or a polypeptide prepared by linking the C-terminus of L-aspartate oxidase and the N-terminus of quinolinate synthase via a linker, and specifically, the fusion protein may have an amino acid sequence selected from the group consisting of SEQ ID NOs. 47, 48, 49, 50, 51, 52 and 53.

The linker is placed between NadB and NadA polypeptides, or between genes encoding them, and it may be a helical or flexible linker. In addition, as the linker, the helical or flexible linker may be used singly or in combination. As the helical linker, "EAAAK" or "EAAAR" may be used, and as the flexible linker, "GGSGGS", "GGGS", "GGSG" or "GS" may be used, but they are not limited thereto.

The linker may be composed of 5 to 30 amino acid sequences, and the helical or flexible linker may be used singly or repeatedly.

According to one specific embodiment, a linker containing the helical linker may be LA(EAAAK)nAAA, and a linker containing the flexible linker may be L(GGGS)nAAA. Preferably, n may be an integer of 1 to 5.

According to one specific embodiment, the linker may have an amino acid sequence selected from the group consisting of SEQ ID NOs. 54, 55, 56, 57, 58, 59 and 60, or an amino acid sequence having high homology therewith, but is not limited thereto.

The "recombinant microorganism producing quinolinic acid" of the present invention is a microorganism which can produce and accumulate quinolinic acid from a carbon source in a medium, and express the fusion protein of L-aspartate oxidase and quinolinate synthase linked via the linker, thereby producing quinolinic acid with high productivity.

The recombinant microorganism of the present invention can be prepared to express a fusion protein by introducing a polynucleotide encoding the fusion protein.

According to one specific embodiment, the recombinant microorganism of the present invention can be prepared by transformation using a recombinant vector comprising the polynucleotide encoding the fusion protein.

As used herein, the term "transformation" means that a gene is introduced into a host cell so that it can be expressed in the host cell. The transformed gene can be located anywhere without limitation, whether it is inserted in the chromosome of a host cell or located outside the chromosome, as long as it can be expressed in the host cell. In addition, the gene may be introduced in any form, as long as it can be introduced and expressed in a host cell. For example, the gene may be introduced into a host cell in the form of an expression cassette that is a polynucleotide structure including all elements required for self-expression. The expression cassette generally comprises a promoter operably linked to the gene, a transcription termination signal, a ribosome binding site and a translation termination signal. The expression cassette may be in the form of a self-replicable expression vector. In addition, the gene may be introduced into a host cell in the form of a polynucleotide structure or itself, and may be operably linked to a sequence required for expression in the host cell.

The recombinant vector is a means for expressing the fusion protein by introducing a DNA into a host cell to prepare a microorganism expressing the fusion protein of the present invention, and a known expression vector, such as a plasmid vector, a cosmid vector or a bacteriophage vector can be used. The vector can be easily prepared by those skilled in the art according to any known method using DNA recombination technology.

Figure 2:
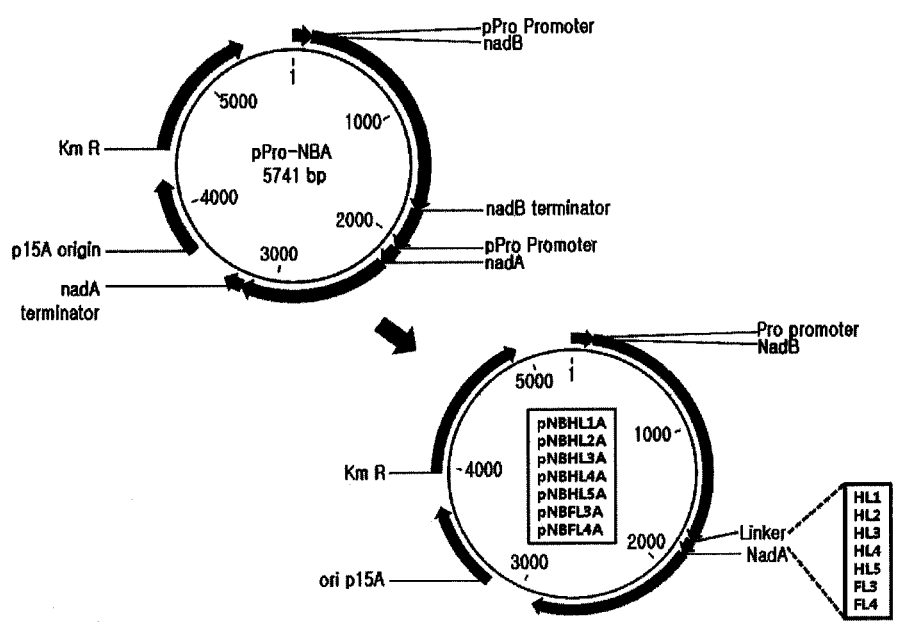
FIG. 2 shows a structure of pPro-NBA, pNBHL1A, pNBHL2A, pNBHL3A, pNBHL4A, pNBHL5A, pNBFL3A, or pNBFL4A plasmid.

Specifically, the recombinant vector may be a pNBHL1A, pNBHL2A, pNBHL3A, pNBHL4A, pNBHL5A, pNBFL3A or pNBFL4A plasmid vector which has a cleavage map of FIG. 2, and more specifically, the plasmid vector may include a nucleotide sequence of SEQ ID NO. 34, 35, 36, 37, 38, 39 or 40, respectively.

According to one specific embodiment, the quinolinic acid-producing microorganism may be a microorganism belonging to *Enterbacter* sp., *Escherichia* sp., *Erwinia* sp., *Serratia* sp., *Providencia* sp., *Corynebacterium* sp. or *Brevibacterium* sp. Specifically a microorganism belonging to *Escherichia* sp., and more specifically *E. coli*, but is not limited thereto.

The microorganism of the present invention may further be modified to weaken quinolinate phosphoribosyltransferase activity, compared to the endogenous activity thereof. Herein, the term "endogenous activity" means the activity of quinolinate phosphoribosyltransferase in a native microorganism.

The NadC has an activity to convert quinolinic acid into nicotinate mononucleotide, and may have an amino acid sequence of SEQ ID NO. 44 or an amino acid sequence having high homology therewith. The sequence of the gene nadC encoding this enzyme can be obtained from the genome sequence of *Escherichia coli* (GI: 89106990) as published in the literature (Mol Syst Biol. 2006; 2:2006.0007. Epub 2006 Feb. 21.), or the database available from NCBI or DDBJ.

[Activity of Quinolinate Phosphoribosyltransferase]

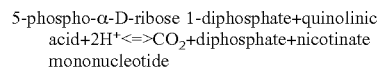

5-phospho-α-D-ribose 1-diphosphate+quinolinic acid+2H$^+$<=>CO$_2$+diphosphate+nicotinate mononucleotide Quinolinic acid can be accumulated in cells by weakening the NadC activity. The weakening of the enzyme activity can be achieved by a method selected from the group consisting of 1) partial or whole deletion of the gene encoding the enzyme, 2) modification of the expression control sequence to reduce expression of the gene (e.g., replacement of the endogenous promoter of the gene with a weak promoter), 3) modification of the gene sequence on the chromosome to weaken the enzyme activity, and 4) combinations thereof. In a specific Example of the present invention, nadC was removed from the genome of the microorganism by means of homologous recombination.

Further, the microorganism of the present invention can be further modified to enhance activities of one or more proteins selected from the group consisting of phosphoenolpyruvate carboxylase, L-aspartate aminotransferase and the fusion protein of the present invention, in order to enhance the biosynthetic pathway of L-aspartic acid from phosphoenolpyruvate.

The phosphoenolpyruvate carboxylase (PPC) and L-aspartate aminotransferase (AspC) has an activity to synthesize L-aspartic acid from phosphoenolpyruvate, and may have an amino acid sequence represented by SEQ ID NO. 45 or 46, or an amino acid sequence having high homology therewith, respectively. The sequence of the gene ppc or aspC encoding the enzyme can be obtained from the genome sequence of *Escherichia coli* (GI: 89110074, GI: 89107778) as published in the literature (Mol Syst Biol. 2006; 2:2006.0007. Epub 2006 Feb. 21.), or the database available from NCBI or DDBJ.

[Activity of Phosphoenolpyruvate Carboxylase]

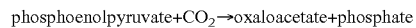

phosphoenolpyruvate+CO$_2$→oxaloacetate+phosphate

[Activity of L-aspartate Aminotransferase]

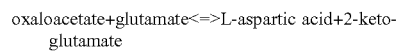

oxaloacetate+glutamate<=>L-aspartic acid+2-ketoglutamate

Therefore, if activities of PPC and AspC are enhanced, production of L-aspartic acid as a precursor of quinolinic acid in cells can be improved, thereby increasing production of quinolinic acid.

The enhancement of the enzyme activity can be achieved by a method selected from the group consisting of 1) a method of increasing the copy number of the gene encoding the enzyme, 2) a method of modifying the expression control sequence to increase expression of the gene, 3) a method of modifying the gene sequence on the chromosome to enhance the enzyme activity, and 4) combinations thereof. In a specific Example of the present invention, a plasmid comprising a gene encoding the enzyme was constructed, and introduced into a microorganism producing quinolinic acid, thereby increasing the copy number of the gene and inducing enhancement of the activity.

In order to enhance activity of the fusion protein, the endogenous promoter of the gene encoding the fusion protein can be substituted with a strong promoter, or a mutation can be introduced in the promoters to become stronger, or the copy number of the gene can be increased. As the strong promoter, pTac, pTrc, pPro, pR, pL, pCJ1, pCysK, etc., can be generally used.

In a specific Example of the present invention, the promoter of nadB and nadA were substituted with a constitutive promoter pPro (SEQ ID NO. 32) to construct the constitutive expressible nadB and nadA genes, which are not suppressed by NadR as the transcriptional repressor to suppress the expressions of nadB and nadA with intracellular NAD level, in the form of a plasmid, and the plasmids were then introduced into microorganisms to induce overexpression of aspartate oxidase and quinolinate synthase. In addition, in a specific Example of the present invention, the promoter of the gene encoding NadB-L-NadA was substituted with the pPro promoter to induce overexpression of NadB-L-NadA. In this regard, the pPro promoter is an example only for resistance to feedback inhibition and for enhancement of expression, and the promoter of the present invention is not limited thereto.

In still another aspect, the present invention provides a method for producing quinolinic acid, comprising (a) culturing a recombinant microorganism expressing a fusion protein of L-aspartate oxidase and quinolinate synthase linked via a linker in a medium comprising a carbon source; and (b) recovering quinolinic acid produced during the cultivation.

The recombinant microorganism can be cultured in a suitable culture medium under suitable culture conditions known in the art. Such cultivation procedures can be used by a person skilled in the art and are readily adjusted according to the selected microorganism. The cultivation methods include, but are not limited to, batch, continuous and fed-batch cultures. Various cultivation methods of microorganisms have been disclosed in, for example, "Biochemical Engineering" by James M. Lee, Prentice-Hall International Editions, pp 138-176.

The culture medium to be used must meet the requirements of the particular strains in a suitable manner.

Culture media for various microorganisms are published in the literature ("Manual of Methods for General Bacteriology" by the American Society for Bacteriology, Washington D.C., USA, 1981). The culture medium may comprise various carbon sources, nitrogen sources and microelements.

The carbon source available in the culture medium for microorganisms may comprise carbohydrates such as glucose, sucrose, lactose, fructose, maltose, starch and cellulose, oils such as soybean oil, sunflower oil, castor oil and coconut oil, fatty acids such as palmitic acid, stearic acid and linoleic acid, alcohols such as glycerol and ethanol, and organic acids such as acetic acid, but is not limited thereto. Those carbon sources may be used individually or in combination.

The nitrogen source available in the culture medium for microorganisms may comprise organic nitrogen sources such as peptones, yeast extract, meat extract, malt extract, corn steep liquor (CSL), soybean flour, and urea, or inorganic nitrogen sources such as ammonium sulfate, ammonium chloride, ammonium phosphate, ammonium carbonate and ammonium nitrate, but is not limited thereto. The nitrogen sources may be used individually or in combination.

The phosphorus source available in the culture medium for microorganisms may comprise potassium dihydrogen phosphate, dipotassium hydrogen phosphate or the corresponding sodium-containing salts. The culture medium may also comprise metal salts such as magnesium sulfate or iron sulfate. Amino acids, vitamins and suitable precursors may be comprised in the above-mentioned medium. The culture medium for microorganisms or individual components may be added to a batch or continuous batch, but is not limited there to.

Further, compounds such as ammonium hydroxide, potassium hydroxide, ammonia, phosphoric acid and sulfuric acid may be added to the culture medium for microorganism in a proper manner to control the pH value of the culture broth. An anti-foaming agent such as fatty acid polyglycol esters may be used during cultivation to suppress the development of foam. In order to maintain aerobic conditions, oxygen or oxygen-containing gas (e.g., air) may be introduced into the culture broth. The temperature of the culture broth may be normally from 20° C. to 45° C., and specifically from 25° C. to 40° C. The culture may be continued until the expectative amount of the quinolinic acid has produced, and preferably specifically 10 hours to 160 hours.

In a specific Example of the present invention, W3110ΔnadC strain, of which quinolinate phosphoribosyltransferase activity was eliminated, was transformed with expression plasmids comprising genes encoding NadB-L-NadA fusion proteins linked via various linkers, respectively and then the abilities of the strains were examined to produce quinolinic acid from aspartic acid. As a result, when L-aspartate oxidase and quinolinate synthase were expressed as a fusion protein, quinolinic acid can be produced in a high yield, compared to individual expressions of these enzymes (Table 2).

Further, E. coli having enhanced phosphoenolpyruvate carboxylase and L-aspartate aminotransferase activities and eliminated quinolinate phosphoribosyltransferase activity was transformed with the expression plasmid comprising the gene encoding the fusion protein, and then quinolinic acid productivities of these strains CV01-0600, CV01-0601, CV01-0602, CV01-0603, CV01-0604, CV01-0605, CV01-0606 and CV01-0607 were examined. As a result, it was found that quinolinic acid can be produced in a high yield by expression of the fusion protein of L-aspartate oxidase and quinolinate synthase, and quinolinic acid can be produced in a higher yield than the conventional strain, through elimination of quinolinate phosphoribosyltransferase activity and enhancement of phosphoenolpyruvate carboxylase and L-aspartate aminotransferase expressions, with expression of the fusion protein (Table 5).

The quinolinic acid-producing strains, *Escherichia coli* CV01-0604 and CV01-0605, were deposited under the Budapest Treaty at the Korean Culture Center of Microorganisms (KCCM, located on Hongjae 1-Dong, Seodaemun-Gu, Seoul, Korea) on Dec. 21, 2011 with Accession Nos. KCCM11235P and KCCM11236P, respectively. That is, this deposit is recognized by an International Depositary Authority under the Budapest Treaty.

Hereinafter, the present invention will be described in more detail with reference to Examples and Experimental Examples. However, these Examples are for illustrative purposes only, and the invention is not intended to be limited by these Examples.

Example 1

Preparation of the Stain Producing Quinolinic Acid

<1-1> Construction of Plasmid Expressing L-aspartate Oxidase

The gene nadB encoding L-aspartate oxidase was obtained through PCR using chromosomal DNA of *E. coli* W3110 as a template. Based on the nucleotide sequence for the nadB gene (NCBI Registration No. "GI: 89109380") of SEQ ID NO. 27 obtained from the GenBank of US National Institute of Health (NIH GenBank), the ORF region containing from ATG to TAA in nadB gene could be amplified, and primers of SEQ ID NOs. 1 and 2 having the recognition sites of restriction enzymes NdeI and BamHI were synthesized.

PCR was conducted using chromosomal DNA of *E. coli* W3110 as the template and oligonucleotides of SEQ ID NO. 1 and 2 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 2 minutes. Thus, amplified gene of about 1.9 kb, which contains nadB gene and the recognition sites of restriction enzymes NdeI and BamHI, was obtained.

The nadB gene obtained through the PCR procedures was treated with restriction enzymes NdeI and BamHI, and then was cloned by ligating into pProLar (CloneTech) vector treated with restriction enzymes NdeI and BamHI to ultimately construct a pPro-nadB recombinant vector into which the nadB gene, of which the expression was controlled under pPro promoter as the constitutive promoter, was cloned.

<1-2> Construction of Plasmid Expressing L-aspartate Oxidase and Quinolinate Synthase The gene nadA encoding quinolinate synthase was obtained through PCR using chromosomal DNA of *E. coli* W3110 as a template. Based on the base sequence for the nadA gene (NCBI Registration No. "GI: 89107601") of SEQ ID NO. 28 obtained from the GenBank of US National Institute of Health (NIH GenBank), the ORF region containing from ATG to TAA in nadA gene could be amplified, and primers of SEQ ID NOs. 3 and 4 having the recognition sites of restriction enzymes ApaI and NotI were synthesized.

PCR was conducted using chromosomal DNA of *E. coli* W3110 as the template and oligonucleotides of SEQ ID NOs. 3 and 4 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 2 minutes. Thus, amplified gene of about 1.0 kb, which contains nadA gene and the recognition sites of restriction enzymes ApaI and NotI was obtained.

In addition, Pro promoter was obtained through PCR using chromosomal DNA of pProLar (CloneTech) vector as a template. Based on the base sequence (SEQ ID NO. 32) for the Pro promoter from CloneTech, and primers of SEQ ID NOs. 5 and 6 having the recognition sites of restriction enzymes BamHI and ApaI were synthesized in order to ligate the pPro promoter and the amplified nadA gene.

PCR was conducted using chromosomal DNA of *E. coli* W3110 as the template and oligonucleotides of SEQ ID NOs. 5 and 6 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 1 minute. Thus, an amplified gene of about 0.135 kb, which contains the pPro promoter and the recognition sites of restriction enzymes BamHI and ApaI, was obtained.

The nadA gene obtained through the PCR procedures was treated with restriction enzymes ApaI and NotI, and amplified pPro promoter fragment was treated with ApaI and BamHI. The nadA and pPro promoter fragments treated with the restriction enzymes were cloned by ligating into the NotI and BamHI-treated pPro-nadB vector prepared in <Example 1-1> to ultimately construct a pPro-NBA recombinant vector of 5.7 Kb, into which the nadB gene, of which the expression was controlled under pPro promoter as the constitutive promoter, and the nadA gene of which the expression was controlled by pPro promoter, were cloned. The constructed pPro-NBA has the sequence of SEQ ID NO. 33. FIG. 2 shows the construction of pPro-NBA as the plasmid expressing genes encoding L-aspartate oxidase and quinolinate synthase.

<1-3> Construction of Plasmid Expressing NadB-L-NadA

In order to construct a plasmid expressing NadB-L-NadA containing a linker, PCR was conducted using pPro-NBA (SEQ ID NO. 33) prepared in <Example 1-2> as the template and oligonucleotides of SEQ ID NOs. 7 and 8 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 2 minutes. Thus, an amplified gene of about 1.8 kb, which contains the pPro promoter, the restriction enzyme site XhoI and the linker at the end of nadB gene, was obtained.

In addition, PCR was conducted using pPro-NBA as the template, and oligonucleotides of SEQ ID NOs. 15 and 16 as the primer, in order to amplify nadA gene fragment having the sequence homologous to the end of the amplified gene of about 1.8 kb, which contains the restriction enzyme site XhoI, the pPro promoter and the linker at the end of nadB gene, and the restriction enzyme site NotI at the end of nadA gene. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 2 minutes. Thus, the amplified gene of about 1.1 kb, which can be ligated with the linker by homologous ligation and contains the restriction enzyme site NotI at the end of nadA gene, was obtained.

The [amplified gene of about 1.8 kb containing the pPro promoter, the restriction enzyme site XhoI and the linker at the end of nadB gene] and the [nadA gene fragment having the sequence homologous to the and of the amplified gene of about 1.8 kb and the restriction enzyme site NotI at the end of nadA gene] thus prepared were mixed, and Sewing PCR was conducted. PfuUltra™ DNA polymerase (Stratagene) was used as the polymerase, and PCR was conducted by repeating the cycle 10 times including denaturation at 96° C. for 60 seconds, annealing at 50° C. for 60 seconds and extension at 72° C. for 1 minute. PCR was further conducted by adding oligonucleotides of SW ID NOs. 7 and 16 to the PCR reaction mixture. PfuUltra™ DNA polymerase (Stratagene) was used as the polymerase, and PCR was conducted by repeating the cycle 20 times including denaturation at 96° C. for 30 seconds, annealing at 50° C. for 30 seconds and extension at 72° C. for 3 minutes. Finally, amplified fusion protein gene of about 2.9 kb containing "restriction enzyme XhoI_pPro promoter_nadB_linker_nadA_restriction enzyme NotI" was obtained.

The gene fragment, "restriction enzyme XhoI_pPro promoter_nadB_linker_nadA_restriction enzyme NotI" obtained through PCR was treated with restriction enzymes, XhoI and NotI. The "pPro promoter_nadB_linker_nadA gene fragment" treated with the restriction enzymes was cloned by ligating into pProLar (CloneTech) vector treated with restriction enzymes, XhoI and NotI so as to ultimately construct a pNBHL1A recombinant vector, of which the expression was controlled under pPro promoter as the constitutive promoter, and into which the single fusion protein of nadB and nadA linked via the linker was cloned. The linkers used in the present Example are composed of 5 to 30 amino acids, and have amino acid sequences represented by SEQ ID NOs. 54, 55, 56, 57, 58, 59 and 60, respectively.

The nadB gene fragment was amplified by changing the oligonucleotide of SEQ ID NO. 8 containing the linker to the oligonucleotides of SEQ ID NOs. 9, 10, 11, 12, 13, or 14, so as to amplify various genes containing various linkers, each containing the pPro promoter and the linker at the end of nadB. In the same manner as above, pNBHL2A, pNBHL3A, pNBHL4A, pNBHL5A, pNBFL3A and pNBFL4A recombinant vectors were prepared. The prepared pNBHL1A, pNBHL2A, pNBHL3A, pNBHL4A, pNBHL5A, pNBFL3A and pNBFL4A have nucleotide sequences of SEQ ID NOs. 34, 35, 36, 37, 38, 39 and 40, respectively. The fusion proteins of L-aspartate oxidase and quinolinate synthase thus prepared have amino acid sequences of SEQ ID NOs. 47, 48, 49, 50, 51, 52 and 53, respectively. FIG. 2 shows the construction of pNBHL1A, pNBHL2A, pNBHL3A, pNBHL4A, pNBHL5A, pNBFL3A or pNBFL4A, which is a plasmid expressing each gene encoding fusion proteins of L-aspartate oxidase and quinolinate synthase linked via various linkers.

<1-4> Construction of Plasmid Expressing Phosphoenolpyruvate Carboxylase and L-aspartate Transaminase The gene ppc encoding phosphoenolpyruvate carboxylase was obtained through PCR using chromosomal DNA of *E. coli* W3110 as a template. Based on the base sequence for the ppc gene (NCBI Registration No. "GI: 89110074") of SEQ ID NO. 29 obtained from the GenBank of US National Institute of Health (NIH GenBank), the region from the promoter to the terminator in ppc gene could be amplified, and primers of SEQ ID NOs. 17 and 18 having the recognition sites of restriction enzymes HindIII and BamHI were synthesized.

PCR was conducted using chromosomal DNA of *E. coli* W3110 as the template and oligonucleotides of SEQ ID NOs. 17 and 18 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 4 minutes. Thus, amplified gene of about 3.1 kb, which contains ppc gene and the recognition sites of restriction enzymes HindIII and BamHI, was obtained.

The ppc gene obtained through the PCR procedures was treated with restriction enzymes HindIII and BamHI, and then cloned by ligating into pCL1920 (AB236930) vector treated with restriction enzymes HindIII and BamHI to ultimately construct a pCP recombinant vector into which the ppc gene was cloned.

To clone the aspC gene into the pCP recombinant vector into which the ppc gene was cloned, the gene aspC encoding L-aspartate transaminase was obtained through PCR using chromosomal DNA of *E. coli* W3110 as a template. Based on the base sequence for the aspC gene (NCBI Registration No. "GI: 89107778") of SEQ ID NO. 30 obtained from the GenBank of US National Institute of Health (NIH GenBank), the region from the promoter to the terminator in aspC gene could be amplified, and primers of SEQ ID NOs. 19 and 20 having the recognition sites of restriction enzymes BamHI and KpnI were synthesized.

PCR was conducted using chromosomal DNA of *E. coli* W3110 as a template and oligonucleotides of SEQ ID NOs. 19 and 20 as the primer. PfuUltra™ DNA polymerase (Stratagene) was used as the polymerase, and PCR was conducted by repeating the cycle 30 times including denaturation at 96° C. for 30 seconds, annealing at 50° C. for 30 seconds and extension at 72° C. for 2 minutes. Thus, amplified gene of about 1.5 kb, which contains aspC gene and the recognition sites of restriction enzymes BamHI and KpnI, was obtained.

Figure 3:
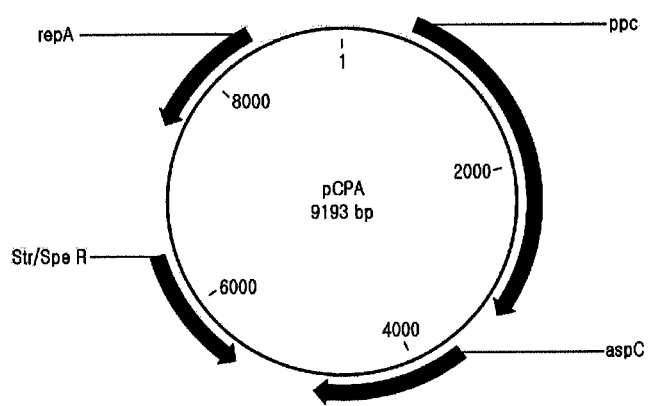
FIG. 3 shows a structure of pCPA which is a plasmid expressing genes encoding phosphoenolpyruvate carboxylase and L-aspartate aminotransferase.

The aspC gene obtained through the PCR was treated with restriction enzymes, BamHI and KpnI and then cloned by ligating into pCP vector treated with the restriction enzymes BamHI and KpnI to ultimately construct a pCPA recombinant vector into which aspC gene and ppc gene were cloned at the same time. The pCPA vector thus constructed has sequence of SEQ ID NO. 41. FIG. 3 shows the constructure of pCPA, which is a plasmid expressing the genes encoding phosphoenolpyruvate carboxylase and L-aspartate transaminase.

<1-5> Construction of Quinolinate Phosphoribosyltransferase-deficient Strain

In the present example, the nadC gene involved in the decomposition pathway of quinolinic acid was obtained through PCR using chromosomal DNA of *E. coli* W3110 as the template. Based on the base sequence information of the nadC gene (NCBI Registration No. "GI:89106990") obtained from the GenBank of US National Institute of Health (NIH GenBank), primers of SEQ ID NOs. 21 and 22 to amplify the downstream region of nadC gene, primers of SEQ ID NOs. 23 and 24 to amplify the upstream and downstream regions of nadC gene and loxpCm, and primers of SEQ ID NOs. 25 and 26 to amplify the upstream region of nadC gene, were synthesized.

PCR was conducted using chromosomal DNA of *E. coli* W3110 as the template and oligonucleotides of SEQ ID NOs. 21 and 22, and 25 and 26 as the primer to amplify the upstream and downstream regions of nadC gene of 0.5 kb and 0.3 kb, respectively. In addition, PCR was conducted using the pLoxpCat2 plasmid vector containing loxpCm as the template, and oligonucleotides of SEQ ID NOs. 23 and 24 as the primer to amplify loxpCm gene of 1.0 kb, which has the sequence homologous to nadC gene on both ends. PfuUltra™ DNA polymerase (Stratagene) was used as the polymerase, and PCR was conducted by repeating the cycle 30 times comprising denaturation at 96° C. for 30 seconds, annealing at 53° C. for 30 seconds and extension at 72° C. for 1 minute. Then, nadC-upstream fragment, nadC-downstream fragment, and loxpCm fragment obtained from the PCR reactions were used as template to conduct PCR under PCR conditions including 10 repetition of the cycle including denaturation at 96° C. for 60 seconds, annealing at 50° C. for 60 seconds and extension at 72° C. for 1 minute, and 20 repetition of the cycle after addition of primers of SEQ ID NOs. 21 and 26. Thus, a nadC deficient cassette of 1.8 kb, which contains the upstream region of nadC gene-loxpCm-downstream region of nadC gene, was obtained.

E. coli W3110 containing pKD46 as lambda red recombinase expression vector was transformed with the nadC deficient cassette by means of electroporation, and then the strain was smeared on LB (Luria-Bertani) plating medium (tryptone 10 g, yeast extract 5 g, NaCl 10 g, and agar 1.5%/L) containing chloramphenicol as the selective marker and incubated at 37° C. overnight to select microorganism strains displaying a resistance against chloramphenicol.

The selected strains as the template were directly subjected to PCR using primers of SEQ ID NO. 21 and 26 under the same conditions, and then the deletion of nadC gene was confirmed by identifying the gene size in wild strain and nadC-deficient strain to be 1.0 kb and 1.8 kb, respectively, on 1.0% agarose gel. In addition, nadC gene was also removed from E. coli W3110 as the wild strain according to the same method as above.

Example 2

Preparation and Evaluation of Fusion Protein-expressing Strain

<2-1> Preparation of Fusion Protein-Expressing Strain

The pNBHL1A, pNBHL2A, pNBHL3A, pNBHL4A, pNBHL5A, pNBFL3A and pNBFL4A and pPro-NBA plasmids expressing genes encoding the single fusion proteins which were prepared by linking L-aspartate oxidase and quinolinate synthase via various linkers of <Example 1-3> were used through $CaCl_2$ method to transform W3110ΔnadC strain as constructed in <Example 1-5>, which were then smeared on LB-Km plating medium (yeast extract 10 g/L, NaCl 5 g/L, tryptone 10 g/L, kanamycin 25 μg/L) and incubated at 37° C. overnight. Then, kanamycin-resistant colonies were selected. Therefore, strains expressing L-aspartate oxidase and quinolinate synthase as a single fusion protein were obtained.

<2-2> Comparison of Productivity of Quinolinic Acid from Aspartic Acid between Fusion Proteins having Various Linkers In order to compare the ability to synthesize quinolinic acid from aspartic acid between fusion proteins having various linkers, each of the fusion protein-expressing strains obtained in <Example 2-1> was inoculated in 5 ml of LB-Km-IPTG (yeast extract 10 g/L, NaCl 5 g/L, tryptone 10 g/L, kanamycin 25 μg/L, IPTG 10 mM) liquid medium in a 37° C. incubator, and cultured at 37° C. with 250 rpm overnight to obtain a culture broth. The culture broth thus obtained was centrifuged at 4000 rpm for 10 minutes to obtain only the fusion protein-expressing strain, which was resuspended in 500 μl of pH 7.0 Tris buffer and then disrupted by sonication.

The whole cell lysates containing the expressed-fusion protein obtained by the above method were used to compare the ability to synthesize quinolinic acid from L-aspartic acid through enzymatic reaction. Table 1 shows the composition of the enzyme reaction mixture for comparison of the ability to synthesize quinolinic acid from L-aspartic acid.

TABLE 1

| Composition of reaction mixture | Unit (ml) |
| --- | --- |
| 200 mM L-aspartic acid | 0.1 |
| 200 mM dihydroxyacetone phosphate | 0.1 |
| Cell lysate | 0.1 |
| 1M Tris buffer (pH 7.0) | 0.1 |
| Distilled water | 0.6 |
| Total | 1.0 |

The reaction composition was allowed to react at 37° C. for 30 minutes. L-aspartic acid and quinolinic acid in the culture broth were analyzed by HPLC. The analysis result is shown in Table 2, and indicates the ability of each fusion protein to produce quinolinic acid from L-aspartic acid.

TABLE 2

| Strain | Plasmid | Amino acid of linker | Quinolinic acid(g/L) | Yield (mole conversion rate % ※) |
| --- | --- | --- | --- | --- |
| W3110ΔnadC | pPro-NBA | | 1.5 | 44.9% |
| | pNBHL1A | LA(EAAAK)$_1$AAA (SEQ ID NO. 54) | 2.5 | 74.9% |
| | pNBHL2A | LA(EAAAK)$_2$AAA (SEQ ID NO. 55) | 2.4 | 71.9% |
| | pNBHL3A | LA(EAAAK)$_3$AAA (SEQ ID NO. 56) | 2.7 | 80.8% |
| | pNBHL4A | LA(EAAAK)$_4$AAA (SEQ ID NO. 57) | 3.1 | 92.8% |
| | pNBHL5A | LA(EAAAK)$_5$AAA (SEQ ID NO. 58) | 3.2 | 95.8% |
| | pNBFL3A | L(GGGS)$_3$AAA (SEQ ID NO. 59) | 2.4 | 71.9% |
| | pNBFL4A | L(GGGS)$_4$AAA (SEQ ID NO. 60) | 2.2 | 65.9% |

※ mole conversion rate (%) = produced quinolinic acid (M)/added L-aspartic acid (M)

pPro-NBA expressing each of L-aspartate oxidase and quinolinate synthase produced 1.5 g/L of quinolinic acid from L-aspartic acid, and showed 44.9% of enzymatic conversion yield from L-aspartic acid to quinolinic acid, whereas pNBHL1A, pNBHL2A, pNBHL3A, pNBHL4A, pNBHL5A, pNBFL3A and pNBFL4A producing the fusion proteins of L-aspartate oxidase and quinolinate synthase linked via various linkers produced 2.2~3.2 g/L of quinolinic acid, and showed 65.9~95.8% of enzymatic conversion yield from L-aspartic acid to quinolinic acid, respectively.

This result indicates that expression of a single fusion protein of L-aspartate oxidase and quinolinate synthase shows higher conversion yield of quinolinic acid, compared to expressions of individual enzymes. In addition, all the strains introduced with various types of linkers showed high enzymatic conversion rates, indicating that expression of the single fusion protein of L-aspartate oxidase and quinolinate synthase linked via the linker is more efficient in biosynthesis of quinolinic acid from L-aspartic acid. pNBHL4A and pNBHL5A introduced with the linker of LA(EAAAK)$_{4-5}$AAA showed the highest conversion rate to quinolinic acid, indicating that LA(EAAAK)$_{4-5}$AAA are the most efficient fusion protein linkers in the production of quinolinic acid.

Example 3

Preparation and Evaluation of Quinolinic Acid-producing Strain

<3-1> Preparation of Quinolinic Acid-producing Strain

In order to compare the ability to synthesize quinolinic acid from glucose between fusion proteins having various linkers, the pCPA plasmid constructed in <Example 1-4> was used through $CaCl_2$ method to transform W3110ΔnadC strain as constructed in <Example 1-5>, which were then smeared on LB-SP plating medium (yeast extract 10 g/L, NaCl 5 g/L, tryptone 10 g/L, spectinomycin 50 μg/L) and incubated at 37° C. overnight. Then, spectinomycin-resistant colonies were selected.

pPro-NBA, pNBHL1A, pNBHL2A, pNBHL3A, pNBHL4A, pNBHL5A, pNBFL3A and pNBFL4A plasmids constructed in <Example 1-2> and <Example 1-3> were used through $CaCl_2$ method to transform W3110ΔnadC strain containing pCPA constructed as above, which were then smeared on LB-Km-Sp plating medium (yeast extract 10 g/L, NaCl 5 g/L, tryptone 10 g/L, spectinomycin 50 μg/L, kanamycin 25 μg/L) and incubated at 37° C. overnight. Thereafter, each 10 of kanamycin and spectinomycin-resistant colonies were selected. The quinolinic acid-producing strains thus prepared were named as CV01-0600, CV01-0601, CV01-0602, CV01-0603, CV01-0604, CV01-0605, CV01-0606 and CV01-0607, respectively. Table 3 shows the genotype of host strain, the plasmid contained, and the amino acid sequence of the linker of fusion protein of L-aspartate oxidase and quinolinate synthase.

TABLE 3

| Genotype of strain | Plasmid | | Amino acid sequence of linker | Strain No. |
|---|---|---|---|---|
| W3110ΔnadC | pCPA | pPro-NBA | — | CV01-0600 |
| | | pNBHL1A | LA(EAAAK)$_1$AAA | CV01-0601 |
| | | pNBHL2A | LA(EAAAK)$_2$AAA | CV01-0602 |
| | | pNBHL3A | LA(EAAAK)$_3$AAA | CV01-0603 |
| | | pNBHL4A | LA(EAAAK)$_4$AAA | CV01-0604 |
| | | pNBHL5A | LA(EAAAK)$_5$AAA | CV01-0605 |
| | | pNBFL3A | L(GGGS)$_3$AAA | CV01-0606 |
| | | pNBFL4A | L(GGGS)$_4$AAA | CV01-0607 |

<3-2> Evaluation of Quinolinic Acid-producing Strain

In order to confirm the ability to produce quinolinic acid from glucose, quinolinic acid was titrated by the following experiment. The quinolinic acid-producing strain prepared in <Example 3-1> was cultured on LB-SP-Km plating medium in a 37° C. incubator overnight to obtain a single colony, which was then inoculated in 25 ml of quinolinic acid titer medium by 1 platinum loop and incubated with 250 rpm at 37° C. for 24 to 72 hours. Table 4 shows the composition of the production medium for quinolinic acid.

TABLE 4

| Composition | Conc. (per liter) |
|---|---|
| Glucose | 70 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |

Quinolinic acid in the culture broth was analyzed by HPLC. The result of analysis is shown in Table 5, and indicates the ability of the strain to produce quinolinic acid from glucose.

TABLE 5

| Strain | Quinolinic acid (g/L) | Yield (%)[x] |
|---|---|---|
| CV01-0600 | 5.5 | 7.9 |
| CV01-0601 | 7.0 | 10.0 |
| CV01-0602 | 6.5 | 9.3 |
| CV01-0603 | 7.5 | 10.7 |
| CV01-0604 | 9.7 | 13.9 |
| CV01-0605 | 10.3 | 14.7 |
| CV01-0606 | 6.5 | 9.3 |
| CV01-0607 | 6.0 | 8.6 |

[x]Yield (%) = produced quinolinic acid (g)/added glucose (g)

CV01-0600 strain, which was prepared by eliminating quinolinate phosphoribosyltransferase from E. coli W3110 to suppress decomposition of intracellular quinolinic acid by quinolinate phosphoribosyltransferase, and then by enhancing expressions of phosphoenolpyruvate carboxylase, L-aspartate aminotransferase and L-aspartate oxidase, quinolinate synthase, produced 5.5 g/L of quinolinic acid, whereas CV01-0601, CV01-0602, CV01-0603, CV01-0604, CV01-0605, CV01-0606 and CV01-0607 strains expressing the fusion proteins of L-aspartate oxidase and quinolinate synthase linked via various linkers produced 6.0~10.3 g/L of quinolinic acid, respectively.

This result is consistent with the result of enzymatic conversion from L-aspartic acid to quinolinic acid in <Example 2>, and also indicates that expression of L-aspartate oxidase and quinolinate synthase as the single fusion protein minimizes the side reaction of converting α-iminosuccinate into oxaloacetate by increasing the reaction of an unstable intermediate metabolite α-iminosuccinate with quinolinate synthase, thereby increasing production of quinolinic acid. In addition, all the strains introduced with various types of linkers showed relatively high productivity of quinolinic acid, indicating that expression of the single fusion protein of L-aspartate oxidase and quinolinate synthase linked via the linker is more efficient in biosynthesis of quinolinic acid.

Further, consistent with the result of <Example 2>, pNBHL4A and pNBHL5A, which were introduced with the linkers of LA(EAAAK)$_{4-5}$AAA, respectively, showed the highest productivity of quinolinic acid, indicating that LA(EAAAK)$_{4-5}$AAA are the most efficient fusion protein linkers in the production of quinolinic acid.

Furthermore, it was confirmed that when the L-aspartic acid biosynthetic pathway is enhanced with a combination of improved reaction rate by expression of the fusion protein of L-aspartate oxidase and quinolinate synthase, elimination of quinolinate phosphoribosyltransferase activity, and enhancement of phosphoenolpyruvate carboxylase and L-aspartate aminotransferase expressions, quinolinic acid can be produced with high efficiency, compared to the conventional strain.

EFFECT OF THE INVENTION

The present invention provides a microorganism expressing a fusion protein of L-aspartate oxidase and quinolinate synthase linked via a linker to minimize a natural decomposition reaction of α-iminosuccinate, which is a problem of the conventional biological production process, thereby producing quinolinic acid with high productivity.

What is claimed is:

1. A recombinant microorganism producing quinolinic acid, which expresses a fusion protein of L-aspartate oxidase and quinolinate synthase linked via a linker.

2. The recombinant microorganism according to claim 1, wherein L-aspartate oxidase and quinolinate synthase have amino acid sequences represented by SEQ ID NO. 42 and SEQ ID NO. 43, respectively.

3. The recombinant microorganism according to claim 1, wherein the linker is composed of 5 to 30 amino acids.

4. The recombinant microorganism according to claim 1, wherein the linker has an amino acid sequence of LA(E-AAAK)nAAA (n is an integer of 1 to 5) or L(GGGS)nAAA (n is an integer of 1 to 5).

5. The recombinant microorganism according to claim 1, wherein the linker has an amino acid sequence selected from the group consisting of SEQ ID NOs. 54, 55, 56, 57, 58, 59 and 60.

6. The recombinant microorganism according to claim 1, wherein the fusion protein has an amino acid sequence selected from the group consisting of SEQ ID NOs. 47, 48, 49, 50, 51, 52 and 53.

7. The recombinant microorganism according to claim 1, wherein the microorganism is selected from the group consisting of *Enterbacter* sp., *Escherichia* sp., *Erwinia* sp., *Serratia* sp., *Providencia* sp., *Corynebacterium* sp. and *Brevibacterium* sp.

8. The recombinant microorganism according to claim 1, wherein the microorganism is *E. coli*.

9. The recombinant microorganism according to claim 1, wherein the microorganism is identified by Accession No. KCCM11235P or KCCM11236P.

10. A method for producing quinolinic acid, comprising:
   (a) culturing a recombinant microorganism expressing a fusion protein of L-aspartate oxidase and quinolinate synthase linked via a linker in a medium comprising a carbon source; and
   (b) recovering quinolinic acid produced during the cultivation.

\* \* \* \* \*

SEQUENCE LISTING

<160> NUMBER OF SEQ ID NOS: 63

<210> SEQ ID NO 1
<211> LENGTH: 25
<212> TYPE: DNA
<213> ORGANISM: Artificial Sequence
<220> FEATURE:
<223> OTHER INFORMATION: primer for amplification of nadB

<400> SEQUENCE: 1
catatgaata ctctccctga acatt                                         25

<210> SEQ ID NO 2
<211> LENGTH: 28
<212> TYPE: DNA
<213> ORGANISM: Artificial Sequence
<220> FEATURE:
<223> OTHER INFORMATION: primer for amplification of nadB

<400> SEQUENCE: 2
ggatccctat accactacgc ttgatcac                                      28

<210> SEQ ID NO 3
<211> LENGTH: 27
<212> TYPE: DNA
<213> ORGANISM: Artificial Sequence
<220> FEATURE:
<223> OTHER INFORMATION: primer for amplification of nadA

<400> SEQUENCE: 3
gggcccatga gcgtaatgtt tgatcca                                       27

<210> SEQ ID NO 4
<211> LENGTH: 25
<212> TYPE: DNA
<213> ORGANISM: Artificial Sequence
<220> FEATURE:
<223> OTHER INFORMATION: primer for amplification of nadA

<400> SEQUENCE: 4
gcggccgctc gtgcctaccg cttcg                                         25

<210> SEQ ID NO 5
<211> LENGTH: 28
<212> TYPE: DNA

<213> ORGANISM: Artificial Sequence
<220> FEATURE:
<223> OTHER INFORMATION: primer for amplification of Pro promoter

<400> SEQUENCE: 5
ggatccctcg agcatagcat ttttatcc        28

<210> SEQ ID NO 6
<211> LENGTH: 23
<212> TYPE: DNA
<213> ORGANISM: Artificial Sequence
<220> FEATURE:
<223> OTHER INFORMATION: primer for amplification of Pro promoter

<400> SEQUENCE: 6
gggcccatgt acctttctcc tct        23

<210> SEQ ID NO 7
<211> LENGTH: 20
<212> TYPE: DNA
<213> ORGANISM: Artificial Sequence
<220> FEATURE:
<223> OTHER INFORMATION: primer for amplification of Pro promoter

<400> SEQUENCE: 7
ctcgagcata gcattttat        20

<210> SEQ ID NO 8
<211> LENGTH: 69
<212> TYPE: DNA
<213> ORGANISM: Artificial Sequence
<220> FEATURE:
<223> OTHER INFORMATION: primer for amplification of nadB gene with
      Helical linker (HL1)

<400> SEQUENCE: 8
aaacattacg ctcatctgca gggctgctgc cttcgcggct gcttctgcca ggattctgtt        60
tatgtaatg        69

<210> SEQ ID NO 9
<211> LENGTH: 84
<212> TYPE: DNA
<213> ORGANISM: Artificial Sequence
<220> FEATURE:
<223> OTHER INFORMATION: primer for amplification of nadB gene with
      Helical linker (HL2)

<400> SEQUENCE: 9
aaacattacg ctcatctgca gggctgctgc cttcgcggct gcttccttcg cggctgcttc        60
tgccaggatt ctgtttatgt aatg        84

<210> SEQ ID NO 10
<211> LENGTH: 99
<212> TYPE: DNA
<213> ORGANISM: Artificial Sequence
<220> FEATURE:
<223> OTHER INFORMATION: primer for amplification of nadB gene with
      Helical linker (HL3)

<400> SEQUENCE: 10
aaacattacg ctcatctgca gggctgctgc cttcgcggct gcttccttcg cggctgcttc        60
cttcgcggct gcttctgcca ggattctgtt tatgtaatg        99

<210> SEQ ID NO 11

```
<211> LENGTH: 114
<212> TYPE: DNA
<213> ORGANISM: Artificial Sequence
<220> FEATURE:
<223> OTHER INFORMATION: primer for amplification of nadB gene with
      Helical linker (HL4)

<400> SEQUENCE: 11
aaacattacg ctcatctgca gggctgctgc cttcgcggct gcttccttcg cggctgcttc    60
cttcgcggct gcttccttcg cggctgcttc tgccaggatt ctgtttatgt aatg         114

<210> SEQ ID NO 12
<211> LENGTH: 129
<212> TYPE: DNA
<213> ORGANISM: Artificial Sequence
<220> FEATURE:
<223> OTHER INFORMATION: primer for amplification of nadB gene with
      Helical linker (HL5)

<400> SEQUENCE: 12
aaacattacg ctcatctgca gggctgctgc cttcgcggct gcttccttcg cggctgcttc    60
cttcgcggct gcttccttcg cggctgcttc cttcgcggct gcttctgcca ggattctgtt   120
tatgtaatg                                                           129

<210> SEQ ID NO 13
<211> LENGTH: 87
<212> TYPE: DNA
<213> ORGANISM: Artificial Sequence
<220> FEATURE:
<223> OTHER INFORMATION: primer for amplification of nadB gene with
      Flexible linker(FL3)

<400> SEQUENCE: 13
aaacattacg ctcatctgca gggctgctgc gctaccacca ccgctaccac caccgctacc    60
accacccagg attctgttta tgtaatg                                        87

<210> SEQ ID NO 14
<211> LENGTH: 99
<212> TYPE: DNA
<213> ORGANISM: Artificial Sequence
<220> FEATURE:
<223> OTHER INFORMATION: primer for amplification of nadB gene with
      Flexible linker(FL4)

<400> SEQUENCE: 14
aaacattacg ctcatctgca gggctgctgc gctaccacca ccgctaccac caccgctacc    60
accaccgcta ccaccaccca ggattctgtt tatgtaatg                           99

<210> SEQ ID NO 15
<211> LENGTH: 43
<212> TYPE: DNA
<213> ORGANISM: Artificial Sequence
<220> FEATURE:
<223> OTHER INFORMATION: primer for amplification of nadA gene

<400> SEQUENCE: 15
ctgcagatga gcgtaatgtt tgatccagac acggcgattt atc                      43

<210> SEQ ID NO 16
<211> LENGTH: 23
<212> TYPE: DNA
<213> ORGANISM: Artificial Sequence
<220> FEATURE:
<223> OTHER INFORMATION: primer for amplification of nadA gene
```

<400> SEQUENCE: 16
attaattaat taagcggccg ctc                                        23

<210> SEQ ID NO 17
<211> LENGTH: 37
<212> TYPE: DNA
<213> ORGANISM: Artificial Sequence
<220> FEATURE:
<223> OTHER INFORMATION: primer for amplification of ppc gene

<400> SEQUENCE: 17
aagcttctgt aggccggata aggcgctcgc gccgcat                          37

<210> SEQ ID NO 18
<211> LENGTH: 27
<212> TYPE: DNA
<213> ORGANISM: Artificial Sequence
<220> FEATURE:
<223> OTHER INFORMATION: primer for amplification of ppc gene

<400> SEQUENCE: 18
cggatccttt gaataaaatg cagacag                                    27

<210> SEQ ID NO 19
<211> LENGTH: 26
<212> TYPE: DNA
<213> ORGANISM: Artificial Sequence
<220> FEATURE:
<223> OTHER INFORMATION: primer for amplification of aspC gene

<400> SEQUENCE: 19
ggatccgtcc acctatgttg actaca                                     26

<210> SEQ ID NO 20
<211> LENGTH: 31
<212> TYPE: DNA
<213> ORGANISM: Artificial Sequence
<220> FEATURE:
<223> OTHER INFORMATION: primer for amplification of aspC gene

<400> SEQUENCE: 20
ggtaccgagc tcataagcgt agcgcatcag g                               31

<210> SEQ ID NO 21
<211> LENGTH: 20
<212> TYPE: DNA
<213> ORGANISM: Artificial Sequence
<220> FEATURE:
<223> OTHER INFORMATION: primer for amplification of downstream region
      of nadC

<400> SEQUENCE: 21
gaaacgggaa agcagattcc                                            20

<210> SEQ ID NO 22
<211> LENGTH: 41
<212> TYPE: DNA
<213> ORGANISM: Artificial Sequence
<220> FEATURE:
<223> OTHER INFORMATION: primer for amplification of downstream region
      of nadC

<400> SEQUENCE: 22
cggtaggtac cgagctcgaa aagtagagaa tctggaagaa c                    41

<210> SEQ ID NO 23
<211> LENGTH: 41
<212> TYPE: DNA
<213> ORGANISM: Artificial Sequence
<220> FEATURE:
<223> OTHER INFORMATION: primer for amplificaiton of loxCm

<400> SEQUENCE: 23
gttcttccag attctctact tttcgagctc ggtacctacc g                41

<210> SEQ ID NO 24
<211> LENGTH: 42
<212> TYPE: DNA
<213> ORGANISM: Artificial Sequence
<220> FEATURE:
<223> OTHER INFORMATION: primer for amplification of loxpCm

<400> SEQUENCE: 24
tgaagaggtg tttattcaac tgggggtacc gttcgtataa tg               42

<210> SEQ ID NO 25
<211> LENGTH: 42
<212> TYPE: DNA
<213> ORGANISM: Artificial Sequence
<220> FEATURE:
<223> OTHER INFORMATION: primer for amplification of upstream region of
      nadC

<400> SEQUENCE: 25
cattatacga acggtacccc cagttgaata aacacctctt ca               42

<210> SEQ ID NO 26
<211> LENGTH: 19
<212> TYPE: DNA
<213> ORGANISM: Artificial Sequence
<220> FEATURE:
<223> OTHER INFORMATION: primer for amplification of upstream region of
      nadC

<400> SEQUENCE: 26
gtggtgctaa tacccggtt                                         19

<210> SEQ ID NO 27
<211> LENGTH: 1623
<212> TYPE: DNA
<213> ORGANISM: Escherichia coli
<220> FEATURE:
<221> NAME/KEY: gene
<222> LOCATION: (1)..(1623)
<223> OTHER INFORMATION: nadB ORF

<400> SEQUENCE: 27
atgaatactc tccctgaaca ttcatgtgac gtgttgatta tcggtagcgg cgcagccgga     60
ctttcactgg cgctacgcct ggctgaccag catcaggtca tcgttctaag taaaggcccg    120
gtaacggaag gttcaacatt ttatgcccag ggcggtattg ccgccgtgtt tgatgaaact    180
gacagcattg actcgcatgt ggaagacaca ttgattgccg gggctggtat ttgcgatcgc    240
catgcagttg aatttgtcgc cagcaatgca cgatcctgtg tgcaatggct aatcgaccag    300
ggggtgttgt ttgatacccca cattcaaccg aatggcgaag aaagttacca tctgacccgt    360
gaaggtggac atagtcaccg tcgtattctt catgccgccg acgccaccgg tagagaagta    420
gaaaccacgc tggtgagcaa ggcgctgaac catccgaata ttcgcgtgct ggagcgcagc    480
aacgcggttg atctgattgt ttctgacaaa attggcctgc cgggcacgcg acgggttgtt    540

```
ggcgcgtggg tatggaaccg taataaagaa acggtggaaa cctgccacgc aaaagcggtg      600
gtgctggcaa ccggcggtgc gtcgaaggtt tatcagtaca ccaccaatcc ggatatttct      660
tctggcgatg gcattgctat ggcgtggcgc gcaggctgcc gggttgccaa tctcgaattt      720
aatcagttcc accctaccgc gctatatcac ccacaggcac gcaatttcct gttaacagaa      780
gcactgcgcg gcgaaggcgc ttatctcaag cgcccggatg gtacgcgttt tatgcccgat      840
tttgatgagc gcggcgaact ggccccgcgc gatattgtcg cccgcgccat tgaccatgaa      900
atgaaacgcc tcggcgcaga ttgtatgttc cttgatatca gccataagcc cgccgatttt      960
attcgccagc atttcccgat gatttatgaa aagctgctcg gctggggat tgatctcaca     1020 caagaaccgg taccgattgt gcctgctgca cattatacct gcggtggtgt aatggttgat     1080
gatcatgggc gtacggacgt cgagggcttg tatgccattg gcgaggtgag ttataccggc     1140
ttacacggcg ctaaccgcat ggcctcgaat tcattgctgg agtgtctggt ctatggctgg     1200 tcggcggcg aagatatcac cagacgtatg ccttatgccc acgacatcag tacgttaccg     1260
ccgtgggatg aaagccgcgt tgagaaccct gacgaacggg tagtaattca gcataactgg     1320
cacgagctac gtctgtttat gtgggattac gttggcattg tgcgcacaac gaagcgcctg     1380
gaacgcgccc tgcggcggat aaccatgctc caacaagaaa tagacgaata ttacgcccat     1440
ttccgcgtct caaataattt gctggagctg cgtaatctgg tacaggttgc cgagttgatt     1500
gttcgctgtg caatgatgcg taaagagagt cggggggttgc atttcacgct ggattatccg     1560
gaactgctca cccattccgg tccgtcgatc ctttccccccg gcaatcatta cataaacaga     1620
taa                                                                   1623
```

<210> SEQ ID NO 28
<211> LENGTH: 1044
<212> TYPE: DNA
<213> ORGANISM: Escherichia coli
<220> FEATURE:
<221> NAME/KEY: gene
<222> LOCATION: (1)..(1044)
<223> OTHER INFORMATION: nadA ORF

<400> SEQUENCE: 28

```
atgagcgtaa tgtttgatcc agacacggcg atttatcctt ccccccgaa gccgacgccg       60 ttaagcattg atgaaaaagc gtattaccgc gagaagataa aacgtctgct aaaagaacgt      120
aatgcggtga tggttgccca ctactatacc gatcccgaaa ttcaacaact ggcagaagaa      180
accggtggct gtatttctga ttctctggaa atggcgcgct tcggtgcaaa gcatcccgct      240
tctactttgt tagtcgctgg ggtgagattt atgggagaaa ccgccaaaat tctcagtccg      300
gaaaaaacaa ttctgatgcc gacacttcag gctgaatgtt cactggatct cggctgccct      360
gttgaagaat ttaacgcatt tgcgatgcc catcccgatc gtactgtcgt cgtctacgcc      420
aacacttctg ctgcggtaaa agcgcgcgca gattgggtgg taacttcaag cattgccgtc      480
gaacttattg atcatcttga tagtttgggt gaaaaaatca tctgggcacc cgacaaacat      540
ctggggcgtt acgtgcaaaa acagacgggt ggagacattc tatgctggca gggtgcctgt      600
attgtgcatg atgaatttaa gactcaggcg ttaacccgct tgcaagaaga atacccggat      660
gctgccatac tggtgcatcc agaatcacca caagctattg tcgatatggc ggatgcggtc      720
ggttccacca gtcaactgat cgctgctgcg aaaacattgc cacatcagag gcttattgtg      780
gcaaccgatc ggggtatttt ctacaaaatg cagcaggcgg tgccagataa agagttactg      840
```

| | | |
|---|---|---|
| gaagcaccaa ccgcaggtga gggtgcaacc tgccgcagct gcgcgcattg tccgtggatg | | 900 |
| gccatgaatg gccttcaggc catcgcagag gcattagaac aggaaggaag caatcacgag | | 960 |
| gttcatgttg atgaaaggct gcgagagagg gcgctggtgc cgctcaatcg tatgctggat | | 1020 |
| tttgcggcta cactacgtgg ataa | | 1044 |

<210> SEQ ID NO 29
<211> LENGTH: 3096
<212> TYPE: DNA
<213> ORGANISM: Escherichia coli W3110
<220> FEATURE:
<221> NAME/KEY: gene
<222> LOCATION: (1)..(3096)
<223> OTHER INFORMATION: ppc

<400> SEQUENCE: 29

| | | |
|---|---|---|
| ataaggcgct cgcgccgcat ccggcactgt tgccaaactc cagtgccgca ataatgtcgg | | 60 |
| atgcgatact tgcgcatctt atccgaccta cacctttggt gttacttggg gcgatttttt | | 120 |
| aacatttcca taagttacgc ttatttaaag cgtcgtgaat ttaatgacgt aaattcctgc | | 180 |
| tatttattcg tttgctgaag cgatttcgca gcatttgacg tcaccgcttt tacgtggctt | | 240 |
| tataaaagac gacgaaaagc aaagcccgag catattcgcg ccaatgcgac gtgaaggata | | 300 |
| cagggctatc aaacgataag atggggtgtc tggggtaata tgaacgaaca atattccgca | | 360 |
| ttgcgtagta atgtcagtat gctcggcaaa gtgctgggag aaaccatcaa ggatgcgttg | | 420 |
| ggagaacaca ttcttgaacg cgtagaaact atccgtaagt tgtcgaaatc ttcacgcgct | | 480 |
| ggcaatgatg ctaaccgcca ggagttgctc accaccttac aaaatttgtc gaacgacgag | | 540 |
| ctgctgcccg ttgcgcgtgc gtttagtcag ttcctgaacc tggccaacac cgccgagcaa | | 600 |
| taccacagca tttcgccgaa aggcgaagct gccagcaacc cggaagtgat cgcccgcacc | | 660 |
| ctgcgtaaac tgaaaaacca gccggaactg agcgaagaca ccatcaaaaa agcagtggaa | | 720 |
| tcgctgtcgc tggaactggt cctcacggct caccccaaccg aaattaccccg tcgtacactg | | 780 |
| atccacaaaa tggtggaagt gaacgcctgt ttaaaacagc tcgataacaa agatatcgct | | 840 |
| gactacgaac acaaccagct gatgcgtcgc ctgcgccagt tgatcgccca gtcatggcat | | 900 |
| accgatgaaa tccgtaagct gcgtccaagc ccggtagatg aagccaaatg gggctttgcc | | 960 |
| gtagtggaaa acagcctgtg gcaaggcgta ccaaattacc tgcgcgaact gaacgaacaa | | 1020 |
| ctggaagaga acctcggcta caaactgccc gtcgaatttg ttccggtccg tttacttcg | | 1080 |
| tggatgggcg gcgaccgcga cggcaacccg aacgtcactg ccgatatcac ccgccacgtc | | 1140 |
| ctgctactca gccgctggaa agccaccgat ttgttcctga agatattca ggtgctggtt | | 1200 |
| tctgaactgt cgatggttga agcgaccccct gaactgctgg cgctggttgg cgaagaaggt | | 1260 |
| gccgcagaac cgtatcgcta tctgatgaaa aacctgcgtt ctcgcctgat ggcgacacag | | 1320 |
| gcatggctgg aagcgcgcct gaaaggcgaa gaactgccaa accagaaggg cctgctgaca | | 1380 |
| caaaacgaag aactgtggga accgctctac gcttgctacc agtcacttca ggcgtgtggc | | 1440 |
| atgggtatta tcgccaacgg cgatctgctc gacacccctgc gccgcgtgaa atgtttcggc | | 1500 |
| gtaccgctgg tccgtattga tatccgtcag gagagcacgc gtcataccga agcgctgggc | | 1560 |
| gagctgaccc gctacctcgg tatcggcgac tacgaaagct ggtcagaggc cgacaaacag | | 1620 |
| gcgttcctga tccgcgaact gaactccaaa cgtccgcttc tgccgcgcaa ctggcaacca | | 1680 |
| agcgccgaaa cgcgcgaagt gctcgatacc tgccaggtga ttgccgaagc accgcaaggc | | 1740 |
| tccattgccg cctacgtgat ctcgatggcg aaaacgccgt ccgacgtact ggctgtccac | | 1800 |

```
ctgctgctga aagaagcggg tatcgggttt gcgatgccgg ttgctccgct gtttgaaacc    1860
ctcgatgatc tgaacaacgc caacgatgtc atgacccagc tgctcaatat tgactggtat    1920
cgtggcctga ttcagggcaa acagatggtg atgattggct attccgactc agcaaaagat    1980
gcgggagtga tggcagcttc ctgggcgcaa tatcaggcac aggatgcatt aatcaaaacc    2040
tgcgaaaaag cgggtattga gctgacgttg ttccacggtc gcggcggttc cattggtcgc    2100
ggcggcgcac ctgctcatgc ggcgctgctg tcacaaccgc caggaagcct gaaaggcggc    2160
ctgcgcgtaa ccgaacaggg cgagatgatc cgctttaaat atggtctgcc agaaatcacc    2220
gtcagcagcc tgtcgcttta taccggggcg attctggaag ccaacctgct gccaccgccg    2280
gagccgaaag agagctggcg tcgcattatg gatgaactgt cagtcatctc ctgcgatgtc    2340
taccgcggct acgtacgtga aaacaaagat tttgtgcctt acttccgctc cgctacgccg    2400
gaacaagaac tgggcaaact gccgttgggt tcacgtccgg cgaaacgtcg cccaaccggc    2460
ggcgtcgagt cactacgcgc cattccgtgg atcttcgcct ggacgcaaaa ccgtctgatg    2520
ctccccgcct ggctgggtgc aggtacggcg ctgcaaaaag tggtcgaaga cggcaaacag    2580
agcgagctgg aggctatgtg ccgcgattgg ccattcttct cgacgcgtct cggcatgctg    2640
gagatggtct tcgccaaagc agacctgtgg ctggcggaat actatgacca acgcctggta    2700
gacaaagcac tgtggccgtt aggtaaagag ttacgcaacc tgcaagaaga agacatcaaa    2760
gtggtgctgg cgattgccaa cgattcccat ctgatggccg atctgccgtg gattgcagag    2820
tctattcagc tacggaatat ttacaccgac ccgctgaacg tattgcaggc cgagttgctg    2880
caccgctccc gccaggcaga aaaagaaggc caggaaccgg atcctcgcgt cgaacaagcg    2940
ttaatggtca ctattgccgg gattgcggca ggtatgcgta ataccggcta atcttcctct    3000
tctgcaaacc ctcgtgcttt tgcgcgaggg ttttctgaaa tacttctgtt ctaacaccct    3060
cgttttcaat atatttctgt ctgcatttta ttcaaa                              3096
```

<210> SEQ ID NO 30
<211> LENGTH: 1556
<212> TYPE: DNA
<213> ORGANISM: Escherichia coli W3110
<220> FEATURE:
<221> NAME/KEY: gene
<222> LOCATION: (1)..(1556)
<223> OTHER INFORMATION: aspC

<400> SEQUENCE: 30

```
gtccacctat gttgactaca tcatcaacca gatcgattct gacaacaaac tgggcgtagg     60
ttcagacgac accgttgctg tgggtatcgt ttaccagttc taatagcaca cctctttgtt    120
aaatgccgaa aaacaggac tttggtcctg ttttttttat accttccaga gcaatctcac    180
gtcttgcaaa aacagcctgc gttttcatca gtaatagttg aattttgta atctcccgt     240 taccctgata gcggacttcc cttctgtaac cataatggaa cctcgtcatg tttgagaaca    300
ttaccgccgc tcctgccgac ccgattctgg gcctggccga tctgtttcgt gccgatgaac    360
gtcccggcaa aattaacctc gggattggtg tctataaaga tgagacgggc aaaaccccgg    420
tactgaccag cgtgaaaaag gctgaacagt atctgctcga aaatgaaacc accaaaaatt    480
acctcggcat tgacggcatc cctgaatttg gtcgctgcac tcaggaactg ctgtttggta    540
aaggtagcgc cctgatcaat gacaaacgtg ctcgcacggc acagactccg ggggcactg    600 gcgcactacg cgtggctgcc gatttcctgg caaaaaatac cagcgttaag cgtgtgtggg    660
```

```
tgagcaaccc aagctggccg aaccataaga gcgtctttaa ctctgcaggt ctggaagttc      720
gtgaatacgc ttattatgat gcggaaaatc acactcttga cttcgatgca ctgattaaca      780
gcctgaatga agctcaggct ggcgacgtag tgctgttcca tggctgctgc cataacccaa      840
ccggtatcga ccctacgctg gaacaatggc aaacactggc acaactctcc gttgagaaag      900
gctggttacc gctgtttgac ttcgcttacc agggttttgc ccgtggtctg aagaagatg       960 ctgaaggact gcgcgctttc gcggctatgc ataaagagct gattgttgcc agttcctact     1020
ctaaaaactt tggcctgtac aacgagcgtg ttggcgcttg tactctggtt gctgccgaca     1080
gtgaaaccgt tgatcgcgca ttcagccaaa tgaaagcggc gattcgcgct aactactcta     1140
acccaccagc acacggcgct tctgttgttg ccaccatcct gagcaacgat gcgttacgtg     1200
cgatttggga acaagagctg actgatatgc cagcgtat tcagcgtatg cgtcagttgt       1260
tcgtcaatac gctgcaggaa aaaggcgcaa accgcgactt cagctttatc atcaaacaga     1320
acggcatgtt ctccttcagt ggcctgacaa agaacaagt gctgcgtctg cgcgaagagt      1380
ttggcgtata tgcggttgct tctggtcgcg taaatgtggc cggatgaca ccagataaca      1440 tggctccgct gtgcgaagcg attgtggcag tgctgtaagc attaaaaaca atgaagcccg     1500
ctgaaaagcg ggctgagact gatgacaaac gcaacattgc ctgatgcgct acgctt         1556
```

<210> SEQ ID NO 31
<211> LENGTH: 894
<212> TYPE: DNA
<213> ORGANISM: Escherichia coli W3110
<220> FEATURE:
<221> NAME/KEY: gene
<222> LOCATION: (1)..(894)
<223> OTHER INFORMATION: nadC ORF

<400> SEQUENCE: 31

```
atgccgcctc gccgctataa ccctgacacc cgacgtgacg agctgctgga acgcattaat       60
ctcgatatcc ccggcgcggt ggcccaggcg ctgcgggaag atttaggcgg aacagtcgat      120
gccaacaatg atattacggc aaaactttta ccggaaaatt ctcgctctca tgccacggtg      180
atcacccgcg agaatggcgt cttttgcggc aaacgctggg ttgaagaggt gtttattcaa      240
ctggcaggcg acgatgtcac cataatctgg catgtggatg acggcgatgt catcaatgcc      300
aatcaatcct tgttcgaact tgaaggccca tcccgcgtgc tgttaacggg cgaacgcact      360
gcgcttaatt ttgtgcaaac cctttcagga gttgccagta aggtacgcca ctatgtcgaa      420
ttgctggaag gcaccaacac gcagttgttg gatacgcgca aaaccttacc cggcctgcgt      480
tcagctctga atacgcggt actttgcggc ggcggagcga atcaccgtct ggggctttct      540
gatgccttcc tgatcaaaga aaccatatt attgcctccg gctcagtgcg ccaggcggtc      600
gaaaaagcgt cctggctgca cccggatgcg ccagtagaag tcgaagtaga gaatctggaa      660
gaacttgatg aagcccctgaa agcaggagcc gatatcatca tgctggataa cttcgaaaca      720
gaacagatgc gcgaagccgt caaacgcacc aacggcaagg cgctactgga agtgtctggc      780
aacgtcactg acaaaacact gcgtgaattt gccgaaacgg gcgtggactt tatctccgtc      840
ggtgcgctaa ctaaacacgt acaagcactc gacctttcaa tgcgttttcg ctaa            894
```

<210> SEQ ID NO 32
<211> LENGTH: 135
<212> TYPE: DNA
<213> ORGANISM: Artificial Sequence
<220> FEATURE:
<223> OTHER INFORMATION: Pro promoter

<400> SEQUENCE: 32

| | | | | | |
|---|---|---|---|---|---|
| ctcgagcata | gcatttttat | ccataagatt | agcggatcta | acctttacaa | ttgtgagcgc | 60 |
| tcacaattat | gatagattca | attgtgagcg | gataacaatt | tcacacagaa | ttcattaaag | 120 |
| aggagaaagg | tacat | | | | | 135 |

<210> SEQ ID NO 33
<211> LENGTH: 5741
<212> TYPE: DNA
<213> ORGANISM: Artificial Sequence
<220> FEATURE:
<223> OTHER INFORMATION: Plasmid vector (pPro-NBA)

<400> SEQUENCE: 33

| | | | | | |
|---|---|---|---|---|---|
| ctcgagcata | gcatttttat | ccataagatt | agcggatcta | acctttacaa | ttgtgagcgc | 60 |
| tcacaattat | gatagattca | attgtgagcg | gataacaatt | tcacacagaa | ttcattaaag | 120 |
| aggagaaagg | tacatatgaa | tactctccct | gaacattcat | gtgacgtgtt | gattatcggt | 180 |
| agcggcgcag | ccggactttc | actggcgcta | cgcctggctg | accagcatca | ggtcatcgtt | 240 |
| ctaagtaaag | gcccggtaac | ggaaggttca | acattttatg | cccagggcgg | tattgccgcc | 300 |
| gtgtttgatg | aaactgacag | cattgactcg | catgtggaag | acacattgat | tgccggggct | 360 |
| ggtatttgcg | atcgccatgc | agttgaattt | gtcgccagca | atgcacgatc | ctgtgtgcaa | 420 |
| tggctaatcg | accagggggt | gttgtttgat | acccacattc | aaccgaatgg | cgaagaaagt | 480 |
| taccatctga | cccgtgaagg | tggacatagt | caccgtcgta | ttcttcatgc | cgccgacgcc | 540 |
| accggtagag | aagtagaaac | cacgctggtg | agcaaggcgc | tgaaccatcc | gaatattcgc | 600 |
| gtgctggagc | gcagcaacgc | ggttgatctg | attgtttctg | acaaaattgg | cctgccgggc | 660 |
| acgcgacggg | ttgttggcgc | gtgggtatgg | aaccgtaata | agaaacggt | ggaaacctgc | 720 |
| cacgcaaaag | cggtggtgct | ggcaaccggc | ggtgcgtcga | aggtttatca | gtacaccacc | 780 |
| aatccggata | tttcttctgg | cgatggcatt | gctatggcgt | ggcgcgcagg | ctgccgggtt | 840 |
| gccaatctcg | aatttaatca | gttccaccct | accgcgctat | atcacccaca | ggcacgcaat | 900 |
| ttcctgttaa | cagaagcact | gcgcggcgaa | ggcgcttatc | tcaagcgccc | ggatggtacg | 960 |
| cgttttatgc | cgatttgga | tgagcgcggc | gaactggccc | cgcgcgatat | tgtcgcccgc | 1020 |
| gccattgacc | atgaaatgaa | acgcctcggc | gcagattgta | tgttccttga | tatcagccat | 1080 |
| aagcccgccg | attttattcg | ccagcatttc | ccgatgattt | atgaaaagct | gctcgggctg | 1140 |
| gggattgatc | tcacacaaga | accggtaccg | attgtgcctg | ctgcacatta | tacctgcggt | 1200 |
| ggtgtaatgg | ttgatgatca | tgggcgtacg | gacgtcgagg | gcttgtatgc | cattggcgag | 1260 |
| gtgagttata | ccggcttaca | cggcgctaac | cgcatggcct | cgaattcatt | gctggagtgt | 1320 |
| ctggtctatg | gctggtcggc | ggcggaagat | atcaccagac | gtatgcctta | tgcccacgac | 1380 |
| atcagtacgt | taccgccgtg | ggatgaaagc | gcgttgaga | accctgacga | acgggtagta | 1440 |
| attcagcata | actggcacga | gctacgtctg | tttatgtggg | attacgttgg | cattgtgcgc | 1500 |
| acaacgaagc | gcctggaacg | cgccctgcgg | cggataacca | tgctccaaca | agaaatagac | 1560 |
| gaatattacg | cccatttccg | cgtctcaaat | aatttgctgg | agctgcgtaa | tctggtacag | 1620 |
| gttgccgagt | tgattgttcg | ctgtgcaatg | atgcgtaaag | agagtcgggg | gttgcatttc | 1680 |
| acgctggatt | atccggaact | gctcacccat | tccggtccgt | cgatcctttc | ccccggcaat | 1740 |
| cattacataa | acagataaaa | agcctgggtc | agcgccgtat | acgcttcgga | atagttctgg | 1800 |

```
tctggcccac gaatgactaa gcgatcgcta aagcattctc ccgcctgcgg ggagaatgcc    1860
agcagcaccc gatgcggcag tcgcgcttcg ttttccgcca catccgtccg caaacgtaaa    1920
tgccagccca tgcttaatgc cagctccgta aaaccattac caatctgctc tggcagcact    1980
acgcagaaaa atccctcttc ggtaatgcac tccgccgcac aggtcagcaa cgatgggtga    2040
tcaagcgtag tggtataggg atccctcgag catagcattt ttatccataa gattagcgga    2100
tctaaccttt acaattgtga gcgctcacaa ttatgataga ttcaattgtg agcggataac    2160
aatttcacac agaattcatt aaagaggaga aggtacatg ggcccatgag cgtaatgttt     2220
gatccagaca cggcgattta tccttttccc ccgaagccga cgccgttaag cattgatgaa    2280
aaagcgtatt accgcgagaa gataaaacgt ctgctaaaag aacgtaatgc ggtgatggtt    2340
gcccactact ataccgatcc cgaaattcaa caactggcag aagaaaccgg tggctgtatt    2400
tctgattctc tggaaatggc gcgcttcggt gcaaagcatc ccgcttctac tttgttagtc    2460
gctggggtga gatttatggg agaaaccgcc aaaattctca gtccggaaaa aacaattctg    2520
atgccgacac ttcaggctga atgttcactg gatctcggct gccctgttga agaatttaac    2580
gcattttgcg atgcccatcc cgatcgtact gtcgtcgtct acgccaacac ttctgctgcg    2640
gtaaaagcgc gcgcagattg ggtggtaact tcaagcattg ccgtcgaact tattgatcat    2700
cttgatagtt tgggtgaaaa aatcatctgg gcacccgaca acatctgggg cgttacgtg    2760 caaaaacaga cgggtggaga cattctatgc tggcagggtg cctgtattgt gcatgatgaa    2820
tttaagactc aggcgttaac ccgcttgcaa gaagaatacc cggatgctgc atactggtg    2880 catccagaat caccacaagc tattgtcgat atggcggatg cggtcggttc caccagtcaa    2940
ctgatcgctg ctgcgaaaac attgccacat cagaggctta ttgtggcaac cgatcggggt    3000
attttctaca aaatgcagca ggcggtgcca gataaagagt tactggaagc accaaccgca    3060
ggtgagggtg caacctgccg cagctgcgcg cattgtccgt ggatggccat gaatggcctt    3120
caggccatcg cagaggcatt agaacaggaa ggaagcaatc acgaggttca tgttgatgaa    3180
aggctgcgag agagggcgct ggtgccgctc aatcgtatgc tggattttgc ggctacacta    3240
cgtggataac gaataataag gcgtaacgtt acgctttggg ggaaagatgg attttttag    3300 tgtgcagaat atcctggtac atataccaat aggggcaggc ggttatgatc tctcatggat    3360
cgaagcggta ggcacgagcg gccgcttaat taattaatct agaggcatca aataaaacga    3420
aaggctcagt cgaaagactg gcctttcgt tttatctgtt gtttgtcggt gaacgctctc     3480
ctgagtagga caaatccgcc gccctagacc tagggggatat attccgcttc ctcgctcact    3540
gactcgctac gctcggtcgt tcgactgcgg cgagcggaaa tggcttacga acggggcgga    3600
gatttcctgg aagatgccag gaagatactt aacaggaag tgagagggcc gcggcaaagc      3660 cgttttcca taggctccgc cccctgaca agcatcacga atctgacgc tcaaatcagt        3720 ggtggcgaaa cccgacagga ctataaagat accaggcgtt tccccctggc ggctccctcg    3780
tgcgctctcc tgttcctgcc tttcggttta ccggtgtcat tccgctgtta tggccgcgtt    3840
tgtctcattc cacgcctgac actcagttcc gggtaggcag ttcgctccaa gctggactgt    3900
atgcacgaac ccccgttca gtccgaccgc tgcgccttat ccgtaactat cgtcttgag      3960 tccaacccgg aaagacatgc aaaagcacca ctggcagcag ccactggtaa ttgatttaga    4020
ggagttagtc ttgaagtcat gcgccggtta aggctaaact gaaaggacaa gttttggtga    4080
ctgcgctcct ccaagccagt tacctcggtt caaagagttg gtagctcaga gaaccttcga    4140
aaaaccgccc tgcaaggcgg ttttttcgtt ttcagagcaa gagattacgc gcagaccaaa    4200
```

```
acgatctcaa gaagatcatc ttattaatca gataaaatat tactagattt cagtgcaatt      4260
tatctcttca aatgtagcac ctgaagtcag ccccatacga tataagttgt tactagtgct      4320
tggattctca ccaataaaaa acgcccggcg gcaaccgagc gttctgaaca aatccagatg      4380
gagttctgag gtcattactg gatctatcaa caggagtcca agcgagctct cgaaccccag      4440
agtcccgctc agaagaactc gtcaagaagg cgatagaagg cgatgcgctg cgaatcggga      4500
gcggcgatac cgtaaagcac gaggaagcgg tcagcccatt cgccgccaag ctcttcagca      4560
atatcacggg tagccaacgc tatgtcctga tagcggtccg ccacacccag ccggccacag      4620
tcgatgaatc cagaaaagcg gccattttcc accatgatat tcggcaagca ggcatcgcca      4680
tgggtcacga cgagatcctc gccgtcgggc atgcgcgcct tgagcctggc gaacagttcg      4740
gctggcgcga gcccctgatg ctcttcgtcc agatcatcct gatcgacaag accggcttcc      4800
atccgagtac gtgctcgctc gatgcgatgt ttcgcttggt ggtcgaatgg gcaggtagcc      4860
ggatcaagcg tatgcagccg ccgcattgca tcagccatga tggatacttt ctcggcagga      4920
gcaaggtgag atgacaggag atcctgcccc ggcacttcgc ccaatagcag ccagtccctt      4980
cccgcttcag tgacaacgtc gagcacagct gcgcaaggaa cgcccgtcgt ggccagccac      5040
gatagccgcg ctgcctcgtc ctgcagttca ttcagggcac cggacaggtc ggtcttgaca      5100
aaaagaaccg ggcgcccctg cgctgacagc cggaacacgg cggcatcaga gcagccgatt      5160
gtctgttgtg cccagtcata gccgaatagc ctctccaccc aagcggccgg agaacctgcg      5220
tgcaatccat cttgttcaat catgcgaaac gatcctcatc ctgtctcttg atcagatctt      5280 gatccctgc gccatcagat ccttggcggc aagaaagcca tccagtttac tttgcagggc      5340
ttcccaacct taccagaggg cgccccagct ggcaattccg acgtctgtgt ggaattctcg      5400
gacaccgagg agaatgtcaa gaggcgaaca cacaacgtct tggagcgcca gaggaggaac      5460
gagctaaaac ggagcttttt tgccctgcgt gaccagatcc cggagttgga aaacaatgaa      5520
aaggccccca aggtagttat cctttaaaaaa gccacagcat acatcctgtc cgtccaagca      5580
gaggagcaaa agctcatttc tgaagaggac ttgttgcgga aacgacgaga acagttgaaa      5640
cacaaacttg aacagctacg gaactcttgt gcgtaaggaa aagtaaggaa aacgattcct      5700
tctaacagaa atgtcctgag caatcaccta tgaactgtcg a                         5741
```

<210> SEQ ID NO 34
<211> LENGTH: 5226
<212> TYPE: DNA
<213> ORGANISM: Artificial Sequence
<220> FEATURE:
<223> OTHER INFORMATION: Plasmid vector (pNBHL1A)

<400> SEQUENCE: 34

```
ctcgagcata gcatttttat ccataagatt agcggatcta acctttacaa ttgtgagcgc        60
tcacaattat gatagattca attgtgagcg gataacaatt tcacacagaa ttcattaaag       120
aggagaaagg tacatatgaa tactctccct gaacattcat gtgacgtgtt gattatcggt       180
agcggcgcag ccggactttc actgcgcgcta cgcctggctg accagcatca ggtcatcgtt       240
ctaagtaaag gcccggtaac ggaaggttca acatttatg cccaggggcgg tattgccgcc       300 gtgtttgatg aaactgacag cattgactcg catgtggaag acacattgat tgccggggct       360
ggtatttgcg atcgccatgc agttgaattt gtcgccagca atgcacgatc ctgtgtgcaa       420
tggctaatcg accagggggt gttgtttgat acccacattc aaccgaatgg cgaagaaagt       480
```

```
taccatctga cccgtgaagg tggacatagt caccgtcgta ttcttcatgc cgccgacgcc    540
accggtagag aagtagaaac cacgctggtg agcaaggcgc tgaaccatcc gaatattcgc    600
gtgctggagc gcagcaacgc ggttgatctg attgtttctg acaaaattgg cctgccgggc    660
acgcgacggg ttgttggcgc gtgggtatgg aaccgtaata agaaacggt ggaaacctgc     720
cacgcaaaag cggtggtgct ggcaaccggc ggtgcgtcga aggtttatca gtacaccacc    780
aatccggata tttcttctgg cgatggcatt gctatggcgt ggcgcgcagg ctgccgggtt    840
gccaatctcg aatttaatca gttccaccct accgcgctat atcacccaca ggcacgcaat    900
ttcctgttaa cagaagcact gcgcggcgaa ggcgcttatc tcaagcgccc ggatggtacg    960
cgttttatgc ccgattttga tgagcgcggc gaactggccc cgcgcgatat tgtcgcccgc   1020
gccattgacc atgaaatgaa acgcctcggc gcagattgta tgttccttga tatcagccat   1080
aagcccgccg attttattcg ccagcatttc ccgatgattt atgaaaagct gctcgggctg   1140
gggattgatc tcacacaaga accggtaccg attgtgcctg ctgcacatta tacctgcggt   1200
ggtgtaatgg ttgatgatca tgggcgtacg gacgtcgagg gcttgtatgc cattggcgag   1260
gtgagttata ccggcttaca cggcgctaac cgcatggcct cgaattcatt gctggagtgt   1320
ctggtctatg gctggtcggc ggcggaagat atcaccagac gtatgcctta tgcccacgac   1380
atcagtacgt taccgccgtg ggatgaaagc cgcgttgaga accctgacga acgggtagta   1440
attcagcata actggcacga gctacgtctg tttatgtggg attacgttgg cattgtgcgc   1500
acaacgaagc gcctggaacg cgccctgcgg cggataacca tgctccaaca agaaatagac   1560
gaatattacg cccatttccg cgtctcaaat aatttgctgg agctgcgtaa tctggtacag   1620
gttgccgagt tgattgttcg ctgtgcaatg atgcgtaaag agagtcgggg gttgcatttc   1680
acgctggatt atccggaact gctcacccat tccggtccgt cgatcctttc ccccggcaat   1740
cattacataa acagaatcct ggcagaagca gccgcgaagg cagcagccct gcagatgagc   1800
gtaatgtttg atccagacac ggcgatttat ccttttcccc cgaagccgac gccgttaagc   1860
attgatgaaa aagcgtatta ccgcgagaag ataaaacgtc tgctaaaaga acgtaatgcg   1920
gtgatggttg cccactacta taccgatccc gaaattcaac aactggcaga agaaaccggt   1980
ggctgtatt ctgattctct ggaaatggcg cgcttcggtg caaagcatcc cgcttctact    2040
ttgttagtcg ctggggtgag atttatggga gaaaccgcca aaattctcag tccggaaaaa   2100
acaattctga tgccgacact tcaggctgaa tgttcactgg atctcggctg ccctgttgaa   2160
gaatttaacg cattttgcga tgcccatccc gatcgtactg tcgtcgtcta cgccaacact   2220
tctgctgcgg taaaagcgcg cgcagattgg gtggtaactt caagcattgc cgtcgaactt   2280
attgatcatc ttgatagttt gggtgaaaaa atcatctggg cacccgacaa acatctgggg   2340
cgttacgtgc aaaaacagac gggtggagac attctatgct ggcagggtgc ctgtattgtg   2400
catgatgaat ttaagactca ggcgttaacc cgcttgcaag aagaataccc ggatgctgcc   2460
atactggtgc atccagaatc accacaagct attgtcgata tggcggatgc ggtcggttcc   2520
accagtcaac tgatcgctgc tgcgaaaaca ttgccacatc agaggcttat tgtggcaacc   2580
gatcggggta ttttctacaa aatgcagcag gcggtgccag ataaagagtt actggaagca   2640
ccaaccgcag gtgagggtgc aacctgccgc agctgcgcgc attgtccgtg gatggccatg   2700
aatggccttc aggccatcgc agaggcatta gaacaggaag gaagcaatca cgaggttcat   2760
gttgatgaaa ggctgcgaga gagggcgctg gtgccgctca atcgtatgct ggattttgcg   2820
gctacactac gtggataacc cgggggatcc actagttcta gagcggccgc ttaattaatt   2880
```

```
aatctagagg catcaaataa aacgaaaggc tcagtcgaaa gactgggcct ttcgttttat   2940
ctgttgtttg tcggtgaacg ctctcctgag taggacaaat ccgccgccct agacctaggg   3000
gatatattcc gcttcctcgc tcactgactc gctacgctcg gtcgttcgac tgcggcgagc   3060
ggaaatggct tacgaacggg gcggagattt cctggaagat gccaggaaga tacttaacag   3120
ggaagtgaga gggccgcggc aaagccgttt tccataggc ccgccccc tgacaagcat      3180 cacgaaatct gacgctcaaa tcagtggtgg cgaaacccga caggactata agataccag    3240 gcgtttcccc ctggcggctc cctcgtgcgc tctcctgttc ctgcctttcg gtttaccggt   3300
gtcattccgc tgttatggcc gcgtttgtct cattccacgc tgacactca gttccgggta    3360 ggcagttcgc tccaagctgg actgtatgca cgaaccccc gttcagtccg accgctgcgc    3420
cttatccggt aactatcgtc ttgagtccaa cccggaaaga catgcaaaag caccactggc   3480
agcagccact ggtaattgat ttagaggagt tagtcttgaa gtcatgcgcc ggttaaggct   3540
aaactgaaag acaagttttt ggtgactgcg ctcctccaag ccagttacct cggttcaaag   3600
agttggtagc tcagagaacc ttcgaaaaac cgccctgcaa ggcggttttt tcgttttcag   3660
agcaagagat tacgcgcaga ccaaaacgat ctcaagaaga tcatcttatt aatcagataa   3720
aatattacta gatttcagtg caatttatct cttcaaatgt agcacctgaa gtcagcccca   3780
tacgatataa gttgttacta gtgcttggat tctcaccaat aaaaaacgcc cggcggcaac   3840
cgagcgttct gaacaaatcc agatggagtt ctgaggtcat tactggatct atcaacagga   3900
gtccaagcga gctctcgaac cccagagtcc cgctcagaag aactcgtcaa gaaggcgata   3960
gaaggcgatg cgctgcgaat cgggagcggc gataccgtaa agcacgagga agcggtcagc   4020
ccattcgccg ccaagctctt cagcaatatc acgggtagcc aacgctatgt cctgatagcg   4080
gtccgccaca cccagccggc cacagtcgat gaatccagaa aagcggccat tttccaccat   4140
gatattcggc aagcaggcat cgccatgggt cacgacgaga tcctcgccgt cgggcatgcg   4200
cgccttgagc ctggcgaaca gttcggctgg cgcgagcccc tgatgctctt cgtccagatc   4260
atcctgatcg acaagaccgg cttccatccg agtacgtgct cgctcgatgc gatgtttcgc   4320
ttggtggtcg aatgggcagg tagccggatc aagcgtatgc agccgccgca ttgcatcagc   4380
catgatggat actttctcgg caggagcaag gtgagatgac aggagatcct gccccggcac   4440
ttcgcccaat agcagccagt cccttcccgc ttcagtgaca acgtcgagca cagctgcgca   4500
aggaacgccc gtcgtggcca gccacgatag ccgcgctgcc tcgtcctgca gttcattcag   4560
ggcaccggac aggtcggtct tgacaaaaag aaccgggcgc cctgcgctg acagccggaa    4620 cacggcggca tcagagcagc cgattgtctg ttgtgcccag tcatagccga atagcctctc   4680
cacccaagcg gccggagaac ctgcgtgcaa tccatcttgt tcaatcatgc gaaacgatcc   4740
tcatcctgtc tcttgatcag atcttgatcc cctgcgccat cagatccttg gcggcaagaa   4800
agccatccag tttactttgc agggcttccc aaccttacca gagggcgccc cagctggcaa   4860
ttccgacgtc tgtgtggaat tctcggacac cgaggagaat gtcaagaggc gaacacacaa   4920
cgtcttggag cgccagagga ggaacgagct aaaacggagc ttttttgccc tgcgtgacca   4980
gatcccggag ttgaaaaaca atgaaaaggc ccccaaggta gttatcctta aaaaagccac   5040
agcatacatc ctgtccgtcc aagcagagga gcaaaagctc atttctgaag aggacttgtt   5100
gcggaaacga cgagaacagt tgaaacacaa acttgaacag ctacgaaact cttgtgcgta   5160
aggaaaagta aggaaaacga ttccttctaa cagaaatgtc ctgagcaatc acctatgaac   5220
``` tgtcga                                                                      5226

<210> SEQ ID NO 35
<211> LENGTH: 5241
<212> TYPE: DNA
<213> ORGANISM: Artificial Sequence
<220> FEATURE:
<223> OTHER INFORMATION: Plasmid vector (pNBHL2A)

<400> SEQUENCE: 35

| | | |
|---|---|---|
| ctcgagcata gcatttttat ccataagatt agcggatcta acctttacaa ttgtgagcgc | 60 |
| tcacaattat gatagattca attgtgagcg gataacaatt tcacacagaa ttcattaaag | 120 |
| aggagaaagg tacatatgaa tactctccct gaacattcat gtgacgtgtt gattatcggt | 180 |
| agcggcgcag ccggactttc actggcgcta cgcctggctg accagcatca ggtcatcgtt | 240 |
| ctaagtaaag gcccggtaac ggaaggttca acattttatg cccagggcgg tattgccgcc | 300 |
| gtgtttgatg aaactgacag cattgactcg catgtggaag acacattgat tgccggggct | 360 |
| ggtatttgcg atcgccatgc agttgaattt gtcgccagca tgcacgatc ctgtgtgcaa | 420 |
| tggctaatcg accagggggt gttgtttgat acccacattc aaccgaatgg cgaagaaagt | 480 |
| taccatctga cccgtgaagg tggacatagt caccgtcgta ttcttcatgc cgccgacgcc | 540 |
| accggtagag aagtagaaac cacgctggtg agcaaggcgc tgaaccatcc gaatattcgc | 600 |
| gtgctggagc gcagcaacgc ggttgatctg attgtttctg acaaaattgg cctgccgggc | 660 |
| acgcgacggg ttgttggcgc gtgggtatgg aaccgtaata agaaacggt ggaaacctgc | 720 |
| cacgcaaaag cggtggtgct ggcaaccggc ggtgcgtcga aggtttatca gtacaccacc | 780 |
| aatccggata tttcttctgg cgatggcatt gctatggcgt ggcgcgcagg ctgccgggtt | 840 |
| gccaatctcg aatttaatca gttccaccct accgcgctat atcacccaca ggcacgcaat | 900 |
| ttcctgttaa cagaagcact gcgcggcgaa ggcgcttatc tcaagcgccc ggatggtacg | 960 |
| cgttttatgc ccgattttga tgagcgcggc gaactggccc cgcgcgatat tgtcgcccgc | 1020 |
| gccattgacc atgaaatgaa acgcctcggc gcagattgta tgttccttga tatcagccat | 1080 |
| aagcccgccg atttattcg ccagcatttc ccgatgattt atgaaaagct gctcgggctg | 1140 |
| gggattgatc tcacacaaga accggtaccg attgtgcctg ctgcacatta tacctgcggt | 1200 |
| ggtgtaatgg ttgatgatca tgggcgtacg gacgtcgagg gcttgtatgc cattggcgag | 1260 |
| gtgagttata ccggcttaca cggcgctaac cgcatggcct cgaattcatt gctggagtgt | 1320 |
| ctggtctatg gctggtcggc ggcggaagat atcaccagac gtatgccta tgcccacgac | 1380 |
| atcagtacgt taccgccgtg ggatgaaagc gcgttgaga accctgacga acgggtagta | 1440 |
| attcagcata actggcacga gctacgtctg tttatgtggg attacgttgg cattgtgcgc | 1500 |
| acaacgaagc gcctggaacg cgccctgcgg cggataacca tgctccaaca agaaatagac | 1560 |
| gaatattacg cccatttccg cgtctcaaat aatttgctgg agctgcgtaa tctggtacag | 1620 |
| gttgccgagt tgattgttcg ctgtgcaatg atgcgtaaag agagtcgggg gttgcatttc | 1680 |
| acgctggatt atccggaact gctcacccat tccggtccgt cgatccttc ccccggcaat | 1740 |
| cattacataa acagaatcct ggcagaagca gccgcgaagg aagcagccgc gaaggcagca | 1800 |
| gccctgcaga tgagcgtaat gtttgatcca gacacggcga tttatccttt cccccgaag | 1860 |
| ccgacgccgt taagcattga tgaaaaagcg tattaccgcg agaagataaa acgtctgcta | 1920 |
| aaagaacgta atgcggtgat ggttgcccac tactataccg atcccgaaat tcaacaactg | 1980 |
| gcagaagaaa ccggtggctg tatttctgat tctctggaaa tggcgcgctt cggtgcaaag | 2040 |

```
catcccgctt ctactttgtt agtcgctggg gtgagattta tgggagaaac cgccaaaatt    2100
ctcagtccgg aaaaaacaat tctgatgccg acacttcagg ctgaatgttc actggatctc    2160
ggctgccctg ttgaagaatt taacgcattt tgcgatgccc atcccgatcg tactgtcgtc    2220
gtctacgcca acacttctgc tgcggtaaaa gcgcgcgcag attgggtggt aacttcaagc    2280
attgccgtcg aacttattga tcatcttgat agtttgggtg aaaaaatcat ctgggcaccc    2340
gacaaacatc tggggcgtta cgtgcaaaaa cagacgggtg gagacattct atgctggcag    2400
ggtgcctgta ttgtgcatga tgaatttaag actcaggcgt taacccgctt gcaagaagaa    2460
tacccggatg ctgccatact ggtgcatcca gaatcaccac aagctattgt cgatatggcg    2520
gatgcggtcg gttccaccag tcaactgatc gctgctgcga aaacattgcc acatcagagg    2580
cttattgtgg caaccgatcg gggtatttcc tacaaaatgc agcaggcggt gccagataaa    2640
gagttactgg aagcaccaac cgcaggtgag ggtgcaacct gccgcagctg cgcgcattgt    2700
ccgtggatgg ccatgaatgg ccttcaggcc atcgcagagg cattagaaca ggaaggaagc    2760
aatcacgagg ttcatgttga tgaaaggctg cgagagaggg cgctggtgcc gctcaatcgt    2820
atgctggatt ttgcggctac actacgtgga taacccgggg gatccactag ttctagagcg    2880
gccgcttaat taattaatct agaggcatca aataaaacga aaggctcagt cgaaagactg    2940
ggcctttcgt tttatctgtt gtttgtcggt gaacgctctc ctgagtagga caaatccgcc    3000
gccctagacc tagggggatat attccgcttc ctcgctcact gactcgctac gctcggtcgt    3060
tcgactgcgg cgagcggaaa tggcttacga acggggcgga gatttcctgg aagatgccag    3120
gaagatactt aacagggaag tgagagggcc gcggcaaagc cgttttttcca taggctccgc    3180 cccccctgaca agcatcacga aatctgacgc tcaaatcagt ggtggcgaaa cccgacagga    3240
ctataaagat accaggcgtt tccccctggc ggctccctcg tgcgctctcc tgttcctgcc    3300
tttcggttta ccggtgtcat tccgctgtta tggccgcgtt tgtctcattc cacgcctgac    3360
actcagttcc gggtaggcag ttcgctccaa gctggactgt atgcacgaac cccccgttca    3420
gtccgaccgc tgcgccttat ccggtaacta tcgtcttgag tccaacccgg aaagacatgc    3480
aaaagcacca ctggcagcag ccactggtaa ttgatttaga ggagttagtc ttgaagtcat    3540
gcgccggtta aggctaaact gaaaggacaa gttttggtga ctgcgctcct ccaagccagt    3600
tacctcggtt caaagagttg gtagctcaga gaaccttcga aaaaccgccc tgcaaggcgg    3660
ttttttcgtt ttcagagcaa gagattacgc gcagaccaaa cgatctcaa gaagatcatc    3720 ttattaatca gataaaatat tactagattt cagtgcaatt tatctcttca aatgtagcac    3780
ctgaagtcag ccccatacga tataagttgt tactagtgct tggattctca ccaataaaaa    3840
acgcccggcg gcaaccgagc gttctgaaca aatccgatcg gagttctgag gtcattactg    3900
gatctatcaa caggagtcca agcgagctct cgaacccag agtcccgctc agaagaactc    3960
gtcaagaagg cgatagaagg cgatgcgctg cgaatcggga gcggcgatac cgtaaagcac    4020
gaggaagcgg tcagcccatt cgccgccaag ctcttcagca atatcacggg tagccaacgc    4080
tatgtcctga tagcggtccg ccacacccag ccggccacag tcgatgaatc cagaaaagcg    4140
gccattttcc accatgatat tcggcaagca ggcatcgcca tgggtcacga cgagatcctc    4200
gccgtcgggc atgcgcgcct tgagcctggc gaacagttcg gctggcgcga gccctgatg    4260 ctcttcgtcc agatcatcct gatcgacaag accggcttcc atccgagtac gtgctcgctc    4320
gatgcgatgt ttcgcttggt ggtcgaatgg gcaggtagcc ggatcaagcg tatgcagccg    4380
```

```
ccgcattgca tcagccatga tggatacttt ctcggcagga gcaaggtgag atgacaggag    4440
atcctgcccc ggcacttcgc ccaatagcag ccagtccctt cccgcttcag tgacaacgtc    4500
gagcacagct gcgcaaggaa cgcccgtcgt ggccagccac gatagccgcg ctgcctcgtc    4560
ctgcagttca ttcagggcac cggacaggtc ggtcttgaca aaaagaaccg ggcgcccctg    4620
cgctgacagc cggaacacgg cggcatcaga gcagccgatt gtctgttgtg cccagtcata    4680
gccgaatagc ctctccaccc aagcggccgg agaacctgcg tgcaatccat cttgttcaat    4740
catgcgaaac gatcctcatc ctgtctcttg atcagatctt gatccctgc gccatcagat     4800 ccttggcggc aagaaagcca tccagtttac tttgcagggc ttcccaacct taccagaggg    4860
cgccccagct ggcaattccg acgtctgtgt ggaattctcg gacaccgagg agaatgtcaa    4920
gaggcgaaca cacaacgtct ggagcgcca gaggaggaac gagctaaaac ggagcttttt     4980
tgccctgcgt gaccagatcc cggagttgga aaacaatgaa aaggccccca aggtagttat    5040
ccttaaaaaa gccacagcat acatcctgtc cgtccaagca gaggagcaaa agctcatttc    5100
tgaagaggac ttgttgcgga aacgacgaga acagttgaaa cacaaacttg aacagctacg    5160
gaactcttgt gcgtaaggaa aagtaaggaa aacgattcct tctaacagaa atgtcctgag    5220
caatcaccta tgaactgtcg a                                              5241
```

<210> SEQ ID NO 36
<211> LENGTH: 5256
<212> TYPE: DNA
<213> ORGANISM: Artificial Sequence
<220> FEATURE:
<223> OTHER INFORMATION: Plasmid vector (pNBHL3A)

<400> SEQUENCE: 36

```
ctcgagcata gcatttttat ccataagatt agcggatcta acctttacaa ttgtgagcgc      60
tcacaattat gatagattca attgtgagcg gataacaatt tcacacagaa ttcattaaag     120
aggagaaagg tacatatgaa tactctccct gaacattcat gtgacgtgtt gattatcggt     180
agcggcgcag ccggactttc actggcgcta cgcctggctg accagcatca ggtcatcgtt     240
ctaagtaaag gcccggtaac ggaaggttca acattttatg cccagggcgg tattgccgcc     300
gtgtttgatg aaactgacag cattgactcg catgtggaag acacattgat tgccggggct     360
ggtatttgcg atcgccatgc agttgaattt gtcgccagca atgcacgatc ctgtgtgcaa     420
tggctaatcg accagggggt gttgtttgat acccacattc aaccgaatgg cgaagaaagt     480
taccatctga cccgtgaagg tggacatagt caccgtcgta ttcttcatgc cgccgacgcc     540
accggtagag aagtagaaac cacgctggtg agcaaggcgc tgaaccatcc gaatattcgc     600
gtgctggagc gcagcaacgc ggttgatctg attgtttctg acaaaattgg cctgccgggc     660
acgcgacggg ttgttggcgc gtgggtatgg aaccgtaata agaaacggt ggaaacctgc      720 cacgcaaaag cggtggtgct ggcaaccggc ggtgcgtcga aggtttatca gtacaccacc     780
aatccggata tttcttctgg cgatggcatt gctatggcgt ggcgcgcagg ctgccgggtt     840
gccaatctcg aatttaatca gttccaccct accgcgctat atcacccaca ggcacgcaat     900
ttcctgttaa cagaagcact gcgcggcgaa ggcgcttatc tcaagcgccc ggatggtacg     960
cgttttatgc ccgattttga tgagcgcggc gaactggccc cgcgcgatat tgtcgcccgc    1020
gccattgacc atgaaatgaa acgcctcggc gcagattgta tgttccttga tatcagccat    1080
aagcccgccg attttattcg ccagcatttc ccgatgattt atgaaaagct gctcgggctg    1140
gggattgatc tcacacaaga accggtaccg attgtgcctg ctgcacatta tacctgcggt    1200
```

-continued

```
ggtgtaatgg ttgatgatca tgggcgtacg gacgtcgagg gcttgtatgc cattggcgag   1260
gtgagttata ccggcttaca cggcgctaac cgcatggcct cgaattcatt gctggagtgt   1320
ctggtctatg gctggtcggc ggcggaagat atcaccagac gtatgcctta tgcccacgac   1380
atcagtacgt taccgccgtg ggatgaaagc cgcgttgaga accctgacga acgggtagta   1440
attcagcata actggcacga gctacgtctg tttatgtggg attacgttgg cattgtgcgc   1500
acaacgaagc gcctggaacg cgccctgcgg cggataacca tgctccaaca gaaatagac    1560 gaatattacg cccatttccg cgtctcaaat aatttgctgg agctgcgtaa tctggtacag   1620
gttgccgagt tgattgttcg ctgtgcaatg atgcgtaaag agagtcgggg gttgcatttc   1680
acgctggatt atccggaact gctcacccat tccggtccgt cgatcctttc ccccggcaat   1740
cattacataa acagaatcct ggcagaagca gccgcgaagg aagcagccgc gaaggaagca   1800
gccgcgaagg cagcagccct gcagatgagc gtaatgtttg atccagacac ggcgatttat   1860
cctttccccc cgaagccgac gccgttaagc attgatgaaa aagcgtatta ccgcgagaag   1920
ataaaacgtc tgctaaaaga acgtaatgcg gtgatggttg cccactacta taccgatccc   1980
gaaattcaac aactggcaga agaaaccggt ggctgtattt ctgattctct ggaaatggcg   2040
cgcttcggtg caaagcatcc cgcttctact ttgttagtcg ctggggtgag atttatggga   2100
gaaaccgcca aaattctcag tccgaaaaaa acaattctga tgccgacact tcaggctgaa   2160
tgttcactgg atctcggctg ccctgttgaa gaatttaacg cattttgcga tgcccatccc   2220
gatcgtactg tcgtcgtcta cgccaacact tctgctgcgg taaaagcgcg cgcagattgg   2280
gtggtaactt caagcattgc cgtcgaactt attgatcatc ttgatagttt gggtgaaaaa   2340
atcatctggg cacccgacaa acatctgggg cgttacgtgc aaaaacagac gggtggagac   2400
attctatgct ggcagggtgc ctgtattgtg catgatgaat ttaagactca ggcgttaacc   2460
cgcttgcaag aagaataccc ggatgctgcc atactggtgc atccagaatc accacaagct   2520
attgtcgata tggcggatgc ggtcggttcc accagtcaac tgatcgctgc tgcgaaaaca   2580
ttgccacatc agaggcttat tgtggcaacc gatcggggta ttttctacaa aatgcagcag   2640
gcggtgccag ataaagagtt actggaagca ccaaccgcag gtgagggtgc aacctgccgc   2700
agctgcgcgc attgtccgtg gatggccatg aatggccttc aggccatcgc agaggcatta   2760
gaacaggaag gaagcaatca cgaggttcat gttgatgaaa ggctgcgaga gagggcgctg   2820
gtgccgctca atcgtatgct ggattttgcg gctacactac gtggataacc cgggggatcc   2880
actagttcta gagcggccgc ttaattaatt aatctagagg catcaaataa aacgaaaggc   2940
tcagtcgaaa gactgggcct ttcgttttat ctgttgtttg tcggtgaacg ctctcctgag   3000
taggacaaat ccgccgccct agacctaggg gatatattcc gcttcctcgc tcactgactc   3060
gctacgctcg gtcgttcgac tgcggcgagc ggaaatggct tacgaacggg cggagattt    3120 cctggaagat gccaggaaga tacttaacag ggaagtgaga gggccgcggc aaagccgttt   3180
ttccataggc tccgccccc tgacaagcat cacgaaatct gacgctcaaa tcagtggtgg    3240
cgaaacccga caggactata aagataccag gcgtttcccc ctggcggctc cctcgtgcgc   3300
tctcctgttc ctgcctttcg gtttaccggt gtcattccgc tgttatggcc gcgtttgtct   3360
cattccacgc ctgacactca gttccgggta ggcagttcgc tccaagctgg actgtatgca   3420 cgaaccccc gttcagtccg accgctgcgc cttatccggt aactatcgtc ttgagtccaa    3480
cccggaaaga catgcaaaag caccactggc agcagccact ggtaattgat ttagaggagt   3540
```

-continued

```
tagtcttgaa gtcatgcgcc ggttaaggct aaactgaaag gacaagtttt ggtgactgcg     3600
ctcctccaag ccagttacct cggttcaaag agttggtagc tcagagaacc ttcgaaaaac     3660
cgccctgcaa ggcggttttt tcgttttcag agcaagagat tacgcgcaga ccaaaacgat     3720
ctcaagaaga tcatcttatt aatcagataa aatattacta gatttcagtg caatttatct     3780
cttcaaatgt agcacctgaa gtcagcccca tacgatataa gttgttacta gtgcttggat     3840
tctcaccaat aaaaaacgcc cggcggcaac cgagcgttct gaacaaatcc agatggagtt     3900
ctgaggtcat tactggatct atcaacagga gtccaagcga gctctcgaac cccagagtcc     3960
cgctcagaag aactcgtcaa gaaggcgata aaggcgatg cgctgcgaat cgggagcggc      4020
gataccgtaa agcacgagga agcggtcagc ccattcgccg ccaagctctt cagcaatatc     4080
acgggtagcc aacgctatgt cctgatagcg gtccgccaca cccagccggc cacagtcgat     4140
gaatccagaa aagcggccat tttccaccat gatattcggc aagcaggcat cgccatgggt     4200
cacgacgaga tcctcgccgt cgggcatgcg cgccttgagc ctggcgaaca gttcggctgg     4260
cgcgagcccc tgatgctctt cgtccagatc atcctgatcg acaagaccgg cttccatccg     4320
agtacgtgct cgctcgatgc gatgtttcgc ttggtggtcg aatgggcagg tagccggatc     4380
aagcgtatgc agccgccgca ttgcatcagc catgatggat actttctcgg caggagcaag     4440
gtgagatgac aggagatcct gccccggcac ttcgcccaat agcagccagt cccttcccgc     4500
ttcagtgaca acgtcgagca cagctgcgca aggaacgccc gtcgtggcca gccacgatag     4560
ccgcgctgcc tcgtcctgca gttcattcag ggcaccggac aggtcggtct tgacaaaaag     4620
aaccgggcgc ccctgcgctg acagccggaa cacggcggca tcagagcagc cgattgtctg     4680
ttgtgcccag tcatagccga atagcctctc cacccaagcg gccggagaac ctgcgtgcaa     4740
tccatcttgt tcaatcatgc gaaacgatcc tcatcctgtc tcttgatcag atcttgatcc     4800
cctgcgccat cagatccttg gcggcaagaa agccatccag tttactttgc agggcttccc     4860
aaccttacca gagggcgccc cagctggcaa ttccgacgtc tgtgtggaat ctcggacac      4920
cgaggagaat gtcaagaggc gaacacacaa cgtcttggag cgccagagga ggaacgagct     4980
aaaacggagc ttttttgccc tgcgtgacca gatcccggag ttggaaaaca atgaaaaggc     5040
ccccaaggta gttatcctta aaaaagccac agcatacatc ctgtccgtcc aagcagagga     5100
gcaaaagctc atttctgaag aggacttgtt gcggaaacga cgagaacagt tgaaacacaa     5160
acttgaacag ctacggaact cttgtgcgta aggaaaagta aggaaaacga ttccttctaa     5220
cagaaatgtc ctgagcaatc acctatgaac tgtcga                              5256
```

<210> SEQ ID NO 37
<211> LENGTH: 5271
<212> TYPE: DNA
<213> ORGANISM: Artificial Sequence
<220> FEATURE:
<223> OTHER INFORMATION: Plasmid vector (pNBHL4A)

<400> SEQUENCE: 37

```
ctcgagcata gcatttttat ccataagatt agcggatcta accttaacaa ttgtgagcgc       60
tcacaattat gatagattca attgtgagcg gataacaatt tcacacagaa ttcattaaag      120
aggagaaagg tacatatgaa tactctccct gaacattcat gtgacgtgtt gattatcggt      180
agcggcgcag ccggactttc actggcgcta cgcctggctg accagcatca ggtcatcgtt      240
ctaagtaaag gcccggtaac ggaaggttca acatttatg cccagggcgg tattgccgcc       300
gtgtttgatg aaactgacag cattgactcg catgtggaag acacattgat tgccggggct      360
```

```
ggtatttgcg atcgccatgc agttgaattt gtcgccagca atgcacgatc ctgtgtgcaa    420
tggctaatcg accaggggt gttgtttgat acccacattc aaccgaatgg cgaagaaagt    480
taccatctga cccgtgaagg tggacatagt caccgtcgta ttcttcatgc cgccgacgcc    540
accggtagag aagtagaaac cacgctggtg agcaaggcgc tgaaccatcc gaatattcgc    600
gtgctggagc gcagcaacgc ggttgatctg attgtttctg acaaaattgg cctgccgggc    660
acgcgacggg ttgttggcgc gtgggtatgg aaccgtaata agaaacggt ggaaacctgc    720 cacgcaaaag cggtggtgct ggcaaccggc ggtgcgtcga aggtttatca gtacaccacc    780
aatccggata tttcttctgg cgatggcatt gctatggcgt ggcgcgcagg ctgccgggtt    840
gccaatctcg aatttaatca gttccaccct accgcgctat atcacccaca ggcacgcaat    900
ttcctgttaa cagaagcact gcgcggcgaa ggcgcttatc tcaagcgccc ggatggtacg    960
cgttttatgc ccgattttga tgagcgcggc gaactggccc cgcgcgatat tgtcgcccgc   1020
gccattgacc atgaaatgaa acgcctcggc gcagattgta tgttccttga tatcagccat   1080
aagcccgccg attttattcg ccagcatttc ccgatgattt atgaaaagct gctcgggctg   1140
gggattgatc tcacacaaga accggtaccg attgtgcctg ctgcacatta tacctgcggt   1200
ggtgtaatgg ttgatgatca tgggcgtacg gacgtcgagg gcttgtatgc cattggcgag   1260
gtgagttata ccggcttaca cggcgctaac cgcatggcct cgaattcatt gctggagtgt   1320
ctggtctatg gctggtcggc ggcggaagat atcaccagac gtatgcctta tgcccacgac   1380
atcagtacgt taccgccgtg ggatgaaagc gcgttgaga accctgacga acgggtagta   1440
attcagcata actggcacga gctacgtctg tttatgtggg attacgttgg cattgtgcgc   1500
acaacgaagc gcctggaacg cgccctgcgg cggataacca tgctccaaca agaaatagac   1560
gaatattacg cccatttccg cgtctcaaat aatttgctgg agctgcgtaa tctggtacag   1620
gttgccgagt tgattgttcg ctgtgcaatg atgcgtaaag agagtcgggg gttgcatttc   1680
acgctggatt atccggaact gctcacccat tccggtccgt cgatcctttc ccccggcaat   1740
cattacataa acagaatcct ggcagaagca gccgcgaagg aagcagccgc gaaggaagca   1800
gccgcgaagg aagcagccgc gaaggcagca gccctgcaga tgagcgtaat gtttgatcca   1860
gacacggcga tttatccttt ccccccgaag ccgacgccgt taagcattga tgaaaaagcg   1920
tattaccgcg agaagataaa acgtctgcta aaagaacgta atgcggtgat ggttgcccac   1980
tactataccg atcccgaaat tcaacaactg gcagaagaaa ccggtggctg tatttctgat   2040
tctctggaaa tggcgcgctt cggtgcaaag catcccgctt ctactttgtt agtcgctggg   2100
gtgagattta tgggagaaac cgccaaaatt ctcagtccgg aaaaaacaat tctgatgccg   2160
acacttcagg ctgaatgttc actggatctc ggctgccctg ttgaagaatt taacgcattt   2220
tgcgatgccc atcccgatcg tactgtcgtc gtctacgcca acacttctgc tgcggtaaaa   2280
gcgcgcgcag attgggtggt aacttcaagc attgccgtcg aacttattga tcatcttgat   2340
agtttgggtg aaaaaatcat ctgggcaccc gacaaacatc tggggcgtta cgtgcaaaaa   2400
cagacgggtg gagacattct atgctggcag ggtgcctgta ttgtgcatga tgaatttaag   2460
actcaggcgt taacccgctt gcaagaagaa taccccgatg ctgccatact ggtgcatcca   2520
gaatcaccac aagctattgt cgatatggcg gatgcggtcg gttccaccag tcaactgatc   2580
gctgctgcga aaacattgcc acatcagagg cttattgtgg caaccgatcg gggtattttc   2640
tacaaaatgc agcaggcggt gccagataaa gagttactgg aagcaccaac cgcaggtgag   2700
```

```
ggtgcaacct gccgcagctg cgcgcattgt ccgtggatgg ccatgaatgg ccttcaggcc    2760
atcgcagagg cattagaaca ggaaggaagc aatcacgagg ttcatgttga tgaaaggctg    2820
cgagagaggg cgctggtgcc gctcaatcgt atgctggatt ttgcggctac actacgtgga    2880
taacccgggg gatccactag ttctagagcg gccgcttaat taattaatct agaggcatca    2940
aataaaacga aaggctcagt cgaaagactg ggcctttcgt tttatctgtt gtttgtcggt    3000
gaacgctctc ctgagtagga caaatccgcc gccctagacc tagggatat attccgcttc    3060 ctcgctcact gactcgctac gctcggtcgt tcgactgcgg cgagcggaaa tggcttacga    3120
acggggcgga gatttcctgg aagatgccag gaagatactt aacagggaag tgagagggcc    3180
gcggcaaagc cgttttttcca taggctccgc cccctgaca agcatcacga aatctgacgc    3240
tcaaatcagt ggtggcgaaa cccgacagga ctataaagat accaggcgtt tccccctggc    3300
ggctccctcg tgcgctctcc tgttcctgcc tttcggttta ccggtgtcat tccgctgtta    3360
tggccgcgtt tgtctcattc cacgcctgac actcagttcc gggtaggcag ttcgctccaa    3420
gctggactgt atgcacgaac cccccgttca gtccgaccgc tgcgccttat ccggtaacta    3480
tcgtcttgag tccaacccgg aaagacatgc aaaagcacca ctggcagcag ccactggtaa    3540
ttgatttaga ggagttagtc ttgaagtcat gcgccggtta aggctaaact gaaggacaa    3600 gttttggtga ctgcgctcct ccaagccagt tacctcggtt caaagagttg gtagctcaga    3660
gaaccttcga aaaccgcccc tgcaaggcgg ttttttcgtt ttcagagcaa gagattacgc    3720
gcagaccaaa acgatctcaa gaagatcatc ttattaatca gataaaatat tactagattt    3780
cagtgcaatt tatctcttca aatgtagcac ctgaagtcag ccccatacga tataagttgt    3840
tactagtgct tggattctca ccaataaaaa acgcccggcg caaccgagc gttctgaaca    3900 aatccagatg gagttctgag gtcattactg gatctatcaa caggagtcca agcgagctct    3960 cgaacccag agtccgctc agaagaactc gtcaagaagg cgatagaagg cgatgcgctg    4020
cgaatcggga gcggcgatac cgtaaagcac gaggaagcgg tcagcccatt cgccgccaag    4080
ctcttcagca atatcacggg tagccaacgc tatgtcctga tagcggtccg ccacacccag    4140
ccggccacag tcgatgaatc cagaaaagcg gccattttcc accatgatat tcggcaagca    4200
ggcatcgcca tgggtcacga cgagatcctc gccgtcgggc atgcgcgcct tgagcctggc    4260
gaacagttcg gctggcgcga gcccctgatg ctcttcgtcc agatcatcct gatcgacaag    4320
accggcttcc atccgagtac gtgctcgctc gatgcgatgt ttcgcttggt ggtcgaatgg    4380
gcaggtagcc ggatcaagcg tatgcagccg ccgcattgca tcagccatga tggatacttt    4440
ctcggcagga gcaaggtgag atgacaggag atcctgcccc ggcacttcgc ccaatagcag    4500
ccagtccctt cccgcttcag tgacaacgtc gagcacagct gcgcaaggaa cgcccgtcgt    4560
ggccagccac gatagccgcg ctgcctcgtc ctgcagttca ttcagggcac cggacaggtc    4620
ggtcttgaca aaaagaaccg ggcgcccctg cgctgacagc cggaacacgg cggcatcaga    4680
gcagccgatt gtctgttgtg cccagtcata gccgaatagc ctctccaccc aagcggccgg    4740
agaacctgcg tgcaatccat cttgttcaat catgcgaaac gatcctcatc ctgtctcttg    4800 atcgatctt gatcccctgc gccatcagat ccttggcggc aagaaagcca tccagtttac    4860
tttgcagggc ttcccaacct taccagaggg cgccccagct ggcaattccg acgtctgtgt    4920
ggaattctcg gacaccgagg agaatgtcaa gaggcgaaca cacaacgtct tggagcgcca    4980
gaggaggaac gagctaaaac ggagcttttt tgccctgcgt gaccagatcc cggagttgga    5040
aaacaatgaa aaggccccca aggtagttat ccttaaaaaa gccacagcat acatcctgtc    5100
```

```
cgtccaagca gaggagcaaa agctcatttc tgaagaggac ttgttgcgga aacgacgaga    5160
acagttgaaa cacaaacttg aacagctacg gaactcttgt gcgtaaggaa aagtaaggaa    5220
aacgattcct tctaacagaa atgtcctgag caatcaccta tgaactgtcg a             5271
```

<210> SEQ ID NO 38
<211> LENGTH: 5286
<212> TYPE: DNA
<213> ORGANISM: Artificial Sequence
<220> FEATURE:
<223> OTHER INFORMATION: Plasmid vector (pNBHL5A)

<400> SEQUENCE: 38

```
ctcgagcata gcattttat ccataagatt agcggatcta acctttacaa ttgtgagcgc      60
tcacaattat gatagattca attgtgagcg gataacaatt tcacacagaa ttcattaaag    120
aggagaaagg tacatatgaa tactctccct gaacattcat gtgacgtgtt gattatcggt    180
agcggcgcag ccggactttc actgcgcta cgcctggctg accagcatca ggtcatcgtt     240
ctaagtaaag gcccggtaac ggaaggttca acattttatg cccagggcgg tattgccgcc    300
gtgtttgatg aaactgacag cattgactcg catgtggaag acacattgat tgccggggct    360
ggtatttgcg atcgccatgc agttgaattt gtcgccagca atgcacgatc ctgtgtgcaa    420
tggctaatcg accagggggt gttgtttgat acccacattc aaccgaatgg cgaagaaagt    480
taccatctga cccgtgaagg tggacatagt caccgtcgta ttcttcatgc cgccgacgcc    540
accggtagag aagtagaaac cacgctggtg agcaaggcgc tgaaccatcc gaatattcgc    600
gtgctggagc gcagcaacgc ggttgatctg attgtttctg acaaaattgg cctgccgggc    660
acgcgacggg ttgttggcgc gtgggtatgg aaccgtaata agaaacggt ggaaacctgc     720 cacgcaaaag cggtggtgct ggcaaccggc ggtgcgtcga aggtttatca gtacaccacc    780
aatccggata tttcttctgg cgatggcatt gctatggcgt ggcgcgcagg ctgccgggtt    840
gccaatctcg aatttaatca gttccaccct accgcgctat atcacccaca ggcacgcaat    900
ttcctgttaa cagaagcact gcgcggcgaa ggcgcttatc tcaagcgccc ggatggtacg    960
cgttttatgc ccgattttga tgagcgcggg gaactggccc cgcgcgatat tgtcgcccgc   1020
gccattgacc atgaaatgaa acgcctcggc gcagattgta tgttccttga tatcagccat   1080
aagcccgccg attttattcg ccagcatttc ccgatgattt atgaaaagct gctcgggctg   1140
gggattgatc tcacacaaga accggtaccg attgtgcctg ctgcacatta tacctgcggt   1200
ggtgtaatgg ttgatgatca tgggcgtacg gacgtcgagg gcttgtatgc cattggcgag   1260
gtgagttata ccggcttaca cggcgctaac cgcatggcct cgaattcatt gctggagtgt   1320
ctggtctatg gctggtcggc ggcggaagat atcaccagac gtatgcctta tgcccacgac   1380
atcagtacgt taccgccgtg ggatgaaagc gcgttgaga accctgacga acgggtagta    1440
attcagcata actggcacga gctacgtctg tttatgtggg attacgttgg cattgtgcgc   1500
acaacgaagc gcctggaacg cgccctgcgg cggataacca tgctccaaca agaaatagac   1560
gaatattacg cccatttccg cgtctcaaat aatttgctgg agctgcgtaa tctggtacag   1620
gttgccgagt tgattgttcg ctgtgcaatg atgcgtaaag agagtcgggg gttgcatttc   1680
acgctggatt atccggaact gctcacccat tccggtccgt cgatcctttc ccccggcaat   1740
cattacataa acagaatcct ggcagaagca gccgcgaagg aagcagccgc gaaggaagca   1800
gccgcgaagg aagcagccgc gaaggaagca gccgcgaagg cagcagccct gcagatgagc   1860
```

```
gtaatgtttg atccagacac ggcgatttat cctttccccc cgaagccgac gccgttaagc    1920
attgatgaaa aagcgtatta ccgcgagaag ataaaacgtc tgctaaaaga acgtaatgcg    1980
gtgatggttg cccactacta taccgatccc gaaattcaac aactggcaga agaaaccggt    2040
ggctgtattt ctgattctct ggaaatggcg cgcttcggtg caaagcatcc cgcttctact    2100
ttgttagtcg ctggggtgag atttatggga gaaaccgcca aaattctcag tccggaaaaa    2160
acaattctga tgccgacact tcaggctgaa tgttcactgg atctcggctg ccctgttgaa    2220
gaatttaacg cattttgcga tgcccatccc gatcgtactg tcgtcgtcta cgccaacact    2280
tctgctgcgg taaaagcgcg cgcagattgg gtggtaactt caagcattgc cgtcgaactt    2340
attgatcatc ttgatagttt gggtgaaaaa atcatctggg cacccgacaa acatctgggg    2400
cgttacgtgc aaaaacagac gggtggagac attctatgct ggcagggtgc ctgtattgtg    2460
catgatgaat ttaagactca ggcgttaacc cgcttgcaag aagaataccc ggatgctgcc    2520
atactggtgc atccagaatc accacaagct attgtcgata tggcggatgc ggtcggttcc    2580
accagtcaac tgatcgctgc tgcgaaaaca ttgccacatc agaggcttat tgtggcaacc    2640
gatcggggta ttttctacaa aatgcagcag gcggtgccag ataaagagtt actggaagca    2700
ccaaccgcag gtgagggtgc aacctgccgc agctgcgcgc attgtccgtg gatggccatg    2760
aatggccttc aggccatcgc agaggcatta aacaggaag gaagcaatca cgaggttcat    2820
gttgatgaaa ggctgcgaga gagggcgctg gtgccgctca atcgtatgct ggattttgcg    2880
gctacactac gtggataacc cggggatcc actagttcta gagcggccgc ttaattaatt    2940
aatctagagg catcaaataa aacgaaaggc tcagtcgaaa gactgggcct ttcgttttat    3000
ctgttgtttg tcggtgaacg ctctcctgag taggacaaat ccgccgccct agacctaggg    3060
gatatattcc gcttcctcgc tcactgactc gctacgctcg tcgttcgac tgcggcgagc    3120 ggaaatggct tacgaacggg gcggagattt cctggaagat gccaggaaga tacttaacag    3180
ggaagtgaga gggccgcggc aaagccgttt ttccataggc tccgcccccc tgacaagcat    3240
cacgaaatct gacgctcaaa tcagtggtgg cgaaacccga caggactata agataccag    3300 gcgtttcccc ctggcggctc cctcgtgcgc tctcctgttc ctgcctttcg gtttaccggt    3360
gtcattccgc tgttatggcc gcgtttgtct cattccacgc ctgacactca gttccgggta    3420
ggcagttcgc tccaagctgg actgtatgca cgaaccccc gttcagtccg accgctgcgc    3480
cttatccggt aactatcgtc ttgagtccaa cccggaaaga catgcaaaag caccactggc    3540
agcagccact ggtaattgat ttagaggagt tagtcttgaa gtcatgcgcc ggttaaggct    3600
aaactgaaag gacaagtttt ggtgactgcg ctcctccaag ccagttacct cggttcaaag    3660
agttggtagc tcagagaacc ttcgaaaaac cgccctgcaa ggcggttttt tcgttttcag    3720
agcaagagat tacgcgcaga ccaaaacgat ctcaagaaga tcatcttatt aatcagataa    3780
aatattacta gatttcagtg caatttatct cttcaaatgt agcacctgaa gtcagcccca    3840
tacgatataa gttgttacta gtgcttggat tctcaccaat aaaaaacgcc cggcggcaac    3900
cgagcgttct gaacaaatcc agatggagtt ctgaggtcat tactggatct atcaacagga    3960
gtccaagcga gctctcgaac cccagagtcc cgctcagaag aactcgtcaa gaaggcgata    4020
gaaggcgatg cgctgcgaat cgggagcggc gataccgtaa agcacgagga agcggtcagc    4080
ccattcgccg ccaagctctt cagcaatatc acgggtagcc aacgctatgt cctgatagcg    4140
gtccgccaca cccagccggc cacagtcgat gaatccagaa aagcggccat tttccaccat    4200
gatattcggc aagcaggcat cgccatgggt cacgacgaga tcctcgccgt cgggcatgcg    4260
```

```
cgccttgagc ctggcgaaca gttcggctgg cgcgagcccc tgatgctctt cgtccagatc    4320
atcctgatcg acaagaccgg cttccatccg agtacgtgct cgctcgatgc gatgtttcgc    4380
ttggtggtcg aatgggcagg tagccggatc aagcgtatgc agccgccgca ttgcatcagc    4440
catgatggat actttctcgg caggagcaag gtgagatgac aggagatcct gccccggcac    4500
ttcgcccaat agcagccagt cccttcccgc ttcagtgaca cgtcgagca cagctgcgca    4560 aggaacgccc gtcgtggcca gccacgatag ccgcgctgcc tcgtcctgca gttcattcag    4620
ggcaccggac aggtcggtct tgacaaaaag aaccgggcgc ccctgcgctg acagccggaa    4680
cacggcggca tcagagcagc cgattgtctg ttgtgcccag tcatagccga atagcctctc    4740
cacccaagcg gccggagaac ctgcgtgcaa tccatcttgt tcaatcatgc gaaacgatcc    4800
tcatcctgtc tcttgatcag atcttgatcc cctgcgccat cagatccttg gcggcaagaa    4860
agccatccag tttactttgc agggcttccc aaccttacca gagggcgccc cagctggcaa    4920
ttccgacgtc tgtgtggaat ctcggacac cgaggagaat gtcaagaggc gaacacacaa    4980
cgtcttggag cgccagagga ggaacgagct aaaacggagc ttttttgccc tgcgtgacca    5040
gatcccggag ttggaaaaca atgaaaaggc ccccaaggta gttatcctta aaaaagccac    5100
agcatacatc ctgtccgtcc aagcagagga gcaaaagctc atttctgaag aggacttgtt    5160
gcggaaacga cgagaacagt tgaaacacaa acttgaacag ctacgaaact cttgtgcgta    5220
aggaaaagta aggaaaacga ttccttctaa cagaaatgtc ctgagcaatc acctatgaac    5280
tgtcga                                                                5286

<210> SEQ ID NO 39
<211> LENGTH: 5244
<212> TYPE: DNA
<213> ORGANISM: Artificial Sequence
<220> FEATURE:
<223> OTHER INFORMATION: Plasmid vector (pNBFL3A)

<400> SEQUENCE: 39
ctcgagcata gcattttat ccataagatt agcggatcta accttacaa ttgtgagcgc       60 tcacaattat gatagattca attgtgagcg gataacaatt tcacacagaa ttcattaaag    120
aggagaaagg tacatatgaa tactctccct gaacattcat gtgacgtgtt gattatcggt    180
agcggcgcag ccggactttc actggcgcta cgcctggctg accagcatca ggtcatcgtt    240
ctaagtaaag gcccggtaac ggaaggttca acattttatg cccagggcgg tattgccgcc    300
gtgtttgatg aaactgacag cattgactcg catgtggaag acacattgat tgccggggct    360
ggtatttgcg atcgccatgc agttgaattt gtcgccagca atgcacgatc ctgtgtgcaa    420
tggctaatcg accaggggt gttgtttgat acccacattc aaccgaatgg cgaagaaagt    480
taccatctga cccgtgaagg tggacatagt caccgtcgta ttcttcatgc cgccgacgcc    540
accggtagaa aagtagaaac cacgctggtg agcaaggcgc tgaaccatcc gaatattcgc    600
gtgctggagc gcagcaacgc ggttgatctg attgttctg acaaaattgg cctgccgggc    660
acgcgacggg ttgttggcgc gtgggtatgg aaccgtaata agaaacggt ggaaacctgc    720 cacgcaaaag cggtggtgct ggcaaccggc ggtgcgtcga aggtttatca gtacaccacc    780
aatccggata tttcttctgg cgatggcatt gctatggcgt ggcgcgcagg ctgccgggtt    840
gccaatctcg aatttaatca gttccaccct accgcgctat atcacccaca ggcacgcaat    900
ttcctgttaa cagaagcact gcgcggcgaa ggcgcttatc tcaagcgccc ggatggtacg    960
```

```
cgttttatgc ccgattttga tgagcgcggc gaactggccc cgcgcgatat tgtcgcccgc    1020
gccattgacc atgaaatgaa acgcctcggc gcagattgta tgttccttga tatcagccat    1080
aagcccgccg attttattcg ccagcatttc ccgatgattt atgaaaagct gctcgggctg    1140
gggattgatc tcacacaaga accggtaccg attgtgcctg ctgcacatta tacctgcggt    1200
ggtgtaatgg ttgatgatca tgggcgtacg gacgtcgagg gcttgtatgc cattggcgag    1260
gtgagttata ccggcttaca cggcgctaac cgcatggcct cgaattcatt gctggagtgt    1320
ctggtctatg gctggtcggc ggcggaagat atcaccagac gtatgcctta tgcccacgac    1380
atcagtacgt taccgccgtg ggatgaaagc gcgttgaga accctgacga acgggtagta    1440
attcagcata actggcacga gctacgtctg tttatgtggg attacgttgg cattgtgcgc    1500
acaacgaagc gcctggaacg cgccctgcgg cggataacca tgctccaaca agaaatagac    1560
gaatattacg cccatttccg cgtctcaaat aatttgctgg agctgcgtaa tctggtacag    1620
gttgccgagt tgattgttcg ctgtgcaatg atgcgtaaag agagtcgggg gttgcatttc    1680
acgctggatt atccggaact gctcacccat tccggtccgt cgatcctttc ccccggcaat    1740
cattacataa acagaatcct gggtggtggt agcggtggtg gtagcggtgg tggtagcgca    1800
gcagccctgc agatgagcgt aatgtttgat ccagacacgg cgatttatcc tttcccccg    1860 aagccgacgc cgttaagcat tgatgaaaaa gcgtattacc gcgagaagat aaaacgtctg    1920
ctaaaagaac gtaatgcggt gatggttgcc cactactata ccgatcccga aattcaacaa    1980
ctggcagaag aaaccggtgg ctgtatttct gattctctgg aaatggcgcg cttcggtgca    2040
aagcatcccg cttctacttt gttagtcgct ggggtgagat ttatgggaga aaccgccaaa    2100
attctcagtc cggaaaaaac aattctgatg ccgacacttc aggctgaatg ttcactggat    2160
ctcggctgcc ctgttgaaga atttaacgca ttttgcgatg cccatcccga tcgtactgtc    2220
gtcgtctacg ccaacacttc tgctgcggta aaagcgcgcg cagattgggt ggtaacttca    2280
agcattgccg tcgaacttat tgatcatctt gatagtttgg gtgaaaaaat catctgggca    2340
cccgacaaac atctggggcg ttacgtgcaa aaacagacgg gtggagacat tctatgctgg    2400
cagggtgcct gtattgtgca tgatgaattt aagactcagg cgttaacccg cttgcaagaa    2460
gaatacccgg atgctgccat actggtgcat ccagaatcac cacaagctat tgtcgatatg    2520
gcggatgcgg tcggttccac cagtcaactg atcgctgctg cgaaaacatt gccacatcag    2580
aggcttattg tggcaaccga tcggggtatt ttctacaaaa tgcagcaggc ggtgccagat    2640
aaagagttac tggaagcacc aaccgcaggt gagggtgcaa cctgccgcag ctgcgcgcat    2700
tgtccgtgga tggccatgaa tggccttcag gccatcgcag aggcattaga acaggaagga    2760
agcaatcacg aggttcatgt tgatgaaagg ctgcgagaga gggcgctggt gccgctcaat    2820
cgtatgctgg attttgcggc tacactacgt ggataacccg ggggatccac tagttctaga    2880
gcggccgctt aattaattaa tctagaggca tcaaataaaa cgaaaggctc agtcgaaaga    2940
ctgggccttt cgttttatct gttgtttgtc ggtgaacgct ctcctgagta ggacaaatcc    3000 gccgcctag acctagggga tatattccgc ttcctcgctc actgactcgc tacgctcggt    3060
cgttcgactg cggcgagcgg aaatggctta cgaacgggc ggagatttcc tggaagatgc    3120
caggaagata cttaacaggg aagtgagagg gccgcggcaa agccgttttt ccataggctc    3180
cgcccccctg acaagcatca cgaaatctga cgctcaaatc agtggtggcg aaacccgaca    3240
ggactataaa gataccaggc gtttccccct ggcggctccc tcgtgcgctc tcctgttcct    3300
gcctttcggt ttaccggtgt cattccgctg ttatggccgc gtttgtctca ttccacgcct    3360
```

```
gacactcagt tccgggtagg cagttcgctc caagctggac tgtatgcacg aaccccccgt    3420
tcagtccgac cgctgcgcct tatccggtaa ctatcgtctt gagtccaacc cggaaagaca    3480
tgcaaaagca ccactggcag cagccactgg taattgattt agaggagtta gtcttgaagt    3540
catgcgccgg ttaaggctaa actgaaagga caagttttgg tgactgcgct cctccaagcc    3600
agttacctcg gttcaaagag ttggtagctc agagaacctt cgaaaaccg ccctgcaagg     3660 cggttttttc gttttcagag caagagatta cgcgcagacc aaaacgatct caagaagatc    3720
atcttattaa tcagataaaa tattactaga tttcagtgca atttatctct caaatgtag     3780 cacctgaagt cagccccata cgatataagt tgttactagt gcttggattc tcaccaataa    3840
aaaacgcccg gcggcaaccg agcgttctga acaaatccag atggagttct gaggtcatta    3900
ctggatctat caacaggagt ccaagcgagc tctcgaaccc cagagtcccg ctcagaagaa    3960
ctcgtcaaga aggcgataga aggcgatgcg ctgcgaatcg ggagcggcga taccgtaaag    4020
cacgaggaag cggtcagccc attcgccgcc aagctcttca gcaatatcac gggtagccaa    4080
cgctatgtcc tgatagcggt ccgccacacc cagccggcca cagtcgatga atccagaaaa    4140
gcggccattt tccaccatga tattcggcaa gcaggcatcg ccatgggtca cgacgagatc    4200
ctcgccgtcg gcatgcgcg ccttgagcct ggcgaacagt tcggctggcg cgagcccctg     4260
atgctcttcg tccagatcat cctgatcgac aagaccggct tccatccgag tacgtgctcg    4320
ctcgatgcga tgtttcgctt ggtggtcgaa tgggcaggta gccggatcaa gcgtatgcag    4380
ccgccgcatt gcatcagcca tgatggatac tttctcggca ggagcaaggt gagatgacag    4440
gagatcctgc cccggcactt cgcccaatag cagccagtcc cttcccgctt cagtgacaac    4500
gtcgagcaca gctgcgcaag gaacgcccgt cgtggccagc cacgatagcc gcgctgcctc    4560
gtcctgcagt tcattcaggg caccggacag gtcggtcttg acaaaaagaa ccgggcgccc    4620
ctgcgctgac agccggaaca cggcggcatc agagcagccg attgtctgtt gtgcccagtc    4680
atagccgaat agcctctcca cccaagcggc cggagaacct gcgtgcaatc catcttgttc    4740
aatcatgcga aacgatcctc atcctgtctc ttgatcagat cttgatcccc tgcgccatca    4800
gatccttggc ggcaagaaag ccatccagtt tactttgcag ggcttcccaa ccttaccaga    4860
gggcgcccca gctggcaatt ccgacgtctg tgtggaattc tcggacaccg aggagaatgt    4920
caagaggcga acacacaacg tcttggagcg ccagaggagg aacagctaa aacgagctt      4980 ttttgccctg cgtgaccaga tcccggagtt ggaaaacaat gaaaaggccc ccaaggtagt    5040
tatccttaaa aaagccacag catacatcct gtccgtccaa gcagaggagc aaaagctcat    5100
ttctgaagag gacttgttgc ggaaacgacg agaacagttg aaacacaaac ttgaacagct    5160
acggaactct tgtgcgtaag gaaaagtaag gaaaacgatt ccttctaaca gaaatgtcct    5220
gagcaatcac ctatgaactg tcga                                           5244
```

<210> SEQ ID NO 40
<211> LENGTH: 5256
<212> TYPE: DNA
<213> ORGANISM: Artificial Sequence
<220> FEATURE:
<223> OTHER INFORMATION: Plasmid vector (pNBFL4A)

<400> SEQUENCE: 40

```
ctcgagcata gcattttat ccataagatt agcggatcta accttacaa ttgtgagcgc       60 tcacaattat gatagattca attgtgagcg gataacaatt tcacacagaa ttcattaaag    120
```

```
aggagaaagg tacatatgaa tactctccct gaacattcat gtgacgtgtt gattatcggt    180
agcggcgcag ccggactttc actggcgcta cgcctggctg accagcatca ggtcatcgtt    240
ctaagtaaag gcccggtaac ggaaggttca acattttatg cccagggcgg tattgccgcc    300
gtgtttgatg aaactgacag cattgactcg catgtggaag acacattgat tgccggggct    360
ggtatttgcg atcgccatgc agttgaattt gtcgccagca atgcacgatc ctgtgtgcaa    420
tggctaatcg accagggggt gttgtttgat acccacattc aaccgaatgg cgaagaaagt    480
taccatctga cccgtgaagg tggacatagt caccgtcgta ttcttcatgc cgccgacgcc    540
accggtagag aagtagaaac cacgctggtg agcaaggcgc tgaaccatcc gaatattcgc    600
gtgctggagc gcagcaacgc ggttgatctg attgtttctg acaaaattgg cctgccgggc    660
acgcgacggt tgttggcgc gtgggtatgg aaccgtaata agaaacggt ggaaacctgc    720
cacgcaaaag cggtggtgct ggcaaccggc ggtgcgtcga aggtttatca gtacaccacc    780
aatccggata tttcttctgg cgatggcatt gctatggcgt ggcgcgcagg ctgccgggtt    840
gccaatctcg aatttaatca gttccaccct accgcgctat atcacccaca ggcacgcaat    900
ttcctgttaa cagaagcact gcgcggcgaa ggcgcttatc tcaagcgccc ggatggtacg    960
cgttttatgc ccgattttga tgagcgcggc gaactggccc cgcgcgatat tgtcgcccgc   1020
gccattgacc atgaaatgaa acgcctcggc gcagattgta tgttccttga tatcagccat   1080
aagcccgccg attttattcg ccagcatttc ccgatgattt atgaaaagct gctcgggctg   1140
gggattgatc tcacacaaga accggtaccg attgtgcctg ctgcacatta tacctgcggt   1200
ggtgtaatgg ttgatgatca tgggcgtacg gacgtcgagg gcttgtatgc cattggcgag   1260
gtgagttata ccggcttaca cggcgctaac cgcatggcct cgaattcatt gctggagtgt   1320
ctggtctatg gctggtcggc ggcggaagat atcaccagac gtatgcctta tgcccacgac   1380
atcagtacgt taccgccgtg ggatgaaagc cgcgttgaga ccctgacga acgggtagta   1440
attcagcata actggcacga gctacgtctg tttatgtggg attacgttgg cattgtgcgc   1500
acaacgaagc gcctggaacg cgccctgcgg cggataacca tgctccaaca gaaatagac    1560
gaatattacg cccatttccg cgtctcaaat aatttgctgg agctgcgtaa tctggtacag   1620
gttgccgagt tgattgttcg ctgtgcaatg atgcgtaaag agagtcgggg gttgcatttc   1680
acgctggatt atccggaact gctcacccat tccggtccgt cgatcctttc ccccggcaat   1740
cattacataa acagaatcct gggtggtggt agcggtggtg gtagcggtgg tggtagcggt   1800
ggtggtagcg cagcagccct gcagatgagc gtaatgtttg atccagacac ggcgatttat   1860
cctttccccc cgaagccgac gccgttaagc attgatgaaa aagcgtatta ccgcgagaag   1920
ataaaacgtc tgctaaaaga acgtaatgcg gtgatggttg cccactacta taccgatccc   1980
gaaattcaac aactggcaga agaaaccggt ggctgtattt ctgattctct ggaaatggcg   2040
cgcttcggtg caaagcatcc cgcttctact ttgttagtcg ctggggtgag atttatggga   2100
gaaaccgcca aaattctcag tccggaaaaa acaattctga tgccgacact tcaggctgaa   2160
tgttcactgg atctcggctg ccctgttgaa gaatttaacg cattttgcga tgcccatccc   2220
gatcgtactg tcgtcgtcta cgccaacact tctgctgcgg taaagcgcg cgcagattgg   2280
gtggtaactt caagcattgc cgtcgaactt attgatcatc ttgatagttt gggtgaaaaa   2340
atcatctggg cacccgacaa acatctgggg cgttacgtgc aaaaacagac gggtggagac   2400
attctatgct ggcagggtgc ctgtattgtg catgatgaat ttaagactca ggcgttaacc   2460
cgcttgcaag aagaataccc ggatgctgcc atactggtgc atccagaatc accacaagct   2520
```

```
attgtcgata tggcggatgc ggtcggttcc accagtcaac tgatcgctgc tgcgaaaaca    2580
ttgccacatc agaggcttat tgtggcaacc gatcgggta  ttttctacaa aatgcagcag    2640
gcggtgccag ataaagagtt actggaagca ccaaccgcag gtgagggtgc aacctgccgc    2700
agctgcgcgc attgtccgtg gatggccatg aatggcttc  aggccatcgc agaggcatta    2760
gaacaggaag gaagcaatca cgaggttcat gttgatgaaa ggctgcgaga gagggcgctg    2820
gtgccgctca atcgtatgct ggattttgcg gctacactac gtggataacc cggggatcc    2880
actagttcta gagcggccgc ttaattaatt aatctagagg catcaaataa aacgaaaggc    2940
tcagtcgaaa gactgggcct ttcgttttat ctgttgtttg tcggtgaacg ctctcctgag    3000
taggacaaat ccgccgccct agacctaggg gatatattcc gcttcctcgc tcactgactc    3060
gctacgctcg gtcgttcgac tgcggcgagc ggaaatggct tacgaacggg gcggagattt    3120
cctggaagat gccaggaaga tacttaacag ggaagtgaga gggccgcggc aaagccgttt    3180
ttccataggc tccgcccccc tgacaagcat cacgaaatct gacgctcaaa tcagtggtgg    3240
cgaaacccga caggactata aagataccag gcgtttcccc ctggcggctc cctcgtgcgc    3300
tctcctgttc ctgcctttcg gtttaccggt gtcattccgc tgttatggcc gcgtttgtct    3360
cattccacgc ctgacactca gttccgggta ggcagttcgc tccaagctgg actgtatgca    3420
cgaaccccc  gttcagtccg accgctgcgc cttatccggt aactatcgtc ttgagtccaa    3480
cccggaaaga catgcaaaag caccactggc agcagccact ggtaattgat ttagaggagt    3540
tagtcttgaa gtcatgcgcc ggttaaggct aaactgaaag gacaagtttt ggtgactgcg    3600
ctcctccaag ccagttacct cggttcaaag agttggtagc tcagagaacc ttcgaaaaac    3660
cgccctgcaa ggcggttttt tcgttttcag agcaagagat tacgcgcaga ccaaaacgat    3720
ctcaagaaga tcatcttatt aatcagataa aatattacta gatttcagtg caatttatct    3780
cttcaaatgt agcacctgaa gtcagcccca tacgatataa gttgttacta gtgcttggat    3840
tctcaccaat aaaaaacgcc cggcggcaac cgagcgttct gaacaaatcc agatggagtt    3900
ctgaggtcat tactgatct  atcaacagga gtccaagcga gctctcgaac cccagagtcc    3960
cgctcagaag aactcgtcaa gaaggcgata gaaggcgatg cgctgcgaat cgggagcggc    4020
gataccgtaa agcacgagga agcggtcagc ccattcgccg ccaagctctt cagcaatatc    4080
acgggtagcc aacgctatgt cctgatagcg gtccgccaca cccagccggc cacagtcgat    4140
gaatccagaa aagcggccat tttccaccat gatattcggc aagcaggcat cgccatgggt    4200
cacgacgaga tcctcgccgt cgggcatgcg cgccttgagc ctggcgaaca gttcggctgg    4260
cgcgagcccc tgatgctctt cgtccagatc atcctgatcg acaagaccgg cttccatccg    4320
agtacgtgct cgctcgatgc gatgtttcgc ttggtggtcg aatgggcagg tagccggatc    4380
aagcgtatgc agccgccgca ttgcatcagc catgatggat actttctcgg caggagcaag    4440
gtgagatgac aggagatcct gccccggcac ttcgcccaat agcagccagt cccttcccgc    4500
ttcagtgaca acgtcgagca cagctgcgca aggaacgccc gtcgtggcca gccacgatag    4560
ccgcgctgcc tcgtcctgca gttcattcag ggcaccggac aggtcggtct tgacaaaaag    4620
aaccgggcgc cctgcgctg  acagccggaa cacgcggca  tcagagcagc cgattgtctg    4680
ttgtgcccag tcatagccga atagcctctc cacccaagcg gccggagaac ctgcgtgcaa    4740
tccatcttgt tcaatcatgc gaaacgatcc tcatcctgtc tcttgatcag atcttgatcc    4800
cctgcgccat cagatccttg gcggcaagaa agccatccag tttactttgc agggcttccc    4860
```

| | |
|---|---:|
| aaccttacca gagggcgccc cagctggcaa ttccgacgtc tgtgtggaat tctcggacac | 4920 |
| cgaggagaat gtcaagaggc gaacacacaa cgtcttggag cgccagagga ggaacgagct | 4980 |
| aaaacggagc ttttttgccc tgcgtgacca gatcccggag ttggaaaaca atgaaaaggc | 5040 |
| cccccaaggta gttatcctta aaaaagccac agcatacatc ctgtccgtcc aagcaggaga | 5100 |
| gcaaaagctc atttctgaag aggacttgtt gcggaaacga cgagaacagt tgaaacacaa | 5160 |
| acttgaacag ctacggaact cttgtgcgta aggaaaagta aggaaaacga ttccttctaa | 5220 |
| cagaaatgtc ctgagcaatc acctatgaac tgtcga | 5256 |

<210> SEQ ID NO 41
<211> LENGTH: 9193
<212> TYPE: DNA
<213> ORGANISM: Artificial Sequence
<220> FEATURE:
<223> OTHER INFORMATION: Plasmid vector (pCPA)

<400> SEQUENCE: 41

| | |
|---|---:|
| cccgtcttac tgtcgggaat tcgcgttggc cgattcatta atgcagctgg cacgacaggt | 60 |
| ttcccgactg gaaagcgggc agtgagcgca acgcaattaa tgtgagttag ctcactcatt | 120 |
| aggcacccca ggctttacac tttatgcttc cggctcgtat gttgtgtgga attgtgagcg | 180 |
| gataacaatt tcacacagga aacagctatg accatgatta cgccaagctt ctgtaggccg | 240 |
| gataaggcgc tcgcgccgca tccggcactg ttgccaaact ccagtgccgc aataatgtcg | 300 |
| gatgcgatac ttgcgcatct tatccgacct acacctttgg tgttacttgg ggcgattttt | 360 |
| taacatttcc ataagttacg cttatttaaa gcgtcgtgaa tttaatgacg taaattcctg | 420 |
| ctatttattc gtttgctgaa gcgatttcgc agcatttgac gtcaccgctt ttacgtggct | 480 |
| ttataaaaga cgacgaaaag caaagcccga gcatattcgc gccaatgcga cgtgaaggat | 540 |
| acagggctat caaacgataa gatggggtgt ctggggtaat atgaacgaac aatattccgc | 600 |
| attgcgtagt aatgtcagta tgctcggcaa agtgctggga gaaaccatca aggatgcgtt | 660 |
| gggagaacac attcttgaac gcgtagaaac tatccgtaag ttgtcgaaat cttcacgcgc | 720 |
| tggcaatgat gctaaccgcc aggagttgct caccaccctta caaaatttgt cgaacgacga | 780 |
| gctgctgccc gttgcgcgtg cgtttagtca gttcctgaac ctggccaaca ccgccgagca | 840 |
| ataccacagc atttcgccga aaggcgaagc tgccagcaac ccggaagtga tcgcccgcac | 900 |
| cctgcgtaaa ctgaaaaacc agccggaact gagcgaagac accatcaaaa aagcagtgga | 960 |
| atcgctgtcg ctggaactgg tcctcacggc tcacccaacc gaaattaccc gtcgtacact | 1020 |
| gatccacaaa atggtggaag tgaacgcctg tttaaaacag ctcgataaca agatatcgc | 1080 |
| tgactacgaa cacaaccagc tgatgcgtcg cctgcgccag ttgatcgccc agtcatggca | 1140 |
| taccgatgaa atccgtaagc tgcgtccaag cccggtagat gaagccaaat ggggctttgc | 1200 |
| cgtagtggaa aacagcctgt ggcaaggcgt accaaattac ctgcgcgaac tgaacgaaca | 1260 |
| actggaagag aacctcggct acaaactgcc cgtcgaattt gttccggtcc gttttacttc | 1320 |
| gtggatgggc ggcgaccgcg acggcaaccc gaacgtcact gccgatatca cccgccacgt | 1380 |
| cctgctactc agccgctgga aagccaccga tttgttcctg aaagatattc aggtgctggt | 1440 |
| ttctgaactg tcgatggttg aagcgacccc tgaactgctg gcgctggttg gcgaagaagg | 1500 |
| tgccgcagaa ccgtatcgct atctgatgaa aaacctgcgt tctcgcctga tggcgacaca | 1560 |
| ggcatggctg gaagcgcgcc tgaaaggcga agaactgcca aaaccagaag gcctgctgac | 1620 |
| acaaaacgaa gaactgtggg aaccgctcta cgcttgctac cagtcacttc aggcgtgtgg | 1680 |

```
catgggtatt atcgccaacg gcgatctgct cgacaccctg cgccgcgtga aatgtttcgg     1740
cgtaccgctg gtccgtattg atatccgtca ggagagcacg cgtcataccg aagcgctggg     1800
cgagctgacc cgctacctcg gtatcggcga ctacgaaagc tggtcagagg ccgacaaaca     1860
ggcgttcctg atccgcgaac tgaactccaa acgtccgctt ctgccgcgca actggcaacc     1920
aagcgccgaa acgcgcgaag tgctcgatac ctgccaggtg attgccgaag caccgcaagg     1980
ctccattgcc gcctacgtga tctcgatggc gaaaacgccg tccgacgtac tggctgtcca     2040
cctgctgctg aaagaagcgg gtatcgggtt tgcgatgccg gttgctccgc tgtttgaaac     2100
cctcgatgat ctgaacaacg ccaacgatgt catgacccag ctgctcaata ttgactggta     2160
tcgtggcctg attcagggca acagatggt gatgattggc tattccgact cagcaaaaga     2220
tgcgggagtg atggcagctt cctgggcgca atatcaggca caggatgcat taatcaaaac     2280
ctgcgaaaaa gcgggtattg agctgacgtt gttccacggt cgcggcggtt ccattggtcg     2340
cggcggcgca cctgctcatg cggcgctgct gtcacaaccg ccaggaagcc tgaaaggcgg     2400
cctgcgcgta accgaacagg gcgagatgat ccgctttaaa tatggtctgc agaaatcac      2460 cgtcagcagc ctgtcgcttt ataccggggc gattctggaa ccaacctgc tgccaccgcc      2520 ggagccgaaa gagagctggc gtcgcattat ggatgaactg tcagtcatct cctgcgatgt     2580
ctaccgcggc tacgtacgtg aaaacaaaga ttttgtgcct tacttccgct ccgctacgcc     2640
ggaacaagaa ctgggcaaac tgccgttggg ttcacgtccg gcgaaacgtc gcccaaccgg     2700
cggcgtcgag tcactacgcg ccattccgtg gatcttcgcc tggacgcaaa accgtctgat     2760
gctccccgcc tggctgggtg caggtacggc gctgcaaaaa gtggtcgaag acggcaaaca     2820
gagcgagctg gaggctatgt gccgcgattg gccattcttc tcgacgcgtc tcggcatgct     2880
ggagatggtc ttcgccaaag cagacctgtg gctggcggaa tactatgacc aacgcctggt     2940
agacaaagca ctgtggccgt taggtaaaga gttacgcaac ctgcaagaag aagacatcaa     3000
agtggtgctg gcgattgcca acgattccca tctgatggcc gatctgccgt ggattgcaga     3060
gtctattcag ctacggaata tttacaccga cccgctgaac gtattgcagg ccgagttgct     3120
gcaccgctcc cgccaggcag aaaaagaagg ccaggaaccg gaccctcgcg tcgaacaagc     3180
gttaatggtc actattgccg ggattgcggc aggtatgcgt aataccggct aatcttcctc     3240
ttctgcaaac cctcgtgctt ttgcgcgagg tttttctgaa atacttctgt tctaacaccc     3300
tcgttttcaa tatatttctg tctgcatttt attcaaagga tccgtccacc tatgttgact     3360
acatcatcaa ccagatcgat tctgacaaca aactgggcgt aggttcagac gacaccgttg     3420
ctgtgggtat cgtttaccag ttctaatagc acacctcttt gttaaatgcc gaaaaaacag     3480
gactttggtc ctgtttttt tataccttcc agagcaatct cacgtcttgc aaaaacagcc     3540
tgcgttttca tcagtaatag ttggaatttt gtaaatctcc cgttaccctg atagcggact     3600
tcccttctgt aaccataatg gaacctcgtc atgtttgaga acattaccgc cgctcctgcc     3660
gacccgattc tgggcctggc cgatctgttt cgtgccgatg aacgtcccgg caaaattaac     3720
ctcgggattg gtgtctataa agatgagacg ggcaaaaccc cggtactgac cagcgtgaaa     3780
aaggctgaac agtatctgct cgaaaatgaa accaccaaaa attacctcgg cattgacggc     3840
atccctgaat tggtcgctg cactcaggaa ctgctgtttg gtaaaggtag cgccctgatc     3900
aatgacaaac gtgctcgcac ggcacagact ccgggggca ctggcgcact acgcgtggct      3960
gccgatttcc tggcaaaaaa taccagcgtt aagcgtgtgt gggtgagcaa cccaagctgg     4020
```

```
ccgaaccata agagcgtctt taactctgca ggtctggaag ttcgtgaata cgcttattat    4080
gatgcggaaa atcacactct tgacttcgat gcactgatta acagcctgaa tgaagctcag    4140
gctggcgacg tagtgctgtt ccatggctgc tgccataacc caaccggtat cgaccctacg    4200
ctggaacaat ggcaaacact ggcacaactc tccgttgaga aaggctggtt accgctgttt    4260
gacttcgctt accagggttt tgcccgtggt ctggaagaag atgctgaagg actgcgcgct    4320
ttcgcggcta tgcataaaga gctgattgtt gccagttcct actctaaaaa ctttggcctg    4380
tacaacgagc gtgttggcgc ttgtactctg gttgctgccg acagtgaaac cgttgatcgc    4440
gcattcagcc aaatgaaagc ggcgattcgc gctaactact ctaacccacc agcacacggc    4500
gcttctgttg ttgccaccat cctgagcaac gatgcgttac gtgcgatttg gaacaagag     4560 ctgactgata tgcgccagcg tattcagcgt atgcgtcagt tgttcgtcaa tacgctgcag    4620
gaaaaaggcg caaaccgcga cttcagcttt atcatcaaac agaacggcat gttctccttc    4680
agtggcctga caaagaaaca agtgctgcgc ctgcgcgaag agtttggcgt atatgcggtt    4740
gcttctggtc gcgtaaatgt ggccgggatg acaccagata acatggctcc gctgtgcgaa    4800
gcgattgtgg cagtgctgta agcattaaaa acaatgaagc ccgctgaaaa gcgggctgag    4860
actgatgaca aacgcaacat tgcctgatgc gctacgctta tgagctcggt accgagctcg    4920
aattcactgg ccgtcgtttt acaacgtcgt gactgggaaa accctggcgt tacccaactt    4980
aatcgccttg cagcacatcc ccctttcgcc agctggcgta atagcgaaga ggcccgcacc    5040
gatcgccctt cccaacagtt gcgcagcctg aatggcgaat ggcgcctgat gcggtatttt    5100
ctccttacgc atctgtgcgg tatttcacac cgcatatggt gcactctcag tacaatctgc    5160
tctgatgccg catagttaag ccagccccga cacccgccaa cacccgctga cgagcttagt    5220
aaagccctcg ctagatttta atgcggatgt tgcgattact cgccaactat tgcgataac    5280 aagaaaagc cagcctttca tgatatatct cccaatttgt gtagggctta ttatgcacgc    5340
ttaaaaataa taaagcaga cttgacctga tagtttggct gtgagcaatt atgtgcttag    5400
tgcatctaac gcttgagtta agccgcgccg cgaagcggcg tcggcttgaa cgaattgtta    5460
gacattattt gccgactacc ttggtgatct cgcctttcac gtagtggaca aattcttcca    5520
actgatctgc gcgcgaggcc aagcgatctt cttcttgtcc aagataagcc tgtctagctt    5580
caagtatgac gggctgatac tgggccggca ggcgctccat tgcccagtcg gcagcgacat    5640
ccttcggcgc gattttgccg gttactgcgc tgtaccaaat gcgggacaac gtaagcacta    5700
catttcgctc atcgccagcc cagtcgggcg gcgagttcca tagcgttaag gtttcattta    5760
gcgcctcaaa tagatcctgt tcaggaaccg gatcaaagag ttcctccgcc gctggaccta    5820
ccaaggcaac gctatgttct cttgcttttg tcagcaagat agccagatca atgtcgatcg    5880
tggctggctc gaagatacct gcaagaatgt cattgcgctg ccattctcca aattgcagtt    5940
cgcgcttagc tggataacgc cacggaatga tgtcgtcgtg cacaacaatg gtgacttcta    6000
cagcgcggag aatctcgctc tctccagggg aagccgaagt ttccaaaagg tcgttgatca    6060
aagctcgccg cgttgtttca tcaagcctta cggtcaccgt aaccagcaaa tcaatatcac    6120
tgtgtggctt caggccgcca tccactgcgg agccgtacaa atgtacggcc agcaacgtcg    6180
gttcgagatg gcgctcgatg acgccaacta cctctgatag ttgagtcgat acttcggcga    6240
tcaccgcttc cctcatgatg tttaactttg ttttagggcg actgccctgc tgcgtaacat    6300
cgttgctgct ccataacatc aaacatcgac ccacggcgta acgcgcttgc tgcttggatg    6360
cccgaggcat agactgtacc ccaaaaaaac agtcataaca agccatgaaa accgccactg    6420
```

```
cgccgttacc accgctgcgt tcggtcaagg ttctggacca gttgcgtgag cgcatacgct   6480
acttgcatta cagcttacga accgaacagg cttatgtcca ctgggttcgt gccttcatcc   6540
gtttccacgg tgtgcgtcac ccggcaacct gggcagcag cgaagtcgag gcatttctgt   6600
cctggctggc gaacgagcgc aaggtttcgg tctccacgca tcgtcaggca ttggcggcct   6660
tgctgttctt ctacggcaag gtgctgtgca cggatctgcc ctggcttcag gagatcggaa   6720
gacctcggcc gtcgcggcgc ttgccggtgg tgctgacccc ggatgaagtg gttcgcatcc   6780
tcggttttct ggaaggcgag catcgtttgt tcgcccagct tctgtatgga acgggcatgc   6840
ggatcagtga gggtttgcaa ctgcgggtca aggatctgga tttcgatcac ggcacgatca   6900
tcgtgcggga gggcaagggc tccaaggatc gggccttgat gttacccgag agcttggcac   6960
ccagcctgcg cgagcagggg aattaattcc cacgggtttt gctgcccgca acgggctgt    7020 tctggtgttg ctagtttgtt atcagaatcg cagatccggc ttcagccggt ttgccggctg   7080
aaagcgctat ttcttccaga attgccatga ttttttcccc acgggaggcg tcactggctc   7140
ccgtgttgtc ggcagctttg attcgataag cagcatcgcc tgtttcaggc tgtctatgtg   7200
tgactgttga gctgtaacaa gttgtctcag gtgttcaatt tcatgttcta gttgctttgt   7260
tttactggtt tcacctgttc tattaggtgt tacatgctgt tcatctgtta cattgtcgat   7320
ctgttcatgg tgaacagctt tgaatgcacc aaaaactcgt aaaagctctg atgtatctat   7380
cttttttaca ccgttttcat ctgtgcatat ggacagtttt cccttttgata tgtaacggtg   7440 aacagttgtt ctactttgt tgttagtct tgatgcttca ctgatagata caagagccat     7500
aagaacctca gatccttccg tatttagcca gtatgttctc tagtgtggtt cgttgttttt   7560
gcgtgagcca tgagaacgaa ccattggaga tcatacttact ttgcatgtca ctcaaaaatt   7620
ttgcctcaaa actggtgagc tgaattttg cagttaaagc atcgtgtagt gtttttctta    7680
gtccgttatg taggtaggaa tctgatgtaa tggttgttgg tatttgtca ccattcattt     7740 ttatctggtt gttctcaagt tcggttacga gatccatttg tctatctagt tcaacttgga   7800
aaatcaacgt atcagtcggg cggcctcgct tatcaaccac caatttcata ttgctgtaag   7860
tgtttaaatc tttacttatt ggtttcaaaa cccattggtt aagccttta aactcatggt    7920 agttattttc aagcattaac atgaacttaa attcatcaag gctaatctct atatttgcct   7980
tgtgagtttt cttttgtgtt agttcttta ataccactc ataaatcctc atagagtatt     8040
tgttttcaaa agacttaaca tgttccagat tatattttat gaattttttt aactggaaaa   8100
gataaggcaa tatctcttca ctaaaaacta attctaattt ttcgcttgag aacttggcat   8160
agtttgtcca ctggaaaatc tcaaagcctt taaccaaagg attcctgatt tccacagttc   8220
tcgtcatcag ctctctggtt gctttagcta atacaccata agcattttcc ctactgatgt   8280
tcatcatctg agcgtattgg ttataagtga acgataccgt ccgttctttc cttgtagggt   8340
tttcaatcgt ggggttgagt agtgccacac agcataaaat tagcttggtt tcatgctccg   8400
ttaagtcata gcgactaatc gctagttcat ttgctttgaa acaactaat tcagacatac    8460 atctcaattg gtctaggtga ttttaatcac tataccaatt gagatgggct agtcaatgat   8520
aattactagt ccttttcctt tgagttgtgg gtatctgtaa attctgctag acctttgctg   8580
gaaaacttgt aaattctgct agaccctctg taaattccgc tagacctttg tgtgttttt    8640 ttgtttatat tcaagtggtt ataatttata gaataaagaa agaataaaaa aagataaaaa   8700
gaatagatcc cagccctgtg tataactcac tactttagtc agttccgcag tattacaaaa   8760
```

```
ggatgtcgca aacgctgttt gctcctctac aaaacagacc ttaaaccct aaaggcttaa    8820 gtagcaccct cgcaagctcg ggcaaatcgc tgaatattcc ttttgtctcc gaccatcagg    8880
cacctgagtc gctgtctttt tcgtgacatt cagttcgctg cgctcacggc tctggcagtg    8940
aatgggggta atggcacta caggcgcctt ttatggattc atgcaaggaa actacccata    9000
atacaagaaa agcccgtcac gggcttctca gggcgtttta tggcgggtct gctatgtggt    9060
gctatctgac ttttttgctgt tcagcagttc ctgccctctg attttccagt ctgaccactt    9120
cggattatcc cgtgacaggt cattcagact ggctaatgca cccagtaagg cagcggtatc    9180
atcaacaggc tta                                                       9193
```

<210> SEQ ID NO 42
<211> LENGTH: 540
<212> TYPE: PRT
<213> ORGANISM: Escherichia coli W3110
<220> FEATURE:
<221> NAME/KEY: PEPTIDE
<222> LOCATION: (1)..(540)
<223> OTHER INFORMATION: NadB - aspartate oxidase

<400> SEQUENCE: 42

```
Met Asn Thr Leu Pro Glu His Ser Cys Asp Val Leu Ile Ile Gly Ser
  1               5                  10                  15

Gly Ala Ala Gly Leu Ser Leu Ala Leu Arg Leu Ala Asp Gln His Gln
                 20                  25                  30

Val Ile Val Leu Ser Lys Gly Pro Val Thr Glu Gly Ser Thr Phe Tyr
             35                  40                  45

Ala Gln Gly Gly Ile Ala Ala Val Phe Asp Glu Thr Asp Ser Ile Asp
         50                  55                  60

Ser His Val Glu Asp Thr Leu Ile Ala Gly Ala Gly Ile Cys Asp Arg
     65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270
```

```
Asp Gly Thr Arg Phe Met Pro Asp Phe Asp Glu Arg Gly Glu Leu Ala
            275                 280                 285

Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
    450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg
    530                 535                 540

<210> SEQ ID NO 43
<211> LENGTH: 347
<212> TYPE: PRT
<213> ORGANISM: Escherichia coli W3110
<220> FEATURE:
<221> NAME/KEY: PEPTIDE
<222> LOCATION: (1)..(347)
<223> OTHER INFORMATION: NadA - quinolinate sythase

<400> SEQUENCE: 43

Met Ser Val Met Phe Asp Pro Asp Thr Ala Ile Tyr Pro Phe Pro Pro
1               5                   10                  15

Lys Pro Thr Pro Leu Ser Ile Asp Glu Lys Ala Tyr Tyr Arg Glu Lys
            20                  25                  30

Ile Lys Arg Leu Leu Lys Glu Arg Asn Ala Val Met Val Ala His Tyr
        35                  40                  45

Tyr Thr Asp Pro Glu Ile Gln Gln Leu Ala Glu Thr Gly Gly Cys
    50                  55                  60

Ile Ser Asp Ser Leu Glu Met Ala Arg Phe Gly Ala Lys His Pro Ala
65                  70                  75                  80

Ser Thr Leu Leu Val Ala Gly Val Arg Phe Met Gly Glu Thr Ala Lys
```

```
            85                  90                  95
Ile Leu Ser Pro Glu Lys Thr Ile Leu Met Pro Thr Leu Gln Ala Glu
            100                 105                 110

Cys Ser Leu Asp Leu Gly Cys Pro Val Glu Glu Phe Asn Ala Phe Cys
            115                 120                 125

Asp Ala His Pro Asp Arg Thr Val Val Tyr Ala Asn Thr Ser Ala
            130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
            165                 170                 175

Pro Asp Lys His Leu Gly Arg Tyr Val Gln Lys Gln Thr Gly Gly Asp
            180                 185                 190

Ile Leu Cys Trp Gln Gly Ala Cys Ile Val His Asp Glu Phe Lys Thr
            195                 200                 205

Gln Ala Leu Thr Arg Leu Gln Glu Glu Tyr Pro Asp Ala Ala Ile Leu
            210                 215                 220

Val His Pro Glu Ser Pro Gln Ala Ile Val Asp Met Ala Asp Ala Val
225                 230                 235                 240

Gly Ser Thr Ser Gln Leu Ile Ala Ala Lys Thr Leu Pro His Gln
            245                 250                 255

Arg Leu Ile Val Ala Thr Asp Arg Gly Ile Phe Tyr Lys Met Gln Gln
            260                 265                 270

Ala Val Pro Asp Lys Glu Leu Leu Glu Ala Pro Thr Ala Gly Glu Gly
            275                 280                 285

Ala Thr Cys Arg Ser Cys Ala His Cys Pro Trp Met Ala Met Asn Gly
            290                 295                 300

Leu Gln Ala Ile Ala Glu Ala Leu Glu Gln Gly Ser Asn His Glu
305                 310                 315                 320

Val His Val Asp Glu Arg Leu Arg Glu Arg Ala Leu Val Pro Leu Asn
            325                 330                 335

Arg Met Leu Asp Phe Ala Ala Thr Leu Arg Gly
            340                 345

<210> SEQ ID NO 44
<211> LENGTH: 297
<212> TYPE: PRT
<213> ORGANISM: Escherichia coli W3110
<220> FEATURE:
<221> NAME/KEY: PEPTIDE
<222> LOCATION: (1)..(297)
<223> OTHER INFORMATION: NadC - quinolinate phosphoribosyltransferase

<400> SEQUENCE: 44

Met Pro Pro Arg Arg Tyr Asn Pro Asp Thr Arg Arg Asp Glu Leu Leu
1               5                   10                  15

Glu Arg Ile Asn Leu Asp Ile Pro Gly Ala Val Ala Gln Ala Leu Arg
            20                  25                  30

Glu Asp Leu Gly Gly Thr Val Asp Ala Asn Asn Asp Ile Thr Ala Lys
        35                  40                  45

Leu Leu Pro Glu Asn Ser Arg Ser His Ala Thr Val Ile Thr Arg Glu
    50                  55                  60

Asn Gly Val Phe Cys Gly Lys Arg Trp Val Glu Glu Val Phe Ile Gln
65              70                  75                  80

Leu Ala Gly Asp Asp Val Thr Ile Ile Trp His Val Asp Gly Asp
            85                  90                  95
```

```
Val Ile Asn Ala Asn Gln Ser Leu Phe Glu Leu Glu Gly Pro Ser Arg
            100                 105                 110

Val Leu Leu Thr Gly Glu Arg Thr Ala Leu Asn Phe Val Gln Thr Leu
            115                 120                 125

Ser Gly Val Ala Ser Lys Val Arg His Tyr Val Glu Leu Leu Glu Gly
            130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Ala Asn His Arg
                165                 170                 175

Leu Gly Leu Ser Asp Ala Phe Leu Ile Lys Glu Asn His Ile Ile Ala
            180                 185                 190

Ser Gly Ser Val Arg Gln Ala Val Glu Lys Ala Ser Trp Leu His Pro
            195                 200                 205

Asp Ala Pro Val Glu Val Glu Val Asn Leu Glu Glu Leu Asp Glu
            210                 215                 220

Ala Leu Lys Ala Gly Ala Asp Ile Ile Met Leu Asp Asn Phe Glu Thr
225                 230                 235                 240

Glu Gln Met Arg Glu Ala Val Lys Arg Thr Asn Gly Lys Ala Leu Leu
                245                 250                 255

Glu Val Ser Gly Asn Val Thr Asp Lys Thr Leu Arg Glu Phe Ala Glu
            260                 265                 270

Thr Gly Val Asp Phe Ile Ser Val Gly Ala Leu Thr Lys His Val Gln
            275                 280                 285

Ala Leu Asp Leu Ser Met Arg Phe Arg
            290                 295

<210> SEQ ID NO 45
<211> LENGTH: 883
<212> TYPE: PRT
<213> ORGANISM: Escherichia coli W3110
<220> FEATURE:
<221> NAME/KEY: PEPTIDE
<222> LOCATION: (1)..(883)
<223> OTHER INFORMATION: Ppc - Phosphoenolpyruvate carboxylase

<400> SEQUENCE: 45

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
            115                 120                 125

Leu Ser Leu Glu Leu Val Leu Thr Ala His Pro Thr Glu Ile Thr Arg
            130                 135                 140
```

```
Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
```

565                 570                 575
Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
            595                 600                 605

Arg Val Thr Glu Gln Gly Glu Met Ile Arg Phe Lys Tyr Gly Leu Pro
            610                 615                 620

Glu Ile Thr Val Ser Ser Leu Ser Leu Tyr Thr Gly Ala Ile Leu Glu
625                 630                 635                 640

Ala Asn Leu Leu Pro Pro Glu Pro Lys Glu Ser Trp Arg Arg Ile
            645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
            675                 680                 685

Gln Glu Leu Gly Lys Leu Pro Leu Gly Ser Arg Pro Ala Lys Arg Arg
            690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
            725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
            755                 760                 765

Met Val Phe Ala Lys Ala Asp Leu Trp Leu Ala Glu Tyr Tyr Asp Gln
            770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
            805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
            835                 840                 845

Arg Ser Arg Gln Ala Glu Lys Glu Gly Gln Glu Pro Asp Pro Arg Val
            850                 855                 860

Glu Gln Ala Leu Met Val Thr Ile Ala Gly Ile Ala Ala Gly Met Arg
865                 870                 875                 880

Asn Thr Gly

<210> SEQ ID NO 46
<211> LENGTH: 396
<212> TYPE: PRT
<213> ORGANISM: Escherichia coli W3110
<220> FEATURE:
<221> NAME/KEY: PEPTIDE
<222> LOCATION: (1)..(396)
<223> OTHER INFORMATION: AspC - Aspartate aminotransferase

<400> SEQUENCE: 46

Met Phe Glu Asn Ile Thr Ala Ala Pro Ala Asp Pro Ile Leu Gly Leu
 1               5                  10                  15

Ala Asp Leu Phe Arg Ala Asp Glu Arg Pro Gly Lys Ile Asn Leu Gly
            20                  25                  30

```
Ile Gly Val Tyr Lys Asp Glu Thr Gly Lys Thr Pro Val Leu Thr Ser
            35                  40                  45

Val Lys Lys Ala Glu Gln Tyr Leu Leu Glu Asn Glu Thr Thr Lys Asn
 50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
                100                 105                 110

Phe Leu Ala Lys Asn Thr Ser Val Lys Arg Val Trp Val Ser Asn Pro
                115                 120                 125

Ser Trp Pro Asn His Lys Ser Val Phe Asn Ser Ala Gly Leu Glu Val
130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
                180                 185                 190

Gln Trp Gln Thr Leu Ala Gln Leu Ser Val Glu Lys Gly Trp Leu Pro
                195                 200                 205

Leu Phe Asp Phe Ala Tyr Gln Gly Phe Ala Arg Gly Leu Glu Glu Asp
                210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
                260                 265                 270

Ser Gln Met Lys Ala Ala Ile Arg Ala Asn Tyr Ser Asn Pro Pro Ala
                275                 280                 285

His Gly Ala Ser Val Val Ala Thr Ile Leu Ser Asn Asp Ala Leu Arg
                290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
                340                 345                 350

Leu Thr Lys Glu Gln Val Leu Arg Leu Arg Glu Glu Phe Gly Val Tyr
                355                 360                 365

Ala Val Ala Ser Gly Arg Val Asn Val Ala Gly Met Thr Pro Asp Asn
                370                 375                 380

Met Ala Pro Leu Cys Glu Ala Ile Val Ala Val Leu
385                 390                 395

<210> SEQ ID NO 47
<211> LENGTH: 900
<212> TYPE: PRT
<213> ORGANISM: Escherichia coli W3110
<220> FEATURE:
<221> NAME/KEY: PEPTIDE
<222> LOCATION: (1)..(900)
<223> OTHER INFORMATION: Fusion protein - Aspartate oxidase-HL1-
      Quinolinate sythase
```

```
<400> SEQUENCE: 47

Met Asn Thr Leu Pro Glu His Ser Cys Asp Val Leu Ile Ile Gly Ser
 1               5                  10                  15

Gly Ala Ala Gly Leu Ser Leu Ala Leu Arg Leu Ala Asp Gln His Gln
                20                  25                  30

Val Ile Val Leu Ser Lys Gly Pro Val Thr Glu Gly Ser Thr Phe Tyr
            35                  40                  45

Ala Gln Gly Gly Ile Ala Ala Val Phe Asp Glu Thr Asp Ser Ile Asp
        50                  55                  60

Ser His Val Glu Asp Thr Leu Ile Ala Gly Ala Gly Ile Cys Asp Arg
65                  70                  75                  80

His Ala Val Glu Phe Val Ala Ser Asn Ala Arg Ser Cys Val Gln Trp
                85                  90                  95

Leu Ile Asp Gln Gly Val Leu Phe Asp Thr His Ile Gln Pro Asn Gly
                100                 105                 110

Glu Glu Ser Tyr His Leu Thr Arg Gly Gly His Ser His Arg Arg
                115                 120                 125

Ile Leu His Ala Ala Asp Ala Thr Gly Arg Glu Val Glu Thr Thr Leu
        130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
                180                 185                 190

Glu Thr Cys His Ala Lys Ala Val Val Leu Ala Thr Gly Gly Ala Ser
                195                 200                 205

Lys Val Tyr Gln Tyr Thr Thr Asn Pro Asp Ile Ser Ser Gly Asp Gly
        210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
                260                 265                 270

Asp Gly Thr Arg Phe Met Pro Asp Phe Asp Glu Arg Gly Glu Leu Ala
            275                 280                 285

Pro Arg Asp Ile Val Ala Arg Ala Ile Asp His Glu Met Lys Arg Leu
        290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
```

```
                405                 410                 415
Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
            435                 440                 445

Asp Tyr Val Gly Ile Val Arg Thr Thr Lys Arg Leu Glu Arg Ala Leu
            450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
            485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
            515                 520                 525

Ser Ile Leu Ser Pro Gly Asn His Tyr Ile Asn Arg Ile Leu Ala Glu
            530                 535                 540

Ala Ala Lys Ala Ala Ala Leu Gln Met Ser Val Met Phe Asp Pro
545                 550                 555                 560

Asp Thr Ala Ile Tyr Pro Phe Pro Pro Lys Pro Thr Pro Leu Ser Ile
                565                 570                 575

Asp Glu Lys Ala Tyr Tyr Arg Glu Lys Ile Lys Arg Leu Leu Lys Glu
            580                 585                 590

Arg Asn Ala Val Met Val Ala His Tyr Tyr Thr Asp Pro Glu Ile Gln
            595                 600                 605

Gln Leu Ala Glu Glu Thr Gly Gly Cys Ile Ser Asp Ser Leu Glu Met
            610                 615                 620

Ala Arg Phe Gly Ala Lys His Pro Ala Ser Thr Leu Leu Val Ala Gly
625                 630                 635                 640

Val Arg Phe Met Gly Glu Thr Ala Lys Ile Leu Ser Pro Glu Lys Thr
                645                 650                 655

Ile Leu Met Pro Thr Leu Gln Ala Glu Cys Ser Leu Asp Leu Gly Cys
            660                 665                 670

Pro Val Glu Glu Phe Asn Ala Phe Cys Asp Ala His Pro Asp Arg Thr
            675                 680                 685

Val Val Val Tyr Ala Asn Thr Ser Ala Ala Val Lys Ala Arg Ala Asp
            690                 695                 700

Trp Val Val Thr Ser Ser Ile Ala Val Glu Leu Ile Asp His Leu Asp
705                 710                 715                 720

Ser Leu Gly Glu Lys Ile Ile Trp Ala Pro Asp Lys His Leu Gly Arg
                725                 730                 735

Tyr Val Gln Lys Gln Thr Gly Gly Asp Ile Leu Cys Trp Gln Gly Ala
            740                 745                 750

Cys Ile Val His Asp Glu Phe Lys Thr Gln Ala Leu Thr Arg Leu Gln
            755                 760                 765

Glu Glu Tyr Pro Asp Ala Ala Ile Leu Val His Pro Glu Ser Pro Gln
            770                 775                 780

Ala Ile Val Asp Met Ala Asp Ala Val Gly Ser Thr Ser Gln Leu Ile
785                 790                 795                 800

Ala Ala Ala Lys Thr Leu Pro His Gln Arg Leu Ile Val Ala Thr Asp
                805                 810                 815

Arg Gly Ile Phe Tyr Lys Met Gln Gln Ala Val Pro Asp Lys Glu Leu
            820                 825                 830
```

-continued

Leu Glu Ala Pro Thr Ala Gly Glu Gly Ala Thr Cys Arg Ser Cys Ala
                835                 840                 845

His Cys Pro Trp Met Ala Met Asn Gly Leu Gln Ala Ile Ala Glu Ala
        850                 855                 860

Leu Glu Gln Glu Gly Ser Asn His Glu Val His Val Asp Glu Arg Leu
865                 870                 875                 880

Arg Glu Arg Ala Leu Val Pro Leu Asn Arg Met Leu Asp Phe Ala Ala
                885                 890                 895

Thr Leu Arg Gly
            900

<210> SEQ ID NO 48
<211> LENGTH: 905
<212> TYPE: PRT
<213> ORGANISM: Escherichia coli W3110
<220> FEATURE:
<221> NAME/KEY: PEPTIDE
<222> LOCATION: (1)..(905)
<223> OTHER INFORMATION: Fusion protein - Aspartate oxidase-HL2-
      Quinolinate sythase

<400> SEQUENCE: 48

Met Asn Thr Leu Pro Glu His Ser Cys Asp Val Leu Ile Ile Gly Ser
  1               5                  10                  15

Gly Ala Ala Gly Leu Ser Leu Ala Leu Arg Leu Ala Asp Gln His Gln
             20                  25                  30

Val Ile Val Leu Ser Lys Gly Pro Val Thr Glu Gly Ser Thr Phe Tyr
         35                  40                  45

Ala Gln Gly Gly Ile Ala Ala Val Phe Asp Glu Thr Asp Ser Ile Asp
     50                  55                  60

Ser His Val Glu Asp Thr Leu Ile Ala Gly Ala Gly Ile Cys Asp Arg
 65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270

```
Asp Gly Thr Arg Phe Met Pro Asp Phe Asp Glu Arg Gly Glu Leu Ala
            275                 280                 285

Pro Arg Asp Ile Val Ala Arg Ala Ile Asp His Glu Met Lys Arg Leu
290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
    450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg Ile Leu Ala Glu
    530                 535                 540

Ala Ala Lys Glu Ala Ala Lys Ala Ala Ala Leu Gln Met Ser
545                 550                 555                 560

Val Met Phe Asp Pro Asp Thr Ala Ile Tyr Pro Phe Pro Lys Pro
                565                 570                 575

Thr Pro Leu Ser Ile Asp Glu Lys Ala Tyr Tyr Arg Glu Lys Ile Lys
            580                 585                 590

Arg Leu Leu Lys Glu Arg Asn Ala Val Met Val Ala His Tyr Tyr Thr
        595                 600                 605

Asp Pro Glu Ile Gln Gln Leu Ala Glu Thr Gly Gly Cys Ile Ser
    610                 615                 620

Asp Ser Leu Glu Met Ala Arg Phe Gly Ala Lys His Pro Ala Ser Thr
625                 630                 635                 640

Leu Leu Val Ala Gly Val Arg Phe Met Gly Glu Thr Ala Lys Ile Leu
                645                 650                 655

Ser Pro Glu Lys Thr Ile Leu Met Pro Thr Leu Gln Ala Glu Cys Ser
            660                 665                 670

Leu Asp Leu Gly Cys Pro Val Glu Glu Phe Asn Ala Phe Cys Asp Ala
        675                 680                 685
```

```
His Pro Asp Arg Thr Val Val Val Tyr Ala Asn Thr Ser Ala Ala Val
            690             695             700

Lys Ala Arg Ala Asp Trp Val Val Thr Ser Ser Ile Ala Val Glu Leu
705             710             715             720

Ile Asp His Leu Asp Ser Leu Gly Glu Lys Ile Ile Trp Ala Pro Asp
            725             730             735

Lys His Leu Gly Arg Tyr Val Gln Lys Gln Thr Gly Gly Asp Ile Leu
            740             745             750

Cys Trp Gln Gly Ala Cys Ile Val His Asp Glu Phe Lys Thr Gln Ala
            755             760             765

Leu Thr Arg Leu Gln Glu Glu Tyr Pro Asp Ala Ala Ile Leu Val His
770             775             780

Pro Glu Ser Pro Gln Ala Ile Val Asp Met Ala Asp Ala Val Gly Ser
785             790             795             800

Thr Ser Gln Leu Ile Ala Ala Lys Thr Leu Pro His Gln Arg Leu
            805             810             815

Ile Val Ala Thr Asp Arg Gly Ile Phe Tyr Lys Met Gln Gln Ala Val
            820             825             830

Pro Asp Lys Glu Leu Leu Glu Ala Pro Thr Ala Gly Glu Gly Ala Thr
835             840             845

Cys Arg Ser Cys Ala His Cys Pro Trp Met Ala Met Asn Gly Leu Gln
850             855             860

Ala Ile Ala Glu Ala Leu Glu Gln Glu Gly Ser Asn His Glu Val His
865             870             875             880

Val Asp Glu Arg Leu Arg Glu Arg Ala Leu Val Pro Leu Asn Arg Met
            885             890             895

Leu Asp Phe Ala Ala Thr Leu Arg Gly
            900             905

<210> SEQ ID NO 49
<211> LENGTH: 910
<212> TYPE: PRT
<213> ORGANISM: Escherichia coli W3110
<220> FEATURE:
<221> NAME/KEY: PEPTIDE
<222> LOCATION: (1)..(910)
<223> OTHER INFORMATION: Fusion protein - Aspartate oxidase-HL3-
      Quinolinate sythase

<400> SEQUENCE: 49

Met Asn Thr Leu Pro Glu His Ser Cys Asp Val Leu Ile Ile Gly Ser
1               5               10              15

Gly Ala Ala Gly Leu Ser Leu Ala Leu Arg Leu Ala Asp Gln His Gln
            20              25              30

Val Ile Val Leu Ser Lys Gly Pro Val Thr Glu Gly Ser Thr Phe Tyr
        35              40              45

Ala Gln Gly Gly Ile Ala Ala Val Phe Asp Glu Thr Asp Ser Ile Asp
    50              55              60

Ser His Val Glu Asp Thr Leu Ile Ala Gly Ala Gly Ile Cys Asp Arg
65              70              75              80

His Ala Val Glu Phe Val Ala Ser Asn Ala Arg Ser Cys Val Gln Trp
                85              90              95

Leu Ile Asp Gln Gly Val Leu Phe Asp Thr His Ile Gln Pro Asn Gly
            100             105             110

Glu Glu Ser Tyr His Leu Thr Arg Glu Gly Gly His Ser His Arg Arg
        115             120             125
```

Ile Leu His Ala Ala Asp Ala Thr Gly Arg Glu Val Glu Thr Thr Leu
130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
            165                 170                 175

Arg Arg Val Val Gly Ala Trp Val Trp Asn Arg Asn Lys Glu Thr Val
            180                 185                 190

Glu Thr Cys His Ala Lys Ala Val Leu Ala Thr Gly Gly Ala Ser
        195                 200                 205

Lys Val Tyr Gln Tyr Thr Thr Asn Pro Asp Ile Ser Ser Gly Asp Gly
210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
            245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
            275                 280                 285

Pro Arg Asp Ile Val Ala Arg Ala Ile Asp His Glu Met Lys Arg Leu
290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
            325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
            355                 360                 365

Gly Leu Tyr Ala Ile Gly Glu Val Ser Tyr Thr Gly Leu His Gly Ala
370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
            405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
            435                 440                 445

Asp Tyr Val Gly Ile Val Arg Thr Thr Lys Arg Leu Glu Arg Ala Leu
450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
            485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
            515                 520                 525

Ser Ile Leu Ser Pro Gly Asn His Tyr Ile Asn Arg Ile Leu Ala Glu
530                 535                 540

Ala Ala Ala Lys Glu Ala Ala Ala Lys Glu Ala Ala Ala Lys Ala Ala

Ala Leu Gln Met Ser Val Met Phe Asp Pro Asp Thr Ala Ile Tyr Pro
545                 550                 555                 560

Phe Pro Pro Lys Pro Thr Pro Leu Ser Ile Asp Glu Lys Ala Tyr Tyr
            565                 570                 575

Arg Glu Lys Ile Lys Arg Leu Leu Lys Glu Arg Asn Ala Val Met Val
        580                 585                 590

Ala His Tyr Tyr Thr Asp Pro Glu Ile Gln Gln Leu Ala Glu Glu Thr
    595                 600                 605

Gly Gly Cys Ile Ser Asp Ser Leu Glu Met Ala Arg Phe Gly Ala Lys
610                 615                 620

His Pro Ala Ser Thr Leu Leu Val Ala Gly Val Arg Phe Met Gly Glu
625                 630                 635                 640

Thr Ala Lys Ile Leu Ser Pro Glu Lys Thr Ile Leu Met Pro Thr Leu
            645                 650                 655

Gln Ala Glu Cys Ser Leu Asp Leu Gly Cys Pro Val Glu Glu Phe Asn
        660                 665                 670

Ala Phe Cys Asp Ala His Pro Asp Arg Thr Val Val Tyr Ala Asn
    675                 680                 685

Thr Ser Ala Ala Val Lys Ala Arg Ala Asp Trp Val Val Thr Ser Ser
690                 695                 700

Ile Ala Val Glu Leu Ile Asp His Leu Asp Ser Leu Gly Glu Lys Ile
705                 710                 715                 720

Ile Trp Ala Pro Asp Lys His Leu Gly Arg Tyr Val Gln Lys Gln Thr
            725                 730                 735

Gly Gly Asp Ile Leu Cys Trp Gln Gly Ala Cys Ile Val His Asp Glu
        740                 745                 750

Phe Lys Thr Gln Ala Leu Thr Arg Leu Gln Glu Tyr Pro Asp Ala
    755                 760                 765

Ala Ile Leu Val His Pro Glu Ser Pro Gln Ala Ile Val Asp Met Ala
770                 775                 780

Asp Ala Val Gly Ser Thr Ser Gln Leu Ile Ala Ala Lys Thr Leu
785                 790                 795                 800

Pro His Gln Arg Leu Ile Val Ala Thr Asp Arg Gly Ile Phe Tyr Lys
            805                 810                 815

Met Gln Gln Ala Val Pro Asp Lys Glu Leu Leu Glu Ala Pro Thr Ala
        820                 825                 830

Gly Glu Gly Ala Thr Cys Arg Ser Cys Ala His Cys Pro Trp Met
    835                 840                 845

Met Asn Gly Leu Gln Ala Ile Ala Glu Ala Leu Glu Gln Glu Gly Ser
850                 855                 860

Asn His Glu Val His Val Asp Glu Arg Leu Arg Glu Arg Ala Leu Val
865                 870                 875                 880

Pro Leu Asn Arg Met Leu Asp Phe Ala Ala Thr Leu Arg Gly
            885                 890                 895

900                 905                 910

<210> SEQ ID NO 50
<211> LENGTH: 915
<212> TYPE: PRT
<213> ORGANISM: Escherichia coli W3110
<220> FEATURE:
<221> NAME/KEY: PEPTIDE
<222> LOCATION: (1)..(915)
<223> OTHER INFORMATION: Fusion protein - Aspartate oxidase-HL4-
      Quinolinate sythase

```
<400> SEQUENCE: 50

Met Asn Thr Leu Pro Glu His Ser Cys Asp Val Leu Ile Ile Gly Ser
  1               5                  10                  15

Gly Ala Ala Gly Leu Ser Leu Ala Leu Arg Leu Ala Asp Gln His Gln
             20                  25                  30

Val Ile Val Leu Ser Lys Gly Pro Val Thr Glu Gly Ser Thr Phe Tyr
         35                  40                  45

Ala Gln Gly Gly Ile Ala Ala Val Phe Asp Thr Asp Ser Ile Asp
     50                  55                  60

Ser His Val Glu Asp Thr Leu Ile Ala Gly Ala Gly Ile Cys Asp Arg
 65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285

Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415
```

```
Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
            435                 440                 445

Asp Tyr Val Gly Ile Val Arg Thr Thr Lys Arg Leu Glu Arg Ala Leu
            450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
            515                 520                 525

Ser Ile Leu Ser Pro Gly Asn His Tyr Ile Asn Arg Ile Leu Ala Glu
            530                 535                 540

Ala Ala Lys Glu Ala Ala Lys Glu Ala Ala Lys Glu Ala
545                 550                 555                 560

Ala Ala Lys Ala Ala Leu Gln Met Ser Val Met Phe Asp Pro Asp
            565                 570                 575

Thr Ala Ile Tyr Pro Phe Pro Lys Pro Thr Pro Leu Ser Ile Asp
            580                 585                 590

Glu Lys Ala Tyr Tyr Arg Glu Lys Ile Lys Arg Leu Leu Lys Glu Arg
            595                 600                 605

Asn Ala Val Met Val Ala His Tyr Tyr Thr Asp Pro Glu Ile Gln Gln
            610                 615                 620

Leu Ala Glu Glu Thr Gly Gly Cys Ile Ser Asp Ser Leu Glu Met Ala
625                 630                 635                 640

Arg Phe Gly Ala Lys His Pro Ala Ser Thr Leu Leu Val Ala Gly Val
            645                 650                 655

Arg Phe Met Gly Glu Thr Ala Lys Ile Leu Ser Pro Glu Lys Thr Ile
            660                 665                 670

Leu Met Pro Thr Leu Gln Ala Glu Cys Ser Leu Asp Leu Gly Cys Pro
            675                 680                 685

Val Glu Glu Phe Asn Ala Phe Cys Asp Ala His Pro Asp Arg Thr Val
            690                 695                 700

Val Val Tyr Ala Asn Thr Ser Ala Ala Val Lys Ala Arg Ala Asp Trp
705                 710                 715                 720

Val Val Thr Ser Ser Ile Ala Val Glu Leu Ile Asp His Leu Asp Ser
            725                 730                 735

Leu Gly Glu Lys Ile Ile Trp Ala Pro Asp Lys His Leu Gly Arg Tyr
            740                 745                 750

Val Gln Lys Gln Thr Gly Gly Asp Ile Leu Cys Trp Gln Gly Ala Cys
            755                 760                 765

Ile Val His Asp Glu Phe Lys Thr Gln Ala Leu Thr Arg Leu Gln Glu
            770                 775                 780

Glu Tyr Pro Asp Ala Ala Ile Leu Val His Pro Glu Ser Pro Gln Ala
785                 790                 795                 800

Ile Val Asp Met Ala Asp Ala Val Gly Ser Thr Ser Gln Leu Ile Ala
            805                 810                 815

Ala Ala Lys Thr Leu Pro His Gln Arg Leu Ile Val Ala Thr Asp Arg
            820                 825                 830
```

```
Gly Ile Phe Tyr Lys Met Gln Gln Ala Val Pro Asp Lys Glu Leu Leu
            835                 840                 845

Glu Ala Pro Thr Ala Gly Glu Gly Ala Thr Cys Arg Ser Cys Ala His
850                 855                 860

Cys Pro Trp Met Ala Met Asn Gly Leu Gln Ala Ile Ala Glu Ala Leu
865                 870                 875                 880

Glu Gln Glu Gly Ser Asn His Glu Val His Val Asp Glu Arg Leu Arg
                885                 890                 895

Glu Arg Ala Leu Val Pro Leu Asn Arg Met Leu Asp Phe Ala Ala Thr
            900                 905                 910

Leu Arg Gly
        915

<210> SEQ ID NO 51
<211> LENGTH: 920
<212> TYPE: PRT
<213> ORGANISM: Escherichia coli W3110
<220> FEATURE:
<221> NAME/KEY: PEPTIDE
<222> LOCATION: (1)..(920)
<223> OTHER INFORMATION: Fusion protein - Aspartate oxidase-HL5-
      Quinolinate sythase

<400> SEQUENCE: 51

Met Asn Thr Leu Pro Glu His Ser Cys Asp Val Leu Ile Ile Gly Ser
1               5                   10                  15

Gly Ala Ala Gly Leu Ser Leu Ala Leu Arg Leu Ala Asp Gln His Gln
            20                  25                  30

Val Ile Val Leu Ser Lys Gly Pro Val Thr Glu Gly Ser Thr Phe Tyr
        35                  40                  45

Ala Gln Gly Gly Ile Ala Ala Val Phe Asp Glu Thr Asp Ser Ile Asp
    50                  55                  60

Ser His Val Glu Asp Thr Leu Ile Ala Gly Ala Gly Ile Cys Asp Arg
65                  70                  75                  80

His Ala Val Glu Phe Val Ala Ser Asn Ala Arg Ser Cys Val Gln Trp
                85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255
```

```
Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285

Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
    450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg Ile Leu Ala Glu
    530                 535                 540

Ala Ala Ala Lys Glu Ala Ala Lys Glu Ala Ala Lys Glu Ala
545                 550                 555                 560

Ala Ala Lys Glu Ala Ala Lys Ala Ala Leu Gln Met Ser Val
                565                 570                 575

Met Phe Asp Pro Asp Thr Ala Ile Tyr Pro Phe Pro Lys Pro Thr
            580                 585                 590

Pro Leu Ser Ile Asp Glu Lys Ala Tyr Tyr Arg Glu Lys Ile Lys Arg
    595                 600                 605

Leu Leu Lys Glu Arg Asn Ala Val Met Val Ala His Tyr Tyr Thr Asp
    610                 615                 620

Pro Glu Ile Gln Gln Leu Ala Glu Glu Thr Gly Gly Cys Ile Ser Asp
625                 630                 635                 640

Ser Leu Glu Met Ala Arg Phe Gly Ala Lys His Pro Ala Ser Thr Leu
                645                 650                 655

Leu Val Ala Gly Val Arg Phe Met Gly Glu Thr Ala Lys Ile Leu Ser
            660                 665                 670

Pro Glu Lys Thr Ile Leu Met Pro Thr Leu Gln Ala Glu Cys Ser Leu
```

```
                    675                 680                 685

Asp Leu Gly Cys Pro Val Glu Glu Phe Asn Ala Phe Cys Asp Ala His
    690                 695                 700

Pro Asp Arg Thr Val Val Val Tyr Ala Asn Thr Ser Ala Ala Val Lys
705                 710                 715                 720

Ala Arg Ala Asp Trp Val Val Thr Ser Ser Ile Ala Val Glu Leu Ile
                    725                 730                 735

Asp His Leu Asp Ser Leu Gly Glu Lys Ile Ile Trp Ala Pro Asp Lys
                740                 745                 750

His Leu Gly Arg Tyr Val Gln Lys Gln Thr Gly Gly Asp Ile Leu Cys
            755                 760                 765

Trp Gln Gly Ala Cys Ile Val His Asp Glu Phe Lys Thr Gln Ala Leu
        770                 775                 780

Thr Arg Leu Gln Glu Glu Tyr Pro Asp Ala Ala Ile Leu Val His Pro
785                 790                 795                 800

Glu Ser Pro Gln Ala Ile Val Asp Met Ala Asp Ala Val Gly Ser Thr
                    805                 810                 815

Ser Gln Leu Ile Ala Ala Ala Lys Thr Leu Pro His Gln Arg Leu Ile
                820                 825                 830

Val Ala Thr Asp Arg Gly Ile Phe Tyr Lys Met Gln Gln Ala Val Pro
            835                 840                 845

Asp Lys Glu Leu Leu Glu Ala Pro Thr Ala Gly Glu Gly Ala Thr Cys
        850                 855                 860

Arg Ser Cys Ala His Cys Pro Trp Met Ala Met Asn Gly Leu Gln Ala
865                 870                 875                 880

Ile Ala Glu Ala Leu Glu Gln Glu Gly Ser Asn His Glu Val His Val
                    885                 890                 895

Asp Glu Arg Leu Arg Glu Arg Ala Leu Val Pro Leu Asn Arg Met Leu
                900                 905                 910

Asp Phe Ala Ala Thr Leu Arg Gly
            915                 920

<210> SEQ ID NO 52
<211> LENGTH: 906
<212> TYPE: PRT
<213> ORGANISM: Escherichia coli W3110
<220> FEATURE:
<221> NAME/KEY: PEPTIDE
<222> LOCATION: (1)..(906)
<223> OTHER INFORMATION: Fusion protein - Aspartate oxidase-FL3-
      Quinolinate sythase

<400> SEQUENCE: 52

Met Asn Thr Leu Pro Glu His Ser Cys Asp Val Leu Ile Ile Gly Ser
1               5                   10                  15

Gly Ala Ala Gly Leu Ser Leu Ala Leu Arg Leu Ala Asp Gln His Gln
                20                  25                  30

Val Ile Val Leu Ser Lys Gly Pro Val Thr Glu Gly Ser Thr Phe Tyr
            35                  40                  45

Ala Gln Gly Gly Ile Ala Ala Val Phe Asp Glu Thr Asp Ser Ile Asp
        50                  55                  60

Ser His Val Glu Asp Thr Leu Ile Ala Gly Ala Gly Ile Cys Asp Arg
65                  70                  75                  80

His Ala Val Glu Phe Val Ala Ser Asn Ala Arg Ser Cys Val Gln Trp
                85                  90                  95

Leu Ile Asp Gln Gly Val Leu Phe Asp Thr His Ile Gln Pro Asn Gly
```

```
            100                 105                 110
Glu Glu Ser Tyr His Leu Thr Arg Glu Gly His Ser His Arg Arg
            115                 120                 125
Ile Leu His Ala Ala Asp Ala Thr Gly Arg Glu Val Glu Thr Thr Leu
            130                 135                 140
Val Ser Lys Ala Leu Asn His Pro Asn Ile Arg Val Leu Glu Arg Ser
145                 150                 155                 160
Asn Ala Val Asp Leu Ile Val Ser Asp Lys Ile Gly Leu Pro Gly Thr
                    165                 170                 175
Arg Arg Val Val Gly Ala Trp Val Trp Asn Arg Asn Lys Glu Thr Val
                    180                 185                 190
Glu Thr Cys His Ala Lys Ala Val Leu Ala Thr Gly Gly Ala Ser
            195                 200                 205
Lys Val Tyr Gln Tyr Thr Thr Asn Pro Asp Ile Ser Ser Gly Asp Gly
    210                 215                 220
Ile Ala Met Ala Trp Arg Ala Gly Cys Arg Val Ala Asn Leu Glu Phe
225                 230                 235                 240
Asn Gln Phe His Pro Thr Ala Leu Tyr His Pro Gln Ala Arg Asn Phe
                245                 250                 255
Leu Leu Thr Glu Ala Leu Arg Gly Glu Gly Ala Tyr Leu Lys Arg Pro
                260                 265                 270
Asp Gly Thr Arg Phe Met Pro Asp Phe Asp Glu Arg Gly Glu Leu Ala
            275                 280                 285
Pro Arg Asp Ile Val Ala Arg Ala Ile Asp His Glu Met Lys Arg Leu
    290                 295                 300
Gly Ala Asp Cys Met Phe Leu Asp Ile Ser His Lys Pro Ala Asp Phe
305                 310                 315                 320
Ile Arg Gln His Phe Pro Met Ile Tyr Glu Lys Leu Leu Gly Leu Gly
                325                 330                 335
Ile Asp Leu Thr Gln Glu Pro Val Pro Ile Val Pro Ala Ala His Tyr
            340                 345                 350
Thr Cys Gly Gly Val Met Val Asp Asp His Gly Arg Thr Asp Val Glu
            355                 360                 365
Gly Leu Tyr Ala Ile Gly Glu Val Ser Tyr Thr Gly Leu His Gly Ala
    370                 375                 380
Asn Arg Met Ala Ser Asn Ser Leu Leu Glu Cys Leu Val Tyr Gly Trp
385                 390                 395                 400
Ser Ala Ala Glu Asp Ile Thr Arg Arg Met Pro Tyr Ala His Asp Ile
                405                 410                 415
Ser Thr Leu Pro Pro Trp Asp Glu Ser Arg Val Glu Asn Pro Asp Glu
                420                 425                 430
Arg Val Val Ile Gln His Asn Trp His Glu Leu Arg Leu Phe Met Trp
            435                 440                 445
Asp Tyr Val Gly Ile Val Arg Thr Thr Lys Arg Leu Glu Arg Ala Leu
    450                 455                 460
Arg Arg Ile Thr Met Leu Gln Gln Glu Ile Asp Glu Tyr Tyr Ala His
465                 470                 475                 480
Phe Arg Val Ser Asn Asn Leu Leu Glu Leu Arg Asn Leu Val Gln Val
                485                 490                 495
Ala Glu Leu Ile Val Arg Cys Ala Met Met Arg Lys Glu Ser Arg Gly
            500                 505                 510
Leu His Phe Thr Leu Asp Tyr Pro Glu Leu Leu Thr His Ser Gly Pro
    515                 520                 525
```

```
Ser Ile Leu Ser Pro Gly Asn His Tyr Ile Asn Arg Ile Leu Gly Gly
        530                 535                 540
Gly Ser Gly Gly Gly Ser Gly Gly Ser Ala Ala Leu Gln Met
545                 550                 555                 560
Ser Val Met Phe Asp Pro Asp Thr Ala Ile Tyr Pro Phe Pro Lys
                565                 570                 575
Pro Thr Pro Leu Ser Ile Asp Glu Lys Ala Tyr Tyr Arg Glu Lys Ile
                580                 585                 590
Lys Arg Leu Leu Lys Glu Arg Asn Ala Val Met Val Ala His Tyr Tyr
        595                 600                 605
Thr Asp Pro Glu Ile Gln Gln Leu Ala Glu Thr Gly Gly Cys Ile
        610                 615                 620
Ser Asp Ser Leu Glu Met Ala Arg Phe Gly Ala Lys His Pro Ala Ser
625                 630                 635                 640
Thr Leu Leu Val Ala Gly Val Arg Phe Met Gly Glu Thr Ala Lys Ile
                645                 650                 655
Leu Ser Pro Glu Lys Thr Ile Leu Met Pro Thr Leu Gln Ala Glu Cys
                660                 665                 670
Ser Leu Asp Leu Gly Cys Pro Val Glu Glu Phe Asn Ala Phe Cys Asp
        675                 680                 685
Ala His Pro Asp Arg Thr Val Val Tyr Ala Asn Thr Ser Ala Ala
690                 695                 700
Val Lys Ala Arg Ala Asp Trp Val Val Thr Ser Ser Ile Ala Val Glu
705                 710                 715                 720
Leu Ile Asp His Leu Asp Ser Leu Gly Glu Lys Ile Ile Trp Ala Pro
                725                 730                 735
Asp Lys His Leu Gly Arg Tyr Val Gln Lys Gln Thr Gly Gly Asp Ile
                740                 745                 750
Leu Cys Trp Gln Gly Ala Cys Ile Val His Asp Glu Phe Lys Thr Gln
                755                 760                 765
Ala Leu Thr Arg Leu Gln Glu Glu Tyr Pro Asp Ala Ala Ile Leu Val
        770                 775                 780
His Pro Glu Ser Pro Gln Ala Ile Val Asp Met Ala Asp Ala Val Gly
785                 790                 795                 800
Ser Thr Ser Gln Leu Ile Ala Ala Lys Thr Leu Pro His Gln Arg
                805                 810                 815
Leu Ile Val Ala Thr Asp Arg Gly Ile Phe Tyr Lys Met Gln Gln Ala
                820                 825                 830
Val Pro Asp Lys Glu Leu Leu Glu Ala Pro Thr Ala Gly Glu Gly Ala
                835                 840                 845
Thr Cys Arg Ser Cys Ala His Cys Pro Trp Met Ala Met Asn Gly Leu
        850                 855                 860
Gln Ala Ile Ala Glu Ala Leu Glu Gln Glu Gly Ser Asn His Glu Val
865                 870                 875                 880
His Val Asp Glu Arg Leu Arg Glu Arg Ala Leu Val Pro Leu Asn Arg
                885                 890                 895
Met Leu Asp Phe Ala Ala Thr Leu Arg Gly
        900                 905

<210> SEQ ID NO 53
<211> LENGTH: 910
<212> TYPE: PRT
<213> ORGANISM: Escherichia coli W3110
<220> FEATURE:
```

<221> NAME/KEY: PEPTIDE
<222> LOCATION: (1)..(910)
<223> OTHER INFORMATION: Fusion protein - Aspartate oxidase-FL4-
      Quinolinate sythase

<400> SEQUENCE: 53

| Met | Asn | Thr | Leu | Pro | Glu | His | Ser | Cys | Asp | Val | Leu | Ile | Ile | Gly | Ser |
|---|---|---|---|---|---|---|---|---|---|---|---|---|---|---|---|
| 1 | | | | 5 | | | | | 10 | | | | | 15 | |

| Gly | Ala | Ala | Gly | Leu | Ser | Leu | Ala | Leu | Arg | Leu | Ala | Asp | Gln | His | Gln |
|---|---|---|---|---|---|---|---|---|---|---|---|---|---|---|---|
| | | | 20 | | | | | 25 | | | | | 30 | | |

| Val | Ile | Val | Leu | Ser | Lys | Gly | Pro | Val | Thr | Glu | Gly | Ser | Thr | Phe | Tyr |
|---|---|---|---|---|---|---|---|---|---|---|---|---|---|---|---|
| | | 35 | | | | | 40 | | | | | 45 | | | |

| Ala | Gln | Gly | Gly | Ile | Ala | Ala | Val | Phe | Asp | Glu | Thr | Asp | Ser | Ile | Asp |
|---|---|---|---|---|---|---|---|---|---|---|---|---|---|---|---|
| | 50 | | | | | 55 | | | | | 60 | | | | |

| Ser | His | Val | Glu | Asp | Thr | Leu | Ile | Ala | Gly | Ala | Gly | Ile | Cys | Asp | Arg |
|---|---|---|---|---|---|---|---|---|---|---|---|---|---|---|---|
| 65 | | | | | 70 | | | | | 75 | | | | | 80 |

| His | Ala | Val | Glu | Phe | Val | Ala | Ser | Asn | Ala | Arg | Ser | Cys | Val | Gln | Trp |
|---|---|---|---|---|---|---|---|---|---|---|---|---|---|---|---|
| | | | | 85 | | | | | 90 | | | | | 95 | |

| Leu | Ile | Asp | Gln | Gly | Val | Leu | Phe | Asp | Thr | His | Ile | Gln | Pro | Asn | Gly |
|---|---|---|---|---|---|---|---|---|---|---|---|---|---|---|---|
| | | | 100 | | | | | 105 | | | | | 110 | | |

| Glu | Glu | Ser | Tyr | His | Leu | Thr | Arg | Glu | Gly | Gly | His | Ser | His | Arg | Arg |
|---|---|---|---|---|---|---|---|---|---|---|---|---|---|---|---|
| | | | 115 | | | | | 120 | | | | | 125 | | |

| Ile | Leu | His | Ala | Ala | Asp | Ala | Thr | Gly | Arg | Glu | Val | Glu | Thr | Thr | Leu |
|---|---|---|---|---|---|---|---|---|---|---|---|---|---|---|---|
| | 130 | | | | | 135 | | | | | 140 | | | | |

| Val | Ser | Lys | Ala | Leu | Asn | His | Pro | Asn | Ile | Arg | Val | Leu | Glu | Arg | Ser |
|---|---|---|---|---|---|---|---|---|---|---|---|---|---|---|---|
| 145 | | | | | 150 | | | | | 155 | | | | | 160 |

| Asn | Ala | Val | Asp | Leu | Ile | Val | Ser | Asp | Lys | Ile | Gly | Leu | Pro | Gly | Thr |
|---|---|---|---|---|---|---|---|---|---|---|---|---|---|---|---|
| | | | | 165 | | | | | 170 | | | | | 175 | |

| Arg | Arg | Val | Val | Gly | Ala | Trp | Val | Trp | Asn | Arg | Asn | Lys | Glu | Thr | Val |
|---|---|---|---|---|---|---|---|---|---|---|---|---|---|---|---|
| | | | 180 | | | | | 185 | | | | | 190 | | |

| Glu | Thr | Cys | His | Ala | Lys | Ala | Val | Val | Leu | Ala | Thr | Gly | Gly | Ala | Ser |
|---|---|---|---|---|---|---|---|---|---|---|---|---|---|---|---|
| | | 195 | | | | | 200 | | | | | 205 | | | |

| Lys | Val | Tyr | Gln | Tyr | Thr | Thr | Asn | Pro | Asp | Ile | Ser | Ser | Gly | Asp | Gly |
|---|---|---|---|---|---|---|---|---|---|---|---|---|---|---|---|
| | 210 | | | | | 215 | | | | | 220 | | | | |

| Ile | Ala | Met | Ala | Trp | Arg | Ala | Gly | Cys | Arg | Val | Ala | Asn | Leu | Glu | Phe |
|---|---|---|---|---|---|---|---|---|---|---|---|---|---|---|---|
| 225 | | | | | 230 | | | | | 235 | | | | | 240 |

| Asn | Gln | Phe | His | Pro | Thr | Ala | Leu | Tyr | His | Pro | Gln | Ala | Arg | Asn | Phe |
|---|---|---|---|---|---|---|---|---|---|---|---|---|---|---|---|
| | | | | 245 | | | | | 250 | | | | | 255 | |

| Leu | Leu | Thr | Glu | Ala | Leu | Arg | Gly | Glu | Gly | Ala | Tyr | Leu | Lys | Arg | Pro |
|---|---|---|---|---|---|---|---|---|---|---|---|---|---|---|---|
| | | | 260 | | | | | 265 | | | | | 270 | | |

| Asp | Gly | Thr | Arg | Phe | Met | Pro | Asp | Phe | Asp | Glu | Arg | Gly | Glu | Leu | Ala |
|---|---|---|---|---|---|---|---|---|---|---|---|---|---|---|---|
| | | | 275 | | | | | 280 | | | | | 285 | | |

| Pro | Arg | Asp | Ile | Val | Ala | Arg | Ala | Ile | Asp | His | Glu | Met | Lys | Arg | Leu |
|---|---|---|---|---|---|---|---|---|---|---|---|---|---|---|---|
| | 290 | | | | | 295 | | | | | 300 | | | | |

| Gly | Ala | Asp | Cys | Met | Phe | Leu | Asp | Ile | Ser | His | Lys | Pro | Ala | Asp | Phe |
|---|---|---|---|---|---|---|---|---|---|---|---|---|---|---|---|
| 305 | | | | | 310 | | | | | 315 | | | | | 320 |

| Ile | Arg | Gln | His | Phe | Pro | Met | Ile | Tyr | Glu | Lys | Leu | Leu | Gly | Leu | Gly |
|---|---|---|---|---|---|---|---|---|---|---|---|---|---|---|---|
| | | | | 325 | | | | | 330 | | | | | 335 | |

| Ile | Asp | Leu | Thr | Gln | Glu | Pro | Val | Pro | Ile | Val | Pro | Ala | Ala | His | Tyr |
|---|---|---|---|---|---|---|---|---|---|---|---|---|---|---|---|
| | | | 340 | | | | | 345 | | | | | 350 | | |

| Thr | Cys | Gly | Gly | Val | Met | Val | Asp | Asp | His | Gly | Arg | Thr | Asp | Val | Glu |
|---|---|---|---|---|---|---|---|---|---|---|---|---|---|---|---|
| | | 355 | | | | | 360 | | | | | 365 | | | |

| Gly | Leu | Tyr | Ala | Ile | Gly | Glu | Val | Ser | Tyr | Thr | Gly | Leu | His | Gly | Ala |
|---|---|---|---|---|---|---|---|---|---|---|---|---|---|---|---|
| | 370 | | | | | 375 | | | | | 380 | | | | |

```
Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
            405                 410                 415

Ser Thr Leu Pro Pro Trp Asp Glu Ser Arg Val Glu Asn Pro Asp Glu
        420                 425                 430

Arg Val Val Ile Gln His Asn Trp His Glu Leu Arg Leu Phe Met Trp
    435                 440                 445

Asp Tyr Val Gly Ile Val Arg Thr Thr Lys Arg Leu Glu Arg Ala Leu
450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg Ile Leu Gly Gly
530                 535                 540

Gly Ser Gly Gly Gly Ser Gly Gly Gly Ser Gly Gly Gly Ser Ala Ala
545                 550                 555                 560

Ala Leu Gln Met Ser Val Met Phe Asp Pro Asp Thr Ala Ile Tyr Pro
                565                 570                 575

Phe Pro Pro Lys Pro Thr Pro Leu Ser Ile Asp Glu Lys Ala Tyr Tyr
            580                 585                 590

Arg Glu Lys Ile Lys Arg Leu Leu Lys Glu Arg Asn Ala Val Met Val
        595                 600                 605

Ala His Tyr Tyr Thr Asp Pro Glu Ile Gln Gln Leu Ala Glu Glu Thr
610                 615                 620

Gly Gly Cys Ile Ser Asp Ser Leu Glu Met Ala Arg Phe Gly Ala Lys
625                 630                 635                 640

His Pro Ala Ser Thr Leu Leu Val Ala Gly Val Arg Phe Met Gly Glu
                645                 650                 655

Thr Ala Lys Ile Leu Ser Pro Glu Lys Thr Ile Leu Met Pro Thr Leu
            660                 665                 670

Gln Ala Glu Cys Ser Leu Asp Leu Gly Cys Pro Val Glu Glu Phe Asn
        675                 680                 685

Ala Phe Cys Asp Ala His Pro Asp Arg Thr Val Val Tyr Ala Asn
690                 695                 700

Thr Ser Ala Ala Val Lys Ala Arg Ala Asp Trp Val Val Thr Ser Ser
705                 710                 715                 720

Ile Ala Val Glu Leu Ile Asp His Leu Asp Ser Leu Gly Glu Lys Ile
                725                 730                 735

Ile Trp Ala Pro Asp Lys His Leu Gly Arg Tyr Val Gln Lys Gln Thr
            740                 745                 750

Gly Gly Asp Ile Leu Cys Trp Gln Gly Ala Cys Ile Val His Asp Glu
        755                 760                 765

Phe Lys Thr Gln Ala Leu Thr Arg Leu Gln Glu Glu Tyr Pro Asp Ala
        770                 775                 780

Ala Ile Leu Val His Pro Glu Ser Pro Gln Ala Ile Val Asp Met Ala
785                 790                 795                 800

Asp Ala Val Gly Ser Thr Ser Gln Leu Ile Ala Ala Ala Lys Thr Leu
```

-continued

```
                    805                 810                 815
Pro His Gln Arg Leu Ile Val Ala Thr Asp Arg Gly Ile Phe Tyr Lys
            820                 825                 830

Met Gln Gln Ala Val Pro Asp Lys Glu Leu Leu Glu Ala Pro Thr Ala
            835                 840                 845

Gly Glu Gly Ala Thr Cys Arg Ser Cys Ala His Cys Pro Trp Met Ala
        850                 855                 860

Met Asn Gly Leu Gln Ala Ile Ala Glu Ala Leu Glu Gln Glu Gly Ser
865                 870                 875                 880

Asn His Glu Val His Val Asp Glu Arg Leu Arg Glu Arg Ala Leu Val
                885                 890                 895

Pro Leu Asn Arg Met Leu Asp Phe Ala Ala Thr Leu Arg Gly
            900                 905                 910

<210> SEQ ID NO 54
<211> LENGTH: 10
<212> TYPE: PRT
<213> ORGANISM: Artificial Sequence
<220> FEATURE:
<223> OTHER INFORMATION: HL1 Linker peptide

<400> SEQUENCE: 54

Leu Ala Glu Ala Ala Ala Lys Ala Ala Ala
1               5                   10

<210> SEQ ID NO 55
<211> LENGTH: 15
<212> TYPE: PRT
<213> ORGANISM: Artificial Sequence
<220> FEATURE:
<223> OTHER INFORMATION: HL2 Linker peptide

<400> SEQUENCE: 55

Leu Ala Glu Ala Ala Ala Lys Glu Ala Ala Lys Ala Ala Ala
1               5                   10                  15

<210> SEQ ID NO 56
<211> LENGTH: 20
<212> TYPE: PRT
<213> ORGANISM: Artificial Sequence
<220> FEATURE:
<223> OTHER INFORMATION: HL3 Linker peptide

<400> SEQUENCE: 56

Leu Ala Glu Ala Ala Ala Lys Glu Ala Ala Lys Glu Ala Ala
1               5                   10                  15

Lys Ala Ala Ala
            20

<210> SEQ ID NO 57
<211> LENGTH: 25
<212> TYPE: PRT
<213> ORGANISM: Artificial Sequence
<220> FEATURE:
<223> OTHER INFORMATION: HL4 Linker peptide

<400> SEQUENCE: 57

Leu Ala Glu Ala Ala Ala Lys Glu Ala Ala Lys Glu Ala Ala
1               5                   10                  15

Lys Glu Ala Ala Ala Lys Ala Ala Ala
            20                  25
```

```
<210> SEQ ID NO 58
<211> LENGTH: 30
<212> TYPE: PRT
<213> ORGANISM: Artificial Sequence
<220> FEATURE:
<223> OTHER INFORMATION: HL5 Linker peptide

<400> SEQUENCE: 58

Leu Ala Glu Ala Ala Ala Lys Glu Ala Ala Lys Glu Ala Ala
  1               5                  10                  15

Lys Glu Ala Ala Ala Lys Glu Ala Ala Lys Ala Ala Ala
                20                  25                  30

<210> SEQ ID NO 59
<211> LENGTH: 16
<212> TYPE: PRT
<213> ORGANISM: Artificial Sequence
<220> FEATURE:
<223> OTHER INFORMATION: FL3 Linker peptide

<400> SEQUENCE: 59

Leu Gly Gly Gly Ser Gly Gly Gly Ser Gly Gly Gly Ser Ala Ala Ala
  1               5                  10                  15

<210> SEQ ID NO 60
<211> LENGTH: 20
<212> TYPE: PRT
<213> ORGANISM: Artificial Sequence
<220> FEATURE:
<223> OTHER INFORMATION: FL4 Linker peptide

<400> SEQUENCE: 60

Leu Gly Gly Gly Ser Gly Gly Gly Ser Gly Gly Gly Ser Gly Gly Gly
  1               5                  10                  15

Ser Ala Ala Ala
               20

<210> SEQ ID NO 61
<211> LENGTH: 8
<212> TYPE: PRT
<213> ORGANISM: Artificial Sequence
<220> FEATURE:
<223> OTHER INFORMATION: FL1 Linker peptide

<400> SEQUENCE: 61

Leu Gly Gly Gly Ser Ala Ala Ala
  1               5

<210> SEQ ID NO 62
<211> LENGTH: 12
<212> TYPE: PRT
<213> ORGANISM: Artificial Sequence
<220> FEATURE:
<223> OTHER INFORMATION: FL2 Linker peptide

<400> SEQUENCE: 62

Leu Gly Gly Gly Ser Gly Gly Gly Ser Ala Ala Ala
  1               5                  10

<210> SEQ ID NO 63
<211> LENGTH: 24
<212> TYPE: PRT
<213> ORGANISM: Artificial Sequence
<220> FEATURE:
<223> OTHER INFORMATION: FL5 Linker peptide

<400> SEQUENCE: 63
```

```
Leu Gly Gly Gly Ser Gly Gly Gly Ser Gly Gly Gly Ser Gly Gly Gly
  1               5                  10                 15
Ser Gly Gly Gly Ser Ala Ala Ala
                20
```